United States Patent [19]

Wingert et al.

[11] Patent Number: 5,221,762

[45] Date of Patent: Jun. 22, 1993

[54] PREPARATION OF E-OXIME ETHERS OF PHENYLGLYOXYLIC ESTERS

[75] Inventors: Horst Wingert, Mannheim; Bernd Wolf, Fussgoenheim; Remy Benoit, Ludwigshafen; Hubert Sauter, Mannheim; Michael Hepp, Ladenburg; Wassilios Grammenos, Ludwigshafen; Thomas Kuekenhoehner, Frankenthal, all of Fed. Rep. of Germany

[73] Assignee: BASF Akitenegesellschaft, Ludwigshafen, Fed. Rep. of Germany

[21] Appl. No.: 806,295

[22] Filed: Dec. 13, 1991

[30] Foreign Application Priority Data

Dec. 31, 1990 [DE] Fed. Rep. of Germany ....... 4042271
Dec. 31, 1990 [DE] Fed. Rep. of Germany ....... 4042272
Dec. 31, 1990 [DE] Fed. Rep. of Germany ....... 4042273
Dec. 31, 1990 [DE] Fed. Rep. of Germany ....... 4042280
Dec. 31, 1990 [DE] Fed. Rep. of Germany ....... 4042282
Dec. 31, 1990 [DE] Fed. Rep. of Germany ....... 4042283

[51] Int. Cl.$^5$ .................. C07C 229/00; C07C 69/76; C07C 253/00
[52] U.S. Cl. ........................ 560/35; 560/51; 560/53; 560/60; 562/470; 562/840; 558/345
[58] Field of Search ............ 560/35, 51, 53, 60; 558/345; 562/470, 840

[56] References Cited

U.S. PATENT DOCUMENTS 4,069,252 1/1978 Findeisen et al. ............ 260/545 R
4,829,085 5/1989 Wenderoth et al. ............ 514/522

FOREIGN PATENT DOCUMENTS 0253213 1/1988 European Pat. Off. .
0254426 1/1988 European Pat. Off. .
0400417 5/1990 European Pat. Off. .
0398692 11/1990 European Pat. Off. .
1279682 10/1968 Fed. Rep. of Germany .

OTHER PUBLICATIONS

Morrison and Boyd, Organic Chemistry, 3rd Ed., Allyn and Bacon, Inc., Boston, Mass., 1973.

Primary Examiner—Paul J. Killos
Assistant Examiner—Porfirio Nazario
Attorney, Agent, or Firm—Oblon, Spivak, McClelland, Maier & Neustadt

[57] ABSTRACT

E-oxime ethers of phenylglyoxylic esters of the formula I

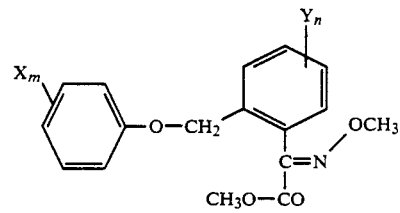

where
X and Y are each halogen, $C_1$–$C_4$-alkyl, $C_1$–$C_4$-alkoxy or trifluoromethyl;
m is an integer from 0 to 4;
n is an integer from 0 to 3;
are prepared.

8 Claims, No Drawings

PREPARATION OF E-OXIME ETHERS OF PHENYLGLYOXYLIC ESTERS

The present invention relates to a process for preparing E-oxime ethers of phenylglyoxylic esters of the formula I

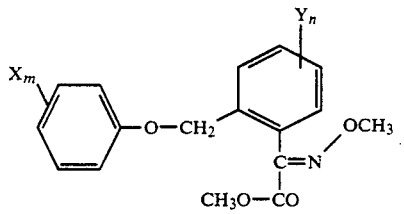

where X and Y are each halogen, $C_1$-$C_4$-alkyl, $C_1$-$C_4$-alkoxy or trifluoromethyl; m is an integer from 0 to 4; n is an integer from 0 to 3.

The preparation of oxime ethers of the type of compounds I by reaction of glyoxylic esters with O-methylhydroxylamine hydrochloride has been disclosed (cf., for example, EP-A 253 213 and EP-A 254 426), wherein equimolar amounts of hydrogen chloride are formed as by-product. However, the disadvantage of this process is that mixtures of E and Z isomers of the oxime ethers are produced and can be separated industrially only at relatively great expense. Moreover, the isomer with the preferred E configuration is often obtained in only very small amounts.

It is an object of the present invention to improve access to the compounds I.

We have found that this object is achieved by a process for preparing E-oxime ethers of phenylglyoxylic esters I, which comprises a) converting a phenol of the formula II

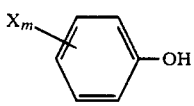

into the phenolate using a base in the presence of a diluent, b) mixing this phenolate with a lactone of the formula III

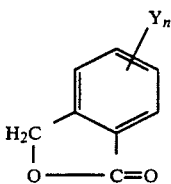

c) removing the diluent by distillation and reacting the mixture in the melt at from 50° to 250° C., and
d) dissolving the still liquid melt in water and acidifying, and converting the resulting 2-phenoxymethylbenzoic acid of the formula IV

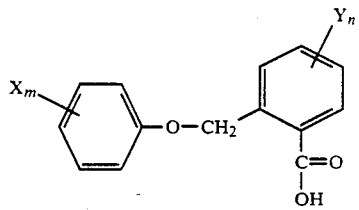

e) in a conventional manner with phosgene or thionyl chloride into the corresponding 2-phenoxymethylbenzoyl chloride of the formula V

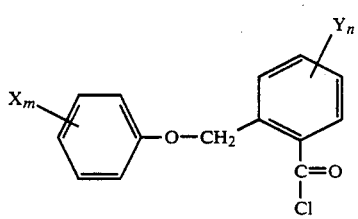

and f) reacting the 2-phenoxymethylbenzoyl chloride V with an alkali metal or alkaline earth metal cyanide, if required in the presence of hydrocyanic acid, and g) reacting the resulting 2-phenoxymethylbenzoyl cyanide of the formula VI

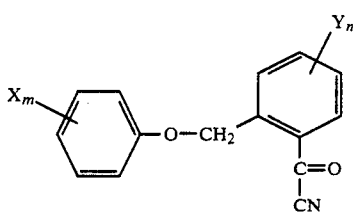

with methanol in the presence of an acid, h) if required cleaving the keto carboxylic ester dimethyl acetal byproduct of the formula VIIb

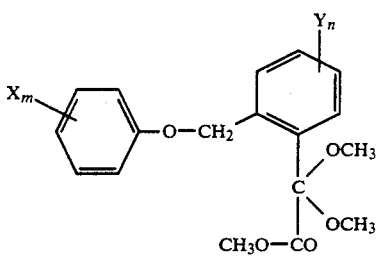

under acidic conditions, and, if required, subjecting the α-keto carboxamide byproduct of the formula VIIc

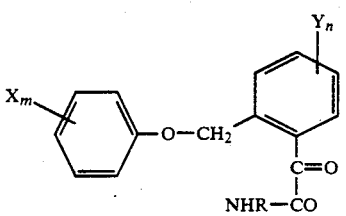

where R is hydrogen or acyl, to step (g) again or i) reacting an o-phenoxymethylbenzoic ester of the formula Va

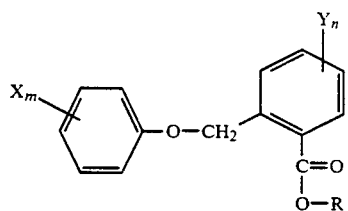
Va where R is $C_1$–$C_4$-alkyl, with dimethyl sulfoxide in the presence of a base, mixing the resulting β-keto sulfoxide of the formula VIa

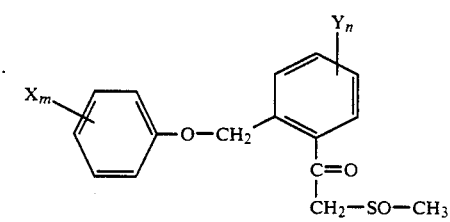
VIa with a halogenating agent and reacting this mixture with methanol in the presence of an acid k) and reacting the resulting methyl 2-phenoxymethyl-glyoxylate of the formula VIIa

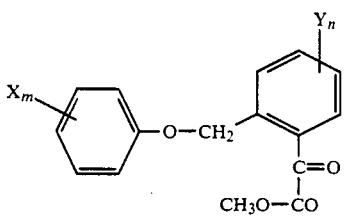
VIIa or an acetal of the formula VIIb

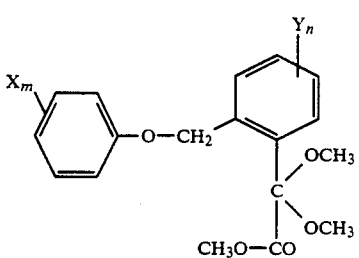
VIIb or a mixture of compounds VIIa and VIIb with O-methylhydroxylamine or one of its acid addition salts, and treating simultaneously or subsequently with an acid.

We have found also that this object is achieved by a process for preparing E-oxime ethers of phenylglyoxylic esters I, which comprises phenylglyoxylic esters of the formula VIIa

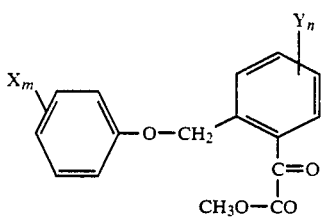
VIIa or acetals of phenylglyoxylic esters of the formula VIIb

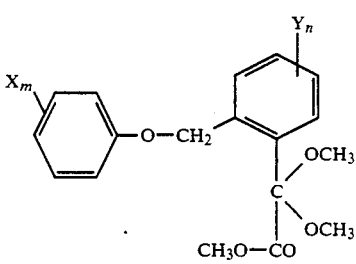
VIIb or a mixture of VIIa and VIIb, being reacted with O-methylhydroxylamine or one of its acid addition salts and, simultaneously or subsequently, treated with an acid.

The phenylglyoxylic esters of the formula VIIa used as starting materials can be obtained by the following process, for example:

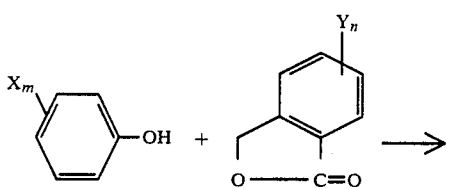
II    III

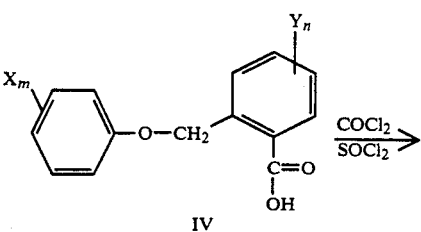
IV

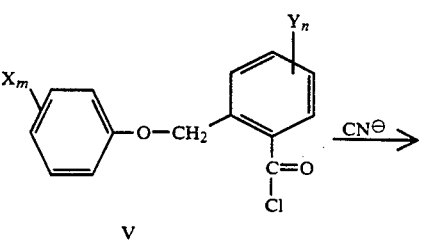
V

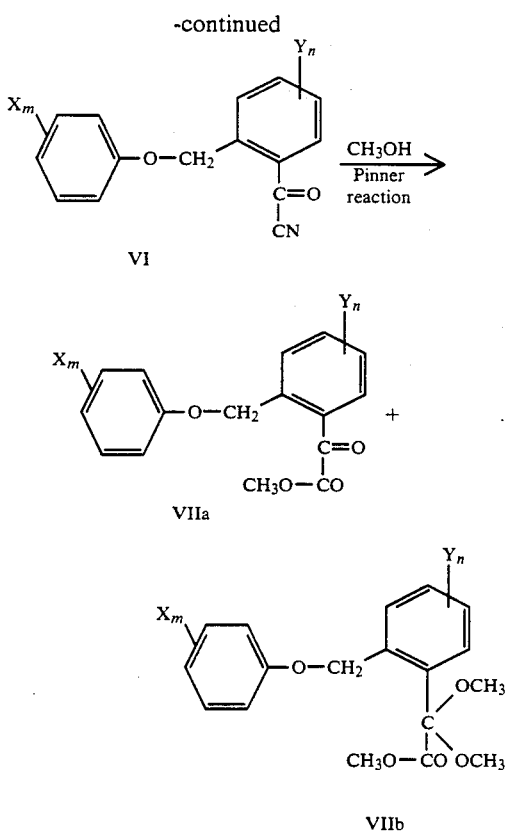

In the first step, phenols of the formula II are reacted with lactones of the formula III, preferably under basic conditions [cf., for example, Coll. Czech. Chem. Commun. 32 (1967) 3448]. The resulting o-(phenoxymethyl)-benzoic acids IV are expediently converted into their chlorides V (cf. Organikum, VEB Deutscher Verlag der Wissenschaften, 16th Edition, Berlin 1986, page 423 et seq.) which are then converted into the corresponding benzoyl cyanides VI. The benzoyl cyanides VI are finally subjected to a Pinner reaction (cf. Angew, Chemie 94 (1982) 1) which produces both the phenylglyoxylic esters VIIa and, as byproducts, the acetals of the phenylglyoxylic esters VIIb. The latter can be converted into a conventional manner by treatment with acids such as hydrochloric acid into the compounds VIIa.

Both the phenylglyoxylic esters VIIa and the acetals of the phenylglyoxylic esters VIIb, or mixtures of these compounds, are suitable as starting materials for the process according to the invention. In particular, the mixture of phenylglyoxylic esters VIIa and acetals of phenylglyoxylic esters VIIb crude products of the Pinner reaction can, without further purification, be converted by this process into the E-oxime ethers of phenylglyoxylic esters I.

The O-methylhydroxylamine is employed either in the form of an acid addition salt or as free base, it being possible to liberate the unprotonated compound from the salt by addition of a strong base. Suitable salts of O-methylhydroxylamine are those with monobasic to tribasic acids such as, in particular, hydrochloric acid and sulfuric acid.

The reaction is generally carried out in the presence of a solvent or diluent.

Suitable and preferred solvents are aromatic hydrocarbons such as benzene, toluene and o-, m- and p-xylene, chlorohydrocarbons such as methylene chloride, alcohols such as methanol and ethers such as diethyl ether. Methanol is particularly preferred.

The ratios of the amounts of the precursors are not critical; it is expedient to employ stoichiometric amounts of starting compounds unless an excess of one of the components, eg. 10 mol%, is advisable.

The reaction is normally carried out at from 0° to 100° C., preferably from 20° to 80° C.

One variant of the process comprises reacting the mixture of the compounds VIIa and VIIb obtained from the Pinner reaction, without isolation from the reaction mixture, with O-methylhydroxylamine or one of its acid addition salts.

The oxime ethers of phenylglyoxylic esters are usually obtained as mixtures of isomers, with the oxime double bond being partly in the E and partly in the Z configuration. Rearrangement of the oxime ethers to the E configuration takes place on treatment with acid.

For this purpose, the crude solution can previously be concentrated or further diluted. If required, the rearrangement can also take place in a two-phase system composed of water/acid and an organic solvent such as dichloromethane. However, it is expedient to treat the resulting crude solution of the oxime ether without further concentration or dilution directly with the acid.

Particularly suitable acids are mineral acids, for example perchloric acid, sulfuric acid, phosphoric acid and hydrohalic acids such as hydrogen chloride, aliphatic sulfonic acids such as trifluoromethanesulfonic acid, aromatic sulfonic acids such as p-toluenesulfonic acid, and halogenated alkanecarboxylic acids such as trifluoroacetic acid. Gaseous hydrogen chloride is particularly preferred.

The molar amount of acid is normally from 1 to 20 times, in particular 3 to 10 times, the amount of VIIa or VIIa and VIIb.

The isomerization is generally carried out at from $-20°$ to 100° C., in particular from 20° to 80° C.

The rearrangement of the oxime ethers takes from about 1 to 90 hours, preferably 4 to 20 hours, depending on the temperature and, in particular, the amount of acid.

As a rule, all the said steps can be carried out under atmospheric pressure or under the autogenous pressure of the system, up to about 5 bar. A higher or lower pressure is also possible but generally has no advantages.

The process according to the invention can be carried out either batchwise or continuously. When carried out continuously, the reactants are passed, for example, through a tubular reactor or cascades of stirred vessels.

The process according to the invention can be used successfully to synthesize all the E-oxime ethers of phenylglyoxylic esters complying with the definition, especially those compounds where X and Y have, independently of one another, the following meanings: halogen such as fluorine, chlorine and bromine; branched or unbranched $C_1$–$C_4$-alkyl such as methyl, ethyl, isopropyl and n-butyl, especially methyl and ethyl; $C_1$–$C_4$-alkoxy such as methoxy, ethoxy, 1-methylethoxy and n-propoxy; trifluoromethyl.

The E-oxime ethers of phenylglyoxylic esters I are obtained by the process according to the invention in surprisingly high yield and excellent purity. The expectation from the prior art was, by contrast, that the same difficulties would occur in the process as with the previously disclosed preparation processes. In particular, it was entirely unpredictable that isomerization with predominant formation of the E-isomer takes place under acid conditions, because equimolar amounts of hydrogen chloride are produced in the known synthetic methods on use of O-methylhydroxylamine hydrochloride without there being preferential production of one isomer. Furthermore, decomposition of the oxime ether would have been expected on treatment of the crude products with acid.

The process according to the invention has a number of advantages: it can be carried out on the industrial scale in a very straightforward manner; the salts of O-methylhydroxylamine can be employed as aqueous solutions; the phenylglyoxylic ester VIIa can be employed as crude product from the previous stage because its dimethyl acetal which is present as impurity is, surprisingly, also converted into the required oxime ether.

The E-oxime ethers of phenylglyoxylic esters I are described in EP-A 253 213 and EP-A 254 426 as crop protection agents.

EXAMPLE 1

Methyl E-2-(phenoxymethyl)phenylglyoxylate O-methyloxime

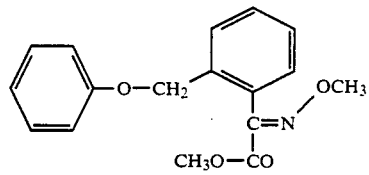

A mixture of 6.1 g (22.5 mmol) of methyl 2-(phenoxymethyl)phenylglyoxylate, 2.1 g (25 mmol) of O-methylhydroxylamine hydrochloride and 40 ml of methanol was refluxed for 9 hours. The solvent was then removed under reduced pressure, 100 ml of methylene chloride were added to the residue, and gaseous hydrogen chloride was passed in at 20° C. until saturated. The solution was stirred at 20° C. for 12 hours and then washed with water, dried and concentrated. The brownish crude product crystallized on trituration with cold methanol. Yield: 6.3 g.

$^1$H-NMR (in CDCl$_3$; TMS as internal standard): 7.55 ppm (d, 1H), 7.40 ppm (m, 2H), 7.25 ppm (m, 3H), 6.90 ppm (m, 3H), 4.95 ppm (s, 2H), 4.00 ppm (s, 3H), 3.85 ppm (s, 3H).

Precursor 1.1
2-(Phenoxymethyl)benzoic acid

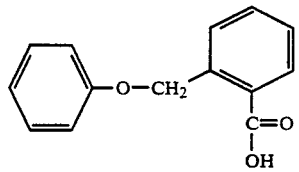

A mixture of 151 g (1.6 mol) of phenol, 106 g of 85 % by weight aqueous potassium hydroxide solution (corresponding to 1.6 mol of KOH) and 1.5 l of xylene was refluxed with continuous removal of water. After the water had been removed, 201 g (1.5 mol) of phthalide and 57 ml of dimethylformamide were added to the reaction mixture at 100° C., and the mixture was then stirred at this temperature for 15 hours. After cooling to 20-25° C., the product mixture was extracted twice with 2 l of water each time and then 140 ml of 38 % by weight aqueous hydrochloric acid were added. The crystals which had formed were separated off, washed with 500 ml of water and dried. The crude product was purified by dissolving in 550 ml of hot acetone and reprecipitated by adding 3 l of water. Yield: 296 g; melting point: 125-127° C.;

$^1$H-NMR (in CDCl$_3$; TMS as internal standard): 5.55 ppm (s, 2H); 7.00 ppm (m, 3H); 7.30 ppm (t, 2H); 7.40 ppm (t, 1H); 7.65 ppm (t, 1H); 7.85 ppm (d, 1H); 8.20 ppm (d, 1H).

Precursor 1.2
2-Phenoxymethylbenzoyl chloride

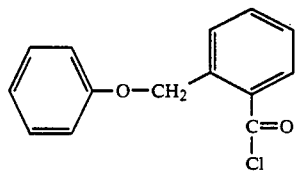

A mixture of 72 g (0.32 mol) of 2-phenoxymethylbenzoic acid, 56 g (0.47 mol) of thionyl chloride and 300 ml of 1,2-dichloroethane was refluxed for 3 hours. The volatiles were removed under reduced pressure to give a dark oil which slowly crystallized. Yield: 79 g.

$^1$H-NMR (in CDCl$_3$; TMS as internal standard): 5.35 ppm (s, 2H); 6.95 ppm (m, 3H); 7.3 ppm (t, 2H); 7.5 ppm (t, 1H); 7.7 ppm (t, 1H); 7.85 ppm (d, 1H); 8.35 ppm (d, 1H).

Precursor 1.3
2-Phenoxymethylbenzoyl cyanide

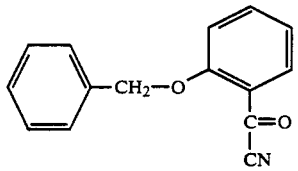

A mixture of 79 g (0.32 mol) of 2-phenoxymethylbenzoyl chloride, 17 g (0.347 mol) of sodium cyanide, 0.3 g (0.93 mmol) of tetrabutylammonium bromide, 200 ml of water and 300 ml of 1,2-dichloroethane was stirred vigorously at 20° C. for 2 hours. The phases were then separated and the aqueous phase was extracted with 100 ml of 1,2-dichloroethane. The combined organic phases were washed three times with 100 ml of water each time and then dried. The solvent was removed under reduced pressure to give 70.8 g of a brownish oil which crystallized on trituration with methyl tert-butyl ether/pentane (1:1).

$^1$H-NMR (in CDCl$_3$; TMS as internal standard): 8.40 ppm (d, 1H); 8.00 ppm (d, 1H); 7.80 ppm (t, 1H); 7.60 ppm (t, 1H); 7.35 ppm (t, 2H); 7.00 ppm (m, 3H); 5.45 ppm (s, 2H).

Precursor 1.4
Methyl 2-(phenoxymethyl)phenylglyoxylate

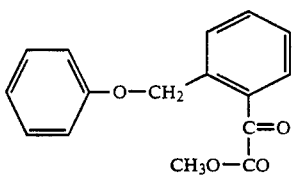

Gaseous hydrogen chloride was passed to saturation into a mixture of 10 g (42 mmol) of 2-(phenoxymethyl)-benzoyl cyanide, 4.3 g (42 mmol) of acetic anhydride and 50 ml of methyl tert-butyl ether while stirring at 0° to −5° C. The result after stirring at 20° C. for 10 hours was a solution, to which 50 ml of methanol were added. The mixture was refluxed for 10 hours and then volatiles were removed under reduced pressure, after which the residue was dissolved in 150 ml of methyl tert-butyl ether. The organic phase was washed twice with 100 ml of water each time and then dried and concentrated to give an oily mixture of 68 % of the required product and 32 % of the corresponding dimethyl acetal. To cleave the dimethyl acetal, the mixture was dissolved in 50 ml of dichloromethane and stirred with 10 ml of concentrated hydrochloric acid at 20° to 25° C. for 10 hours. The organic phase was then separated off, washed three times with 50 ml of water each time, dried and concentrated. Yield: 9.7 g (reddish oil).

$^1$H-NMR (in CDCl$_3$; TMS as standard): 7.75 ppm (m, 2H), 7.60 ppm (t, 1H), 7.45 ppm (t, 1H), 7.30 ppm (m, 2H), 6.95 ppm (m, 3H), 5.40 ppm (s, 2H) and 3.80 ppm (s, 3H).

EXAMPLE 2

Methyl E-2-(2-methylphenoxymethyl)phenylglyoxylate O-methyloxime

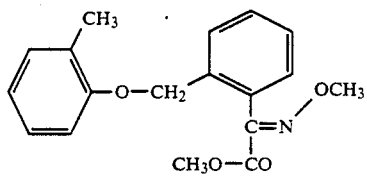

Variant 2.1

129 g of a mixture composed of 80 % by weight of methyl 2-(2-methylphenoxymethyl)phenylglyoxylate and 13 % by weight of methyl 2-(2-methylphenoxymethyl)phenylglyoxylate dimethyl acetal were refluxed together with 41.7 g (0.5 mol) of O-methylhydroxylamine hydrochloride and 450 ml of methanol for 7 hours. The mixture was cooled to 20° C. and then 450 ml of methylene chloride were added and 219 g (6 mol) of gaseous hydrogen chloride were passed in. The mixture was stirred at this temperature for 15 hours and then the solvent was removed under reduced pressure. The residue was washed first with cold methanol and then with petroleum ether and subsequently dried. Yield: 106.8 g (colorless solid).

Variant 2.2

A mixture of 56.8 g of methyl 2-(2-methylphenoxymethyl)phenylglyoxylate (90 % pure; 0.18 mol), 55.7 g of a 30 % strength aqueous solution of O-methylhydroxylamine hydrochloride (=0.20 mol) and 200 ml of methanol was refluxed for 7 hours. Then, at 0° to 10° C., 72 g (1.97 mol) of gaseous hydrogen chloride were passed into the mixture, 200 ml of methylene chloride were added and the mixture was then stirred at 20° to 25° C. for three days. The residue after removal of the solvent under reduced pressure was washed with cold methanol and petroleum ether and then dried. Yield: 50.5 g Variant 2.3

1343 g (36.8 mol) of gaseous hydrogen chloride were passed at −18° to −8° C. into a mixture of 753 g (3 mol) of 2-(2-methylphenoxymethyl)benzoyl cyanide, 336.6 g (3.3 mol) of acetic anhydride and 2.3 l of methyl tert-butyl ether. The mixture was then stirred at 20 to 25° C. for 36 hours, 1.8 l of methanol were added and the mixture was then refluxed for 15 hours. After cooling to 20° to 25° C., the solvent was removed under reduced pressure, and 1 l of methylene chloride was added to the residue. The organic phase was first washed with 800 ml of water and then 800 ml of concentrated aqueous hydrochloric acid were added and the mixture was stirred at 20 to 25° C. for 15 hours. After phase separation, the aqueous phase was washed with 0.5 l of methylene chloride. The combined organic phases were concentrated.

Then 2 l of methanol and 250.5 g (3 mol) of O-methylhydroxylamine hydrochloride were added to the crude product (main component methyl 2-(2-methylphenoxymethyl)phenylglyoxylate), and this mixture was refluxed for 15 hours. 2 l of methylene chloride were then added to the reaction mixture at 20° to 25° C. 986 g (27 mol) of gaseous hydrogen chloride were then passed in and the mixture was stirred for a further 48 hours. The solvent was removed under reduced pressure, and the residue was washed with methanol, water and petroleum ether and then dried. Total yield: 814 g.

Variant 2.4

A mixture of 57.9 g (0.2 mol) of methyl 2-(2-methylphenoxymethyl)phenylglyoxylate, 18.4 g (0.22 mol) of O-methylhydroxylamine hydrochloride and 135 ml of methanol was refluxed for 6 hours. Then 36.5 g (1.0 mol) of gaseous hydrogen chloride were passed into the mixture at 20° C. and the mixture was stirred at 20° C. for 24 hours. The precipitated solid was filtered off with suction, washed with 100 ml of cold methanol and dried. Yield: 57.2 g.

Melting point 97–98° C.

$^1$H-NMR (in CDCl$_3$; TMS as internal standard): 2.22 ppm (3H), 3.8 ppm (3H), 4.02 ppm (3H), 4.94 ppm (2H), 6.8 ppm (2H), 7.11 ppm (2H), 7.2 ppm (1H), 7.4 ppm (2H), 7.57 ppm (1H).

The present invention furthermore relates to a process for preparing 2-phenoxymethylbenzoic acids of the formula IV

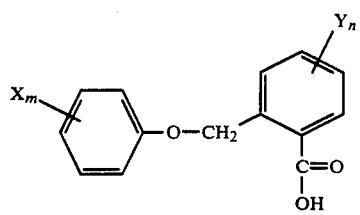

where

X and Y are each halogen, $C_1$–$C_4$-alkyl, $C_1$–$C_4$-alkoxy or trifluoromethyl;

m is an integer from 0 to 4;

n is an integer from 0 to 3.

The preparation of 2-phenoxymethylbenzoic acids by fusing together phenolates and phthalides has been disclosed (cf., for example, Coll. Czech. Chem. Commun. 32 (1967) 3448, J. Chem. Soc. (1964), 4074, DE-A 22 08 893, DE-A 24 35 613 and U.S. Pat. NO. 4 282 365). In these processes, phenols are initially converted with a base into the corresponding phenolates which are then isolated as solids by removing the solvent by distillation. However, this step can be carried out industrially only with difficulty because there is increasing difficulty in mixing the crystallizing phenolate as the amount of solvent decreases. Hence reliable temperature control is no longer possible so that boiling is extremely uneven.

Furthermore, after addition of the phthalide to the phenolate it is necessary to convert the solid mixture into a melt, which is costly. There are, moreover, problems with mixing and it often occurs that large lumps of phenolate in the phthalide melt impair stirring or damage the stirrer.

Another disadvantage is that in the known process the melt must be cooled to room temperature before being treated with water. This procedure is very time-consuming. In addition, when carried out on the industrial scale, a stirrer with a variable depth of immersion is necessary so that it can be removed from the melt before cooling, or a second independent stirrer must be installed for the dissolving process.

Another disadvantage of the known processes is that the purity of the resulting acids is inadequate and they have to be purified by subsequent recrystallization. In addition, yields of only 60–70% are achieved.

DE-A 2 749 957 (Example 6) and RO 78, 601 disclose that 2-phenoxymethylbenzoic acids can also be prepared by reacting alkali metal phenolates with phthalide or substituted phthalides in solvents at elevated temperatures.

However, the disadvantages of this procedure are that very long reaction times and large amounts of solvent are required. Furthermore, the process described in DE-A 27 49 957 is rather costly on the industrial scale because the use of sodium hydride as base and the formation of hydrogen in the reaction mean that special safety measures are necessary.

It is an object of the present invention to improve access to compounds IV.

We have found that this object is achieved by a process for preparing 2-phenoxymethylbenzoic acids of the formula IV, which comprises
a) converting a phenol of the formula II

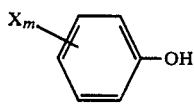

with a base into the phenolate in the presence of a diluent, b) mixing this phenolate with a lactone of the formula III

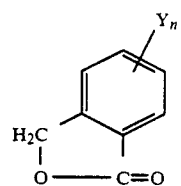

c) removing the diluent by distillation and reacting the molten mixture at from 50° to 250° C., and d) dissolving the melt while still liquid in water and acidifying.

Particularly suitable bases are alkali metal hydroxides such as sodium and potassium hydroxide and alkali metal and alkaline earth metal alcoholates such as sodium methanolate, sodium ethanolate and potassium methanolate; the alkali metal alcoholates are particularly preferred.

As a rule, step (a) is carried out in the presence of a solvent or diluent, with the reaction normally being carried out at from 0° to 100° C., preferably from 20° to 80° C.

Suitable solvents or diluents are aromatic hydrocarbons such as benzene, toluene and o-, m- and p-xylene, alcohols such as methanol, ethanol and isopropanol, ethers such as tetrahydrofuran or mixtures of the said solvents. Methanol and ethanol are particularly preferred.

The amount of base is not critical. At least equimolar amounts of base are necessary for complete conversion of the phenols II into the corresponding phenolates; an excess of from 1 to 6 mol % of base, based on the amount of lactone III, is preferably used.

The phenolates of the compounds II are, according to the invention, not isolated before being mixed and fused with the lactones of the formula III, with removal of the solvent.

In general, this step (c) is carried out at from 50° to 250° C., preferably from 160° to 220° C. As the amount of solvent decreases, the lactone III is converted from the dissolved to the liquid state, resulting in a solution of the phenolate in the lactone III which can be efficiently mixed.

The phenolate and lactone are normally employed in approximately the stoichiometric ratio, but in some cases an excess of one of the components, up to about 10 mol %, may be advisable.

No special pressure conditions are necessary for stages (a) to (c) and thus they are expediently carried out under atmospheric pressure.

To stop the reaction, the melt is diluted, advantageously while still in the liquid state, with water. The resulting solution is acidified to liberate the 2-phenoxymethylbenzoic acid IV, preferably with an inorganic acid such as hydrochloric acid or sulfuric acid. Subsequent workup is by conventional means.

The process according to the invention can be carried out either batchwise or continuously. When carried out continuously, the reactants are passed, for example, through a tubular reactor or a cascade of stirred vessels.

The method of preparation described can be used successfully to synthesize all 2-phenoxymethylbenzoic acids IV complying with the definition, especially those compounds where X and Y are each halogen such as fluorine, chlorine and bromine, especially fluorine and chlorine;

branched or unbranched $C_1$-$C_4$-alkyl such as methyl, ethyl, isopropyl and n-butyl, especially methyl and ethyl;

$C_1$-$C_4$-alkoxy such as methoxy, ethoxy, 1-methylethoxy and n-propoxy;

trifluoromethyl.

The 2-phenoxymethylbenzoic acids of the formula IV are obtainable by the process according to the invention in surprisingly high yield and excellent purity. The expectation from the prior art was, by contrast, that the same difficulties would occur in the process as with the previously disclosed preparation processes. In particular, it was entirely unpredictable that the alkali metal phenolate did not precipitate as solid in the presence of the lactone after removal of the diluent by distillation. On the contrary, a viscous, solid-containing reaction mixture which is difficult to stir would have been expected. Furthermore, it was entirely unexpected that water can be added dropwise without difficult at the maximum reaction temperature (about 200° C.) without the melt solidifying.

The process according to the invention has a number of advantages compared with the prior art. It can be carried out on the industrial scale in a very straightforward manner. It is crucial that the intermediate alkali metal phenolate no longer needs to be isolated as solid but that a transition from the solution or suspension of the phenolate into the melt (phenolate +lactone III) is continuous. This is achieved by adding the lactone III after the phenol II has been converted, in the presence of a diluent, using a base into the phenolate and the diluent has subsequently been removed by distillation.

An additional crucial advantage of the process according to the invention is that the melt does not have to be cooled and that water is added to the liquid melt (at about 200° C.) with reflux cooling. The reaction mixture remains easy to stir during the dilution, and the temperature decreases gradually as the amount of water increases. The result when addition of water is complete is a clear solution of the alkali metal slat of the acid IV. The acid IV precipitated on acidification is removed and washed with a little water.

The 2-phenoxymethylbenzoic acids IV are valuable intermediates for the synthesis of E-oxime ethers of phenylglyoxylic esters I which are used in crop protection, especially as fungicides (cf. EP-A 253 213 and EP-A 254 426).

A particularly preferred route for synthesizing compounds I from the 2-phenoxymethylbenzoic acids IV is depicted below:

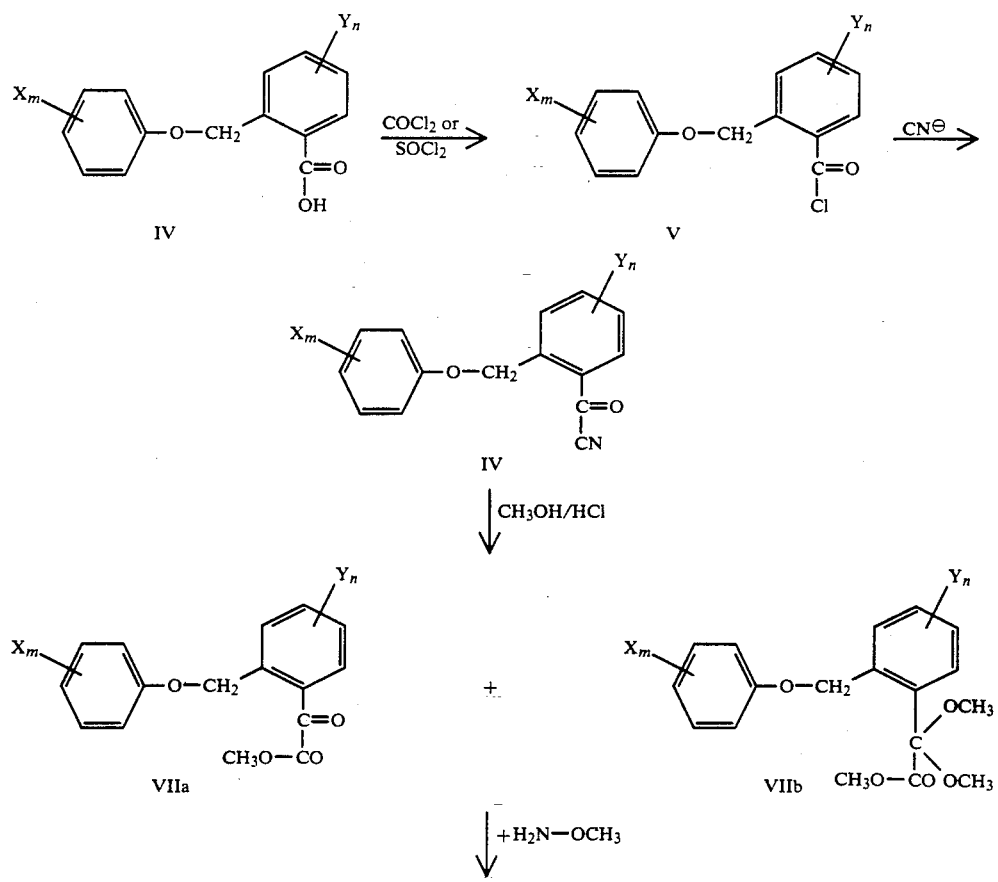

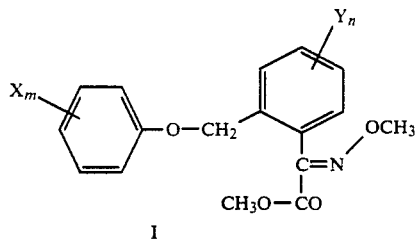

In this process, the 2-phenoxymethylbenzoic acids IV are advantageously converted into their chlorides V (cf. Organikum, VEB Deutscher Verlag der Wissenschaften, 16th edition, Berlin 1986, page 423 et seq.) from which the corresponding benzoyl cyanides VI are then prepared. The benzoyl cyanides VI are then subjected to a Pinner reaction with lower alcohols [cf. Angew. Chemie 94 (1982) 1], resulting in phenylglyoxylic esters VIIb. The compounds VIIa or VIIb, or a mixture of the two, are then reacted with O-methylhydroxylamine or one of its acid addition salts, and the resulting mixture of E and Z isomers is treated, simultaneously or subsequently, with an acid for substantial rearrangement of the Z to the E isomer.

EXAMPLE 3

2-(2-Methylphenoxymethyl)benzoic acid

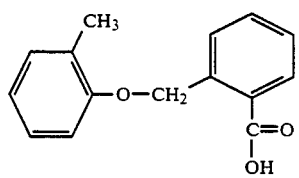

382 g of a 30% by weight solution of sodium methylate in methanol (=2.12 mol of sodium methylate) were rapidly added dropwise to 224 g (2.08 mol) of o-cresol at 35° C., during which the temperature rose to 50° C. The mixture was stirred at this temperature for 1 hour and then 268 g (2 mol) of phthalide were added, after which the methanol was removed by distillation. The resulting melt was heated to 200° C., stirred at this temperature for one hour and then 1.6 l of water were slowly added. The solution obtained after cooling was extracted twice with 0.5 l of toluene each time and then diluted with 1 l of water. The aqueous phase was acidified with concentrated sulfuric acid to pH 2, after which the precipitate was removed, washed with water and dried. Yield: 89%; melting point 154° C.

$^1$H-NMR (in CDCl$_3$; TMS as internal standard): 2.35 ppm (3H), 5.55 ppm (2H), 6.88 ppm (2H), 7.15 ppm (2H), 7.42 ppm (1H), 7.63 ppm (1H), 7.87 ppm (1H) and 8.18 ppm (1H).

EXAMPLE 4

2-Phenoxymethylbenzoic acid

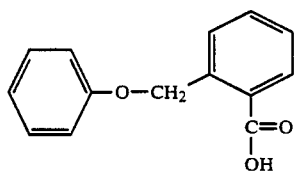

382 g of a 30% by weight solution of sodium methylate in methanol (=2.12 mol of sodium methylate) were rapidly added dropwise to 195.8 g (2.08 mol) of phenol at 45° C., during which the temperature rose to 52° C. The mixture was stirred at 50° C. for 1 hour and then 268 g (2 mol) of phthalide were added, after which the methanol was removed by distillation. The resulting melt was heated to 200° C., stirred at this temperature for one hour and then worked up in a similar manner to Example 1.

Yield: 86%; melting point 132-133° C.

$^1$H-NMR (in CDCl$_3$; TMS as internal standard): 5.55 ppm (2H), 7.00 ppm (3H), 7.30 ppm (2H), 7.40 ppm (1H), 7.65 ppm (1H), 7.85 ppm (1H) and 8.20 ppm (1H).

The present invention furthermore relates to novel o-substituted benzoyl cyanides of the formula VI

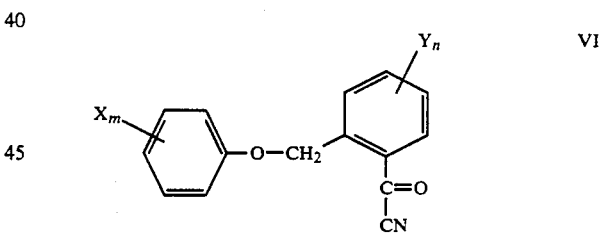

where
X and Y are each halogen, C$_1$-C$_4$-alkyl, C$_1$-C$_4$-alkoxy or trifluoromethyl;
m is an integer from 0 to 4;
n is an integer from 0 to 3.

The present invention also relates to a process for preparing these compounds and to the use thereof as intermediates or preparing 2-methoxyiminoacetic esters of the formula I:

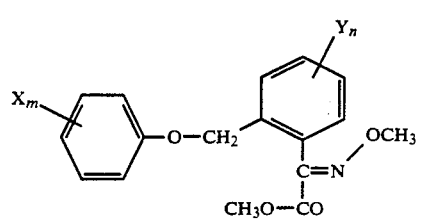

The present invention furthermore relates to novel o-substituted benzoyl chlorides of the formula V'

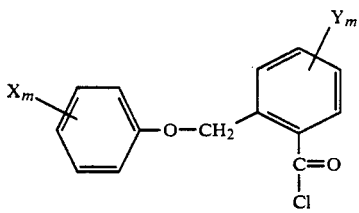

where

X and Y are each halogen, $C_1$-$C_4$-alkyl, $C_1$-$C_4$-alkoxy or trifluoromethyl;

m is an integer from 0 to 4;

n is an integer from 0 to 3, excepting 2-phenoxymethylbenzoyl chloride, 2-(3-n-butylphenoxymethyl)benzoyl chloride, 2-(3-tert-butylphenoxymethyl)benzoyl chloride, 2-(3,4-dimethylphenoxymethyl)benzoyl chloride, 2-(4-sec-butylphenoxymethyl)benzoyl chloride and 2-(4-ethylphenoxymethyl)-4-methoxybenzoyl chloride.

The specific meanings of the variables are as follows: X and Y substitutents selected from a group comprising halogen such as fluorine, chlorine, bromine and iodine, preferably fluorine and chlorine; branched or unbranched $C_1$-$C_4$-alkyl such as methyl, ethyl, n-propyl, isopropyl, n-butyl and tert-butyl, preferably methyl and ethyl; branched or unbranched $C_1$-$C_4$-alkoxy such as methoxy, ethoxy, n-propoxy, isopropoxy and n-butoxy, preferably methoxy, ethoxy, n-propoxy and isopropoxy; trifluoromethyl, m 0, 1, 2, 3 or 4, especially 0, 1, 2 or 3, preferably 0, 1 or 2;

n 0, 1, 2 or 3, especially 0, 1 or 2, preferably 0.

With a view to the properties of the final products, the following o-substituted benzoyl cyanides VI are particularly preferred:
2-phenoxymethylbenzoyl cyanide
2-(2-chlorophenoxymethyl)benzoyl cyanide
2-(3-chlorophenoxymethyl)benzoyl cyanide
2-(4-chlorophenoxymethyl)benzoyl cyanide
2-(2,4-dichlorophenoxymethyl)benzoyl cyanide
2-(2-fluorophenoxymethyl)benzoyl cyanide
2-(3-fluorophenoxymethyl)benzoyl cyanide
2-(4-fluorophenoxymethyl)benzoyl cyanide
2-(2-methylphenoxymethyl)benzoyl cyanide
2-(3-methylphenoxymethyl)benzoyl cyanide
2-(4-methylphenoxymethyl)benzoyl cyanide
2-(2,4-dimethylphenoxymethyl)benzoyl cyanide
2-(2-methyl-4-chlorophenoxymethyl)benzoyl cyanide
2-(2-chloro-4-methylphenoxymethyl)benzoyl cyanide
2-(2-methyl-4-fluorophenoxymethyl)benzoyl cyanide
2-(2-ethylphenoxymethyl)benzoyl cyanide
2-(3-ethylphenoxymethyl)benzoyl cyanide
2-(4-ethylphenoxymethyl)benzoyl cyanide
2-(2-ethyl-4-chlorophenoxymethyl)benzoyl cyanide
2-(2-chloro-4-ethylphenoxymethyl)benzoyl cyanide
2-(2-methyl-4-ethylphenoxymethyl)benzoyl cyanide
2-(2-ethyl-4-methylphenoxymethyl)benzoyl cyanide
2-(2-trifluoromethylphenoxymethyl)benzoyl cyanide
2-(3-trifluoromethylphenoxymethyl)benzoyl cyanide
2-(4-trifluoromethylphenoxymethyl)benzoyl cyanide Particularly preferred benzoyl chlorides V are:
2-(2-chlorophenoxymethyl)benzoyl chloride
2-(3-chlorophenoxymethyl)benzoyl chloride
2-(4-chlorophenoxymethyl)benzoyl chloride
2-(2,4-dichlorophenoxymethyl)benzoyl chloride
2-(2-fluorophenoxymethyl)benzoyl chloride
2-(3-fluorophenoxymethyl)benzoyl chloride
2-(4-fluorophenoxymethyl)benzoyl chloride
2-(2-methylphenoxymethyl)benzoyl chloride
2-(3-methylphenoxymethyl)benzoyl chloride
2-(4-methylphenoxymethyl)benzoyl chloride
2-(2,4-dimethylphenoxymethyl)benzoyl chloride
2-(2-methyl-4-chlorophenoxymethyl)benzoyl chloride
2-(2-chloro-4-methylphenoxymethyl)benzoyl chloride
2-(2-methyl-4-fluorophenoxymethyl)benzoyl chloride
2-(2-ethylphenoxymethyl)benzoyl chloride
2-(3-ethylphenoxymethyl)benzoyl chloride
2-(4-ethylphenoxymethyl)benzoyl chloride .
2-(2-ethyl-4-chlorophenoxymethyl)benzoyl chloride
2-(2-chloro-4-ethylphenoxymethyl)benzoyl chloride
2-(2-methyl-4-ethylphenoxymethyl)benzoyl chloride
2-(2-ethyl-4-methylphenoxymethyl)benzoyl chloride
2-(2-trifluoromethylphenoxymethyl)benzoyl chloride
3-(3-trifluoromethylphenoxymethyl)benzoyl chloride
2-(4-trifluoromethylphenoxymethyl)benzoyl chloride.

Benzoyl cyanides are generally known, eg. from Angew. Chemie 94 (1982) 1.

The benzoyl cyanides VI can be obtained in a variety of ways. They are normally prepared from the corresponding acid chlorides and cyanide salts such as mercury cyanide [Liebig's Annalen 3 (1832) 249], copper cyanide [Organic Synthesis Coll. Vol. III (1955) 112; Angew. Chemie 94 (1982) 1] and, in particular, sodium cyanide using an aqueous/organic two-phase system in the presence of a phase-transfer catalyst [Tetrahedron Letters, (1974) 2275]:

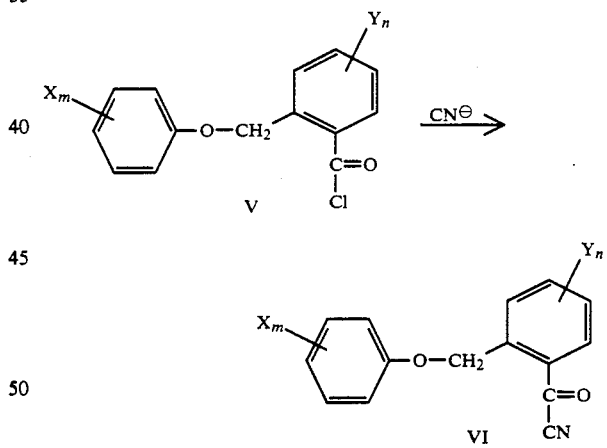

The reaction is normally carried out in an inert solvent or mixture of solvents, in which case the cyanide salt is preferably dissolved in water and the acid chloride V is dissolved in a solvent which is miscible or immiscible with water.

The reaction is particularly preferably carried out in a two-phase system in the presence of a phase-transfer catalyst, eg. a quaternary ammonium or phosphonium salt such as tetrabutylammonium chloride or bromide, methyltributylammonium iodide, tetrabutylammonium bisulfate, trimethylbenzylammonium chloride, triethylbenzylammonium chloride, triphenylbenzylammonium chloride and benzyltributylphosphonium bromide.

Suitable and preferred cyanide salts are alkali metal cyanides such as lithium, sodium and potassium cyanide or alkaline earth metal cyanides such as magnesium, calcium or barium cyanide, especially sodium and potassium cyanide. However, it is also possible to use mixtures of the said salts with hydrocyanic acid.

Examples of suitable inert solvents or diluents for the acid chlorides V are aliphatic hydrocarbons such as n-pentane, n-hexane, cyclohexane, petroleum ether, white oils and naphtha, aromatic hydrocarbons such as benzene, toluene and o-, m- or p-xylene, halohydrocarbons such as methylene chloride, chloroform, tetrachloromethane, 1,2-dichloroethane, 1,1,2-trichloroethane, 1,1,2,2-tetrachloroethane, perchloroethane and chlorobenzene, ethers such as diethyl ether, methyl tert-butyl ether, tetrahydrofuran and dioxane, esters such as ethyl acetate, amides such as dimethylformamide, and dimethyl sulfoxide, sulfolane and N-methylpyrrolidone.

Normally the cyanide salt or the mixture of a cyanide salt in hydrocyanic acid and the acid chloride V are employed in stoichiometric amounts, but an excess of cyanide salt and, where appropriate, hydrocyanic acid, up to about 100 mol %, may also be advantageous.

The amount of phase-transfer catalyst is not critical; normally from 0.001 to 1 mol %, in particular 0.01 to 5 mol %, of catalyst based on the amount of V is used.

The reaction is expediently carried out under atmospheric pressure. Higher or lower pressures are possible but generally have no advantages.

The reaction is generally carried out at from 0° C. to the boiling point of the solvent or mixture thereof, in particular from 0° to 40° C.

The reaction mixture is worked up by conventional methods, so that no details of this need be given.

The reaction can be carried out either batchwise or continuously. When carried out continuously, the reactants are passed, for example, through a tubular reactor or cascades of stirred vessels.

A preferred embodiment comprises adding a solution of the acid chloride to a vigorously stirred mixture of the cyanide salt, or of a cyanide salt in hydrocyanic acid, with the phase-transfer catalyst.

2-Phenoxymethylbenzoyl chloride (V; m, n=0) is disclosed in DE-A 1 279 682.

Furthermore, JP-A 80/124 777 discloses some alkyl-substituted 2-phenoxymethylbenzoyl chlorides as intermediates for 6,11-dihydro-11-oxodibenzo[b,e]oxepines.

The o-substituted benzoyl chlorides of the formula V'

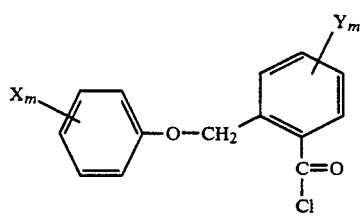

where
X and Y are each halogen, $C_1$-$C_4$-alkyl, $C_1$-$C_4$-alkoxy or trifluoromethyl;
m is an integer from 0 to 4;
n is an integer from 0 to 3,
excepting 2-phenoxymethylbenzoyl chloride,
2-(3-n-butylphenoxymethyl)benzoyl chloride,
2-(3-tert-butylphenoxymethyl)benzoyl chloride,
2-(3,4-dimethylphenoxymethyl)benzoyl chloride,
2-(4-sec-butylphenoxymethyl)benzoyl chloride and
2-(4-ethylphenoxymethyl)-4-methoxybenzoyl chloride, are novel.

They can be obtained by conventional methods by treating the appropriate carboxylic acids IV with phosgene or thionyl chloride, expediently in an inert solvent or diluent (cf. Organikum, VEB Deutscher Verlag der Wissenschaften, 16th Edition, Berlin 1986, pages 423 et seq.).

Examples of suitable solvents or diluents are aliphatic hydrocarbons such as n-pentane, n-hexane, cyclohexane, petroleum ether, white oils and naphtha, aromatic hydrocarbons such as benzene, toluene and o-, m-and p-xylene, halohydrocarbons such as methylene chloride, chloroform, tetrachloromethane, 1,2-dichloroethane, 1,1,2-trichloroethane, 1,1,2,2-tetrachloroethane, perchloroethane and chlorobenzene, ethers such as diethyl ether, tetrahydrofuran and dioxane, esters such as ethyl acetate, and ketones such as acetone, methyl ethyl ketone and cyclohexanone.

Carboxylic acid IV and chlorinating agent are normally employed in stoichiometric amounts, but an excess of up to 100 mol % of chlorinating agent is preferably used.

The reaction is advantageously carried out in the presence of a catalyst, for example an amide such as dimethylformamide, diethylformamide and diisobutylformamide, a tertiary amine such as dimethylaminopyridine, diethylaminopyridine, morpholineformate and 4-pyrrolidinopyridine or a phosphine oxide such as tributylphosphine oxide.

The amount of catalyst can be varied within wide limits. Normally from 0.01 to 50 mol %, in particular 0.1 to 10 mol %, of catalyst based on the amount of acid IV is used.

The temperature for the reaction is not critical, and it is generally carried out at from 0° to 100° C., in particular at the boiling point of the solvent.

The acid chlorides are expediently also prepared under atmospheric pressure. Higher or lower pressures are possible but generally have no advantages.

The reaction mixture is worked up in a conventional way.

The reaction can be carried out either batchwise or continuously. When carried out continuously, the reactants are passed, for example, through a tubular reactor or cascades of stirred vessels.

One variant of the process for preparing the benzoyl cyanides VI comprises synthesizing the benzoyl chlorides V and treating them, without isolating them from the reaction mixture or as crude products, with alkali metal or alkaline earth metal cyanides, if required in the presence of hydrocyanic acid.

The carboxylic acids IV are disclosed in US-A 3 420 851, JP-A 80/124 777 and Coll, Czech. Chem. Commun. 32 (1967) 3448 and can be prepared by the methods described therein. They are particularly advantageously prepared by reacting phenols of the formula II with lactones of the formula III, preferably under basic conditions.

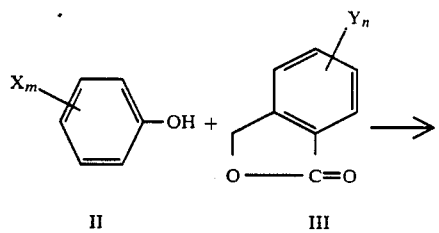

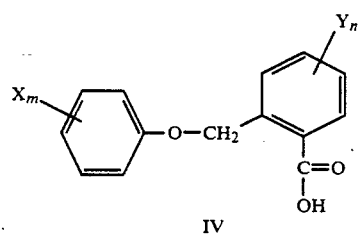

The o-substituted benzoyl cyanides VI are valuable intermediates for the synthesis of E-oxime ethers of phenylglyoxylic esters I which are used in crop protection, preferably as fungicides (cf. EP-A 253 213 and EP-A 254 426).

To prepare the final products I, the o-substituted benzoyl cyanides VI are, either in isolated form, as crude products or still dissolved in the solvent used for their preparation, subjected to a Pinner reaction with lower alcohols such as methanol (cf. Angew. Chemie 94 (1982) 1). This results both in phenylglyoxylic esters VIIa and the acetals of the phenylglyoxylic esters VIIb. The compounds VIIa or VIIb, or a mixture of the two, are subsequently reacted with O-methylhydroxylamine or one of its acid addition salts, and the resulting E/Z isomer mixture is treated, simultaneously or subsequently with an acid for substantial rearrangement of the Z to the E isomer:

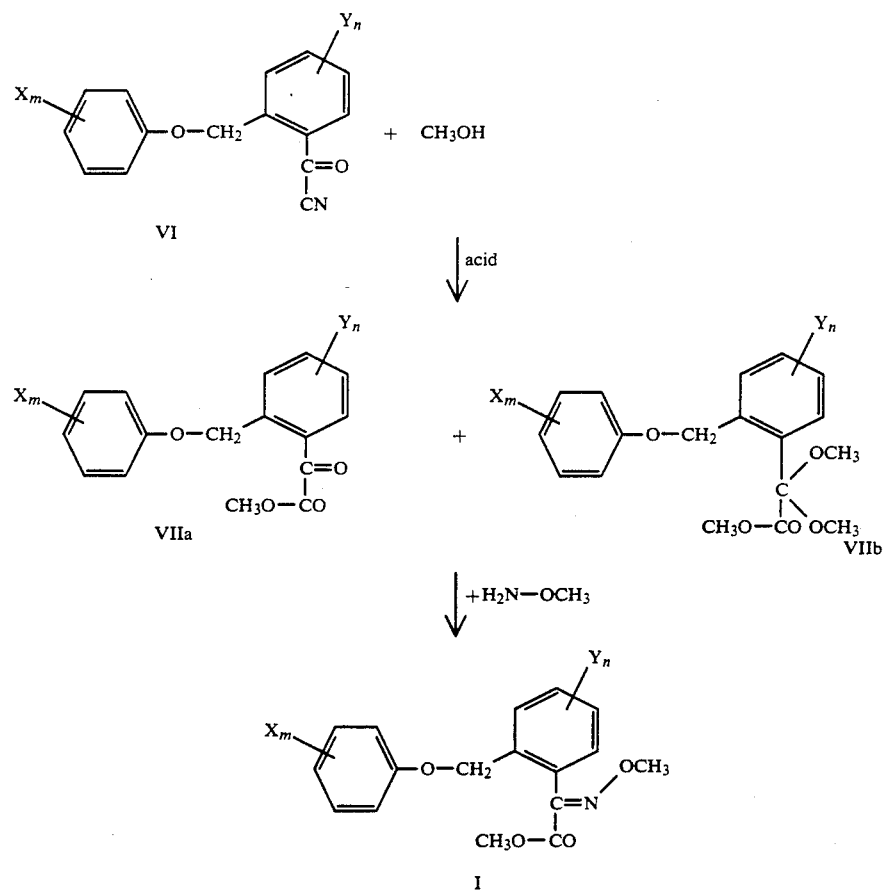

EXAMPLE 5

2-(2-Methylphenoxymethyl)benzoyl cyanide

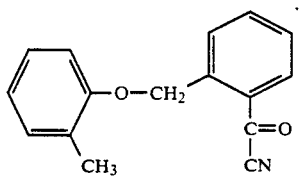

Variant A:

5 890 mg (2.8 mmol) of tetra-n-butylammonium bromide and then a solution of 94.8 g (1.93 mol) of sodium cyanide in 1 l of water were added to a solution of 458 g (1.76 mol) of 2-(2-methylphenoxymethyl)benzoyl chloride in 2 l of toluene. The mixture was stirred at about 20° C. for 2 hours and then left to stand for 14 hours. The organic phase was then separated off, dried over sodium sulfate and concentrated under reduced pressure. The crude brown product had a purity of 91.7% (by GC analysis) and was recrystallized from 2 l of methyl tert-butyl ether. Yield: 61%.

Variant B:

A solution of 231.8 g (0.89 mol) of 2-(2-methylphenoxymethyl)benzoyl chloride in 1.55 l of toluene was added dropwise over the course of one hour to a mixture of 48.2 g (0.98 mol) of sodium cyanide, 2.5 g (7.5 mmol) of tetra-n-butylammonium chloride and 640 ml of water at 22° C. The mixture was then stirred for 14 hours, after which the organic phase was separated off, washed once with 0.5 l of water and concentrated under reduced pressure. The crude product was recrystallized from 0.4 l of cyclohexane. Yield: 67 %. Melting point 74° C. (yellowish brown solid).

Variant C: (reaction in the presence of hydrocyanic acid)

38 g of 19 % by weight aqueous hydrochloric acid (=0.2 mol of HCl) were added dropwise to a solution of 117.4 g (2.4 mol) of sodium cyanide in 725 ml of water at 20° C. 1.4 g (4.3 mmol) of tetrabutylammonium bromide and 2.4 l of toluene were added and then the mixture was heated to 25° C. and, while stirring vigorously, a solution of 521 g (2.0 mol) of 2-(2-methylphenoxymethyl)benzoyl chloride in 710 ml of toluene was added over the course of 15 minutes. The mixture was then stirred for 90 minutes, during which it heated to 32° C. The organic phase was then separated off, washed with 200 ml of water and 200 ml of 1 % by weight aqueous hydrochloric acid and then concentrated under reduced pressure. The pale yellow crude product contained 93 mol % of 2-(2-methylphenoxymethyl)benzoyl cyanide (according to HPLC). Yield: 92.5 %.

$^1$H-NMR (in CDCl$_3$, TMS as internal standard): 2.3 ppm 1 (s,3H); 5.4 ppm (s,2H); 6.7-7.0 ppm (m,2H); 7.1-7.3 ppm (m,2H); 7.6 ppm (t,1H); 7.8 ppm (t,1H); 8.0 ppm (d,1H); 8.3 ppm (d,1H);

IR spectrum [cm$^{-1}$]: 2220, 1665, 1600, 1573, 1496, 1242, 1131, 1060, 746, 724.

Precursor 5.1

2-(2-Methylphenoxymethyl)benzoyl chloride

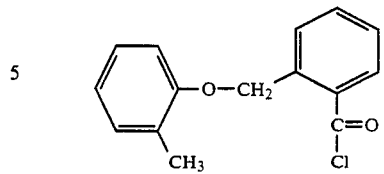

235.6 9 (1.98 mol) of thionyl chloride were added dropwise to a solution of 435 9 (1.80 mol) of 2-(2-methylphenoxymethyl)benzoic acid in 1.8 l of toluene at 20° to 25° C. The resulting mixture was heated at 70° C until evolution of gas ceased (about 5 hours) and was then concentrated. The resulting brown oil (product content 92.5 %) crystallized on cooling. Yield: 93.5 %; melting point 48°-51° C.

$^1$H-NMR (in CDCl$_3$, TMS as internal standard): 2.3 ppm (s,3H); 5.3 ppm (s,2H); 6.7-6.9 ppm (m,2H), 7.0-7.2 ppm (m,2H), 7.4 ppm (t,1H), 7.6 ppm (t,1H), 7.9 ppm (d,1H), 8.3 ppm (d,1H);

IR spectrum [cm$^{-1}$]: 1737, 1495, 1243, 1026, 1185, 1124, 886, 743, 716, 673.

The present invention furthermore relates to a novel process for preparing α-keto carboxylic esters of the formula VIIa

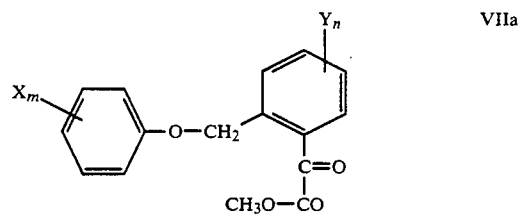

where X and Y are each halogen, C$_1$-C$_4$-alkyl, C$_1$-C$_4$-alkoxy or trifluoromethyl;

m is an integer from 0 to 4;

n is an integer from 0 to 3.

Various processes for preparing aromatic α-keto #esters from the corresponding benzoyl cyanides are described in the literature.

Angew. Chemie 68 (1956) 430 and idem 94 (1982) 1, Org. Synth. 24 (1944) 16 and J. Org. Chem. 29 (1964) 278 describe methods for hydrolyzing benzoyl cyanides with concentrated mineral acids and for converting the resulting keto carboxylic acids into phenylglyoxylic esters, but benzoic esters are formed as by-products:

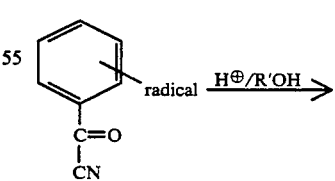

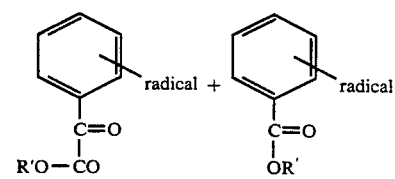

US-A 4 234 739, DE-A 2 708 189 and Tetrah. Lett., (1980) 3539 disclose how the formation of the benzoic esters can in several cases be substantially suppressed by adding a halide.

It is also known to convert benzoyl cyanides either into the corresponding keto tert-butylamides IX by the Ritter reaction (cf. EP-A 034 240) or into keto N-acylamides X (cf. EP-A 35 707). Both compounds can subsequently be converted into keto carboxylic acids and keto esters:

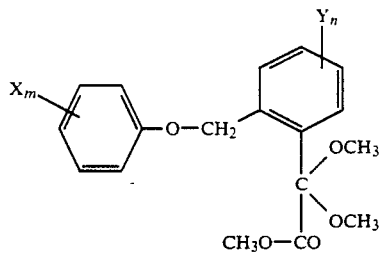
VIIb

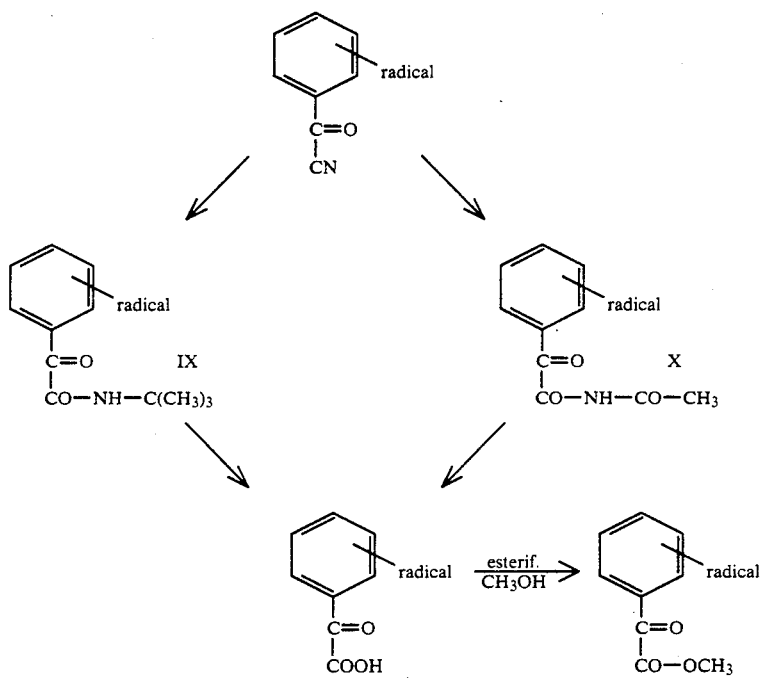

However, it is not possible to prepare the α-keto carboxylic esters VIIa from the benzoyl cyanides VI by said methods. In particular, in this connection it is disclosed in Angew. Chem. 68, (1956) 430 and idem 94 (1982) 10 that the Pinner reaction with benzoyl cyanides at room temperature in an acidic medium in the presence of an alcohol results in the corresponding benzoic esters and not in keto carboxylic esters.

It is an object of the present invention to provide a process for preparing the compounds VIIa from the benzoyl cyanides VI.

We have found that this object is achieved by a novel process for preparing α-keto carboxylic esters VIIa, which comprises a) reacting an o-phenoxymethylbenzoyl cyanide of the formula VI

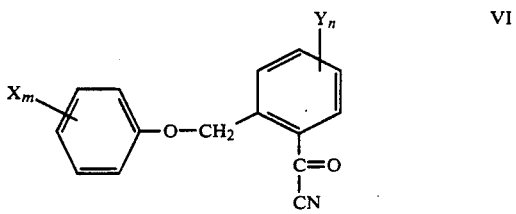
VI with methanol in the presence of an acid, b) if required cleaving the keto carboxylic ester dimethyl acetal byproduct of the formula VIIb under acidic conditions, and, if required, subjecting the alpha-keto carboxamide byproduct of the formula VIIc

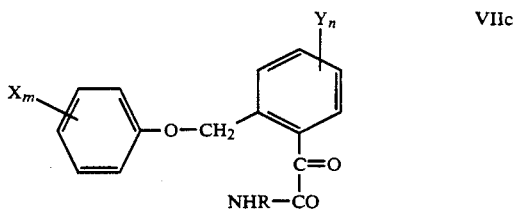
VIIc where R is hydrogen or acyl, to step (a) again.

We have also found novel α-keto carboxamides of the formula VIIc

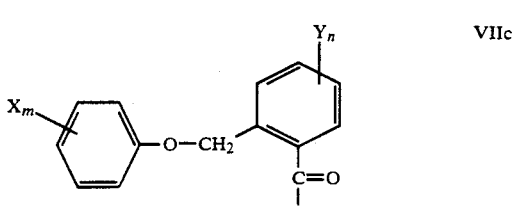
VIIc where

X and Y are each halogen, $C_1$–$C_4$-alkyl, $C_1$–$C_4$-alkoxy or trifluoromethyl;

m is an integer from 0 to 4;

n is an integer from 0 to 3 and R is hydrogen or acyl and novel o-phenoxymethylphenylglyoxylic esters of the formula VIIa′

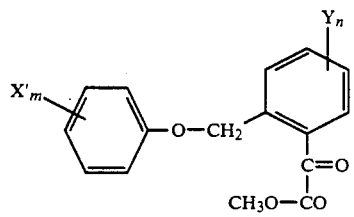

VIIa′ where

X′ and Y are each halogen, $C_1$–$C_4$-alkyl, $C_1$–$C_4$-alkoxy or trifluoromethyl;

m is an integer from 0 to 4;

n is an integer from 0 to 3, with the proviso that n can be 0 only when X′ is 2-chloro, 2-fluoro, 2-methyl, 4-methyl, 4-tert-butyl, 2-methoxy or 2trifluoromethyl and m is 0 or 1, or X′ is 2,4-dichloro or 4-chloro-2-methyl and m is 2, as intermediates.

The o-phenoxymethylbenzoyl cyanides of the formula VI used as starting materials can be obtained, for example, by the following process:

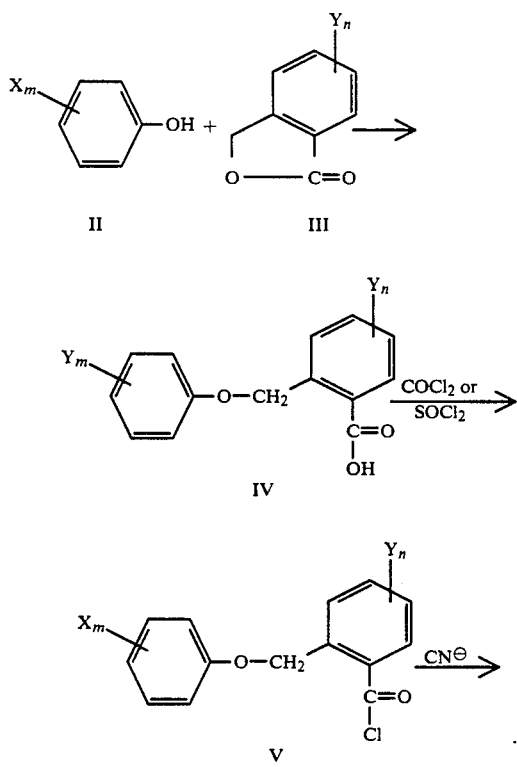

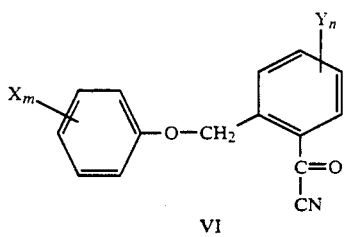

VI

In the first stage of this process, phenols II are reacted with phthalides III, preferably under basic conditions [cf., for example, Coll. Czech. Chem. Commun. 32, (1967) 3448]. The resulting o-(phenoxymethyl)benzoic acids IV are expediently converted into their chlorides V (cf. Organikum, VEB Deutscher Verlag der Wissenschaften, 16th edition, Berlin 1986, page 423 et seq.), and then the o-phenoxymethylbenzoyl cyanides VI are prepared therefrom.

The process according to the invention is normally carried out in an inert solvent or diluent, for example in an ether such as diethyl ether, tetrahydrofuran and dioxane, in a chlorohydrocarbon such as dichloromethane, trichloromethane, tetrachloromethane and dichloroethane, or in an aromatic hydrocarbon such as toluene or o-, m- or p-xylene. The aromatic hydrocarbons, especially toluene and xylene, are preferred.

Suitable acids are mineral acids, especially hydrochloric acid, which is preferably introduced as gas into the solvent.

The process is particularly advantageously carried out in the presence of water or an acylating agent of the formula VIII

where L is halogen, hydroxyl, methoxy or acetyl.

Normally, all the reactants are employed in at least a stoichiometric ratio unless an excess of one of the components, up to about 10 mol%, is advisable. The amount of acid is preferably from 2 to 20 times, in particular about 3 times, the amount of VI. When the reaction is carried out in the presence of water, the molar amount of water is particularly preferably from 1 to 2 times that of VI.

The reaction is generally carried out under atmospheric pressure, advantageously at from −80° to 80° C., in particular −20° to 40° C.

The reaction mixture is worked up in a conventional manner.

Possible byproducts of the process according to the invention are the corresponding keto carboxylic ester dimethyl acetals VIIb of the intermediates VIIa. However, these byproducts do not interfere with the subsequent use of the α-keto carboxylic esters VIIa for the synthesis of E-oxime ethers of phenylglyoxylic esters I

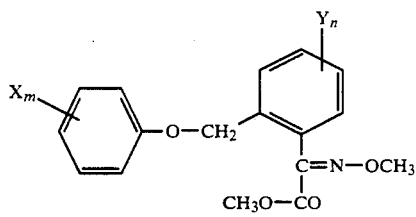

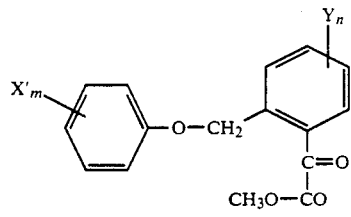

because they are cleaved under the conditions of the subsequent process and also react. However, if required, the keto carboxylic ester dimethyl acetals VIIb can also be converted under acidic conditions, for example by passing in hydrogen chloride in the presence of an inert solvent, into the α-keto carboxylic esters VIIa.

It is furthermore possible in the process according to the invention for the corresponding α-keto carboxamides VIIc of the intermediates VIIa to be formed. If the α-keto carboxamides VIIc are not wanted, the crude product mixture is expediently subjected to the process again, if necessary several times.

However, the methanolysis of the α-keto carboxamides VIIc can also take place in a separate step, for example by treatment of the compounds VIIc with an acid, if required in the presence of a diluent, eg. a hydrocarbon such as toluene, a halohydrocarbon such as dichloromethane, trichloromethane and tetrachloromethane, or an ether such as diethyl ether, diethylene glycol and dioxane.

Examples of suitable acids are mineral acids such as hydrochloric acid, sulfuric acid and phosphoric acid, carboxylic acids such as acetic acid and trifluoroacetic acid or sulfonic acids such as p-toluenesulfonic acid. Preferred acids are sulfuric acid, especially as concentrated aqueous solution, and hydrochloric acid, which is particularly preferably introduced in the form of a gas.

The process according to the invention can be carried out both continuously and batchwise. When carried out continuously, the reactants are passed, for example, through a tubular reactor or a cascade of agitated vessels.

The process according to the invention provides the α-keto carboxylic esters VIIa in high yields with very high purity.

The described method of preparation can be used successfully to synthesize all α-keto carboxylic esters VIIa complying with the definition, especially those compounds where X and Y are each selected from a group comprising:

halogen such as fluorine, chlorine, bromine and iodine, especially fluorine and chlorine;
branched or unbranched $C_1-C_4$-alkyl such as methyl, ethyl, n-propyl, isopropyl, isobutyl, sec-butyl and n-butyl; especially methyl and ethyl;
branched or unbranched $C_1-C_4$-alkoxy such as methoxy, ethoxy, 1-methylethoxy, isopropoxy, n-butoxy, isobutoxy, and sec-butoxy n-propoxy;
trifluoromethyl;
m is 0, 1, 2, 3 or 4, especially 0, 1 or 2;
n is 0, 1, 2 or 3, especially 0 or 1.

o-Phenoxymethylphenylglyoxylic esters of the formula VIIa, where X' and Y are each halogen, $C_1-C_4$-alkyl, $C_1-C_4$-alkoxy or trifluoromethyl;
m is an integer from 0 to 4;
n is an integer from 0 to 3,
with the proviso that n can be 0 only when X' is 2-chloro, 2-fluoro, 2-methyl, 4-methyl, 4-tert-butyl, 2-methoxy or 2-trifluoromethyl and m is 0 or 1, or X' is 2,4-dichloro or 4-chloro-2-methyl and m is 2, are novel.

Likewise novel are the α-keto carboxamides of the formula VIIc

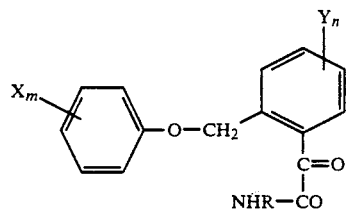

where X and Y each halogen, $C_1-C_4$-alkyl, $C_1-C_4$-alkoxy or trifluoromethyl;
m is an integer from 0 to 4;
n is an integer from 0 to 3 and
R is hydrogen or acyl.

Particularly suitable methyl α-keto carboxylates VIIa and preferred novel α-keto carboxamides VIIc are to be found in Table 1.

TABLE 1

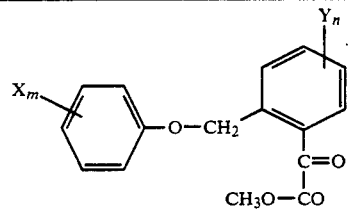

VIIa

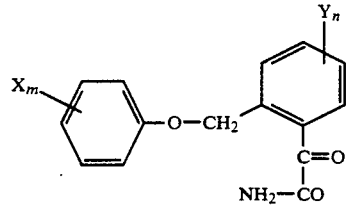

VIIc

| No. | X | m | Y | n |
|---|---|---|---|---|
| 1.001 | — | 0 | — | 0 |
| 1.002 | 2-F | 1 | — | 0 |
| 1.003 | 2-Cl | 1 | — | 0 |
| 1.004 | 3-Cl | 1 | — | 0 |
| 1.005 | 4-Cl | 1 | — | 0 |
| 1.006 | 2,4-Cl$_2$ | 2 | — | 0 |
| 1.007 | 2-CH$_3$, 4-Cl | 2 | — | 0 |
| 1.008 | 2-CH$_3$ | 1 | — | 0 |
| 1.009 | 4-CH$_3$ | 1 | — | 0 |
| 1.010 | 4-tert. C$_4$H$_9$ | 1 | — | 0 |
| 1.011 | — | — | 3-F | 1 |

TABLE 1-continued

| | | | | |
|---|---|---|---|---|
| 1.012 | 2-F | 1 | 3-F | 1 |
| 1.013 | 3-F | 1 | 3-F | 1 |
| 1.014 | 4-F | 1 | 3-F | 1 |
| 1.015 | 2-Cl | 1 | 3-F | 1 |
| 1.016 | 3-Cl | 1 | 3-F | 1 |
| 1.017 | 4-Cl | 1 | 3-F | 1 |
| 1.018 | 2-CH$_3$ | 1 | 3-F | 1 |
| 1.019 | 3-CH$_3$ | 1 | 3-F | 1 |
| 1.020 | 4-CH$_3$ | 1 | 3-F | 1 |
| 1.021 | 2-OCH$_3$ | 1 | 3-F | 1 |
| 1.022 | 3-OCH$_3$ | 1 | 3-F | 1 |
| 1.023 | 4-OCH$_3$ | 1 | 3-F | 1 |
| 1.024 | 2-CF$_3$ | 1 | 3-F | 1 |
| 1.025 | 3-CF$_3$ | 1 | 3-F | 1 |
| 1.026 | 4-CF$_3$ | 1 | 3-F | 1 |
| 1.027 | 2,3-Cl$_2$ | 2 | 3-F | 1 |
| 1.028 | 2,4-Cl$_2$ | 2 | 3-F | 1 |
| 1.029 | 2,5-Cl$_2$ | 2 | 3-F | 1 |
| 1.030 | 2,6-Cl$_2$ | 2 | 3-F | 1 |
| 1.031 | 3,4-Cl$_2$ | 2 | 3-F | 1 |
| 1.032 | 3,5-Cl$_2$ | 2 | 3-F | 1 |
| 1.033 | 2-CH$_3$, 4-Cl | 2 | 3-F | 1 |
| 1.034 | 2-Cl, 4-CH$_3$ | 2 | 3-F | 1 |
| 1.035 | 2-CF$_3$, 4-CH$_3$ | 2 | 3-F | 1 |
| 1.036 | 2-CH$_3$, 4-CF$_3$ | 2 | 3-F | 1 |
| 1.037 | — | — | 3-Cl | 1 |
| 1.038 | 2-F | 1 | 3-Cl | 1 |
| 1.039 | 3-F | 1 | 3-Cl | 1 |
| 1.040 | 4-F | 1 | 3-Cl | 1 |
| 1.041 | 2-Cl | 1 | 3-Cl | 1 |
| 1.042 | 3-Cl | 1 | 3-Cl | 1 |
| 1.043 | 4-Cl | 1 | 3-Cl | 1 |
| 1.044 | 2-CH$_3$ | 1 | 3-Cl | 1 |
| 1.045 | 3-CH$_3$ | 1 | 3-Cl | 1 |
| 1.046 | 4-CH$_3$ | 1 | 3-Cl | 1 |
| 1.047 | 2-OCH$_3$ | 1 | 3-Cl | 1 |
| 1.048 | 3-OCH$_3$ | 1 | 3-Cl | 1 |
| 1.049 | 4-OCH$_3$ | 1 | 3-Cl | 1 |
| 1.050 | 2-CF$_3$ | 1 | 3-Cl | 1 |
| 1.051 | 3-CF$_3$ | 1 | 3-Cl | 1 |
| 1.052 | 4-CF$_3$ | 1 | 3-Cl | 1 |
| 1.053 | 2,3-Cl$_2$ | 2 | 3-Cl | 1 |
| 1.054 | 2,4-Cl$_2$ | 2 | 3-Cl | 1 |
| 1.055 | 2,5-Cl$_2$ | 2 | 3-Cl | 1 |
| 1.056 | 2,6-Cl$_2$ | 2 | 3-Cl | 1 |
| 1.057 | 3,4-Cl$_2$ | 2 | 3-Cl | 1 |
| 1.058 | 3,5-Cl$_2$ | 2 | 3-Cl | 1 |
| 1.059 | 2-CH$_3$, 4-Cl | 2 | 3-Cl | 1 |
| 1.060 | 2-Cl, 4-CH$_3$ | 2 | 3-Cl | 1 |
| 1.061 | 2-CF$_3$, 4-CH$_3$ | 2 | 3-Cl | 1 |
| 1.062 | 2-CH$_3$, 4-CF$_3$ | 2 | 3-Cl | 1 |
| 1.063 | — | — | 3-CH$_3$ | 1 |
| 1.064 | 2-F | 1 | 3-CH$_3$ | 1 |
| 1.065 | 3-F | 1 | 3-CH$_3$ | 1 |
| 1.066 | 4-F | 1 | 3-CH$_3$ | 1 |
| 1.067 | 2-Cl | 1 | 3-CH$_3$ | 1 |
| 1.068 | 3-Cl | 1 | 3-CH$_3$ | 1 |
| 1.069 | 4-Cl | 1 | 3-CH$_3$ | 1 |
| 1.070 | 2-CH$_3$ | 1 | 3-CH$_3$ | 1 |
| 1.071 | 3-CH$_3$ | 1 | 3-CH$_3$ | 1 |
| 1.072 | 4-CH$_3$ | 1 | 3-CH$_3$ | 1 |
| 1.073 | 2-OCH$_3$ | 1 | 3-CH$_3$ | 1 |
| 1.074 | 3-OCH$_3$ | 1 | 3-CH$_3$ | 1 |
| 1.075 | 4-OCH$_3$ | 1 | 3-CH$_3$ | 1 |
| 1.076 | 2-CF$_3$ | 1 | 3-CH$_3$ | 1 |
| 1.077 | 3-CF$_3$ | 1 | 3-CH$_3$ | 1 |
| 1.078 | 4-CF$_3$ | 1 | 3-CH$_3$ | 1 |
| 1.079 | 2,3-Cl$_2$ | 2 | 3-CH$_3$ | 1 |
| 1.080 | 2,4-Cl$_2$ | 2 | 3-CH$_3$ | 1 |
| 1.081 | 2,5-Cl$_2$ | 2 | 3-CH$_3$ | 1 |
| 1.082 | 2,6-Cl$_2$ | 2 | 3-CH$_3$ | 1 |
| 1.083 | 3,4-Cl$_2$ | 2 | 3-CH$_3$ | 1 |
| 1.084 | 3,5-Cl$_2$ | 2 | 3-CH$_3$ | 1 |
| 1.085 | 2-CH$_3$, 4-Cl | 2 | 3-CH$_3$ | 1 |
| 1.086 | 2-Cl, 4-CH$_3$ | 2 | 3-CH$_3$ | 1 |
| 1.087 | 2-CF$_3$, 4-CH$_3$ | 2 | 3-CH$_3$ | 1 |
| 1.088 | 2-CH$_3$, 4-CF$_3$ | 2 | 3-CH$_3$ | 1 |
| 1.089 | — | — | 3-OCH$_3$ | 1 |
| 1.090 | 2-F | 1 | 3-OCH$_3$ | 1 |
| 1.091 | 3-F | 1 | 3-OCH$_3$ | 1 |
| 1.092 | 4-F | 1 | 3-OCH$_3$ | 1 |
| 1.093 | 2-Cl | 1 | 3-OCH$_3$ | 1 |
| 1.094 | 3-Cl | 1 | 3-OCH$_3$ | 1 |
| 1.095 | 4-Cl | 1 | 3-OCH$_3$ | 1 |
| 1.096 | 2-CH$_3$ | 1 | 3-OCH$_3$ | 1 |
| 1.097 | 3-CH$_3$ | 1 | 3-OCH$_3$ | 1 |
| 1.098 | 4-CH$_3$ | 1 | 3-OCH$_3$ | 1 |
| 1.099 | 2-OCH$_3$ | 1 | 3-OCH$_3$ | 1 |
| 1.100 | 3-OCH$_3$ | 1 | 3-OCH$_3$ | 1 |
| 1.101 | 4-OCH$_3$ | 1 | 3-OCH$_3$ | 1 |
| 1.102 | 2-CF$_3$ | 1 | 3-OCH$_3$ | 1 |
| 1.103 | 3-CF$_3$ | 1 | 3-OCH$_3$ | 1 |
| 1.104 | 4-CF$_3$ | 1 | 3-OCH$_3$ | 1 |
| 1.105 | 2,3-Cl$_2$ | 2 | 3-OCH$_3$ | 1 |
| 1.106 | 2,4-Cl$_2$ | 2 | 3-OCH$_3$ | 1 |
| 1.107 | 2,5-Cl$_2$ | 2 | 3-OCH$_3$ | 1 |
| 1.108 | 2,6-Cl$_2$ | 2 | 3-OCH$_3$ | 1 |
| 1.109 | 3,4-Cl$_2$ | 2 | 3-OCH$_3$ | 1 |
| 1.110 | 3,5-Cl$_2$ | 2 | 3-OCH$_3$ | 1 |
| 1.111 | 2-CH$_3$, 4-Cl | 2 | 3-OCH$_3$ | 1 |
| 1.112 | 2-Cl, 4-CH$_3$ | 2 | 3-OCH$_3$ | 1 |
| 1.113 | 2-CF$_3$, 4-CH$_3$ | 2 | 3-OCH$_3$ | 1 |
| 1.114 | 2-CH$_3$, 4-CF$_3$ | 2 | 3-OCH$_3$ | 1 |
| 1.115 | — | — | 3-CF$_3$ | 1 |
| 1.116 | 2-F | 1 | 3-CF$_3$ | 1 |
| 1.117 | 3-F | 1 | 3-CF$_3$ | 1 |
| 1.118 | 4-F | 1 | 3-CF$_3$ | 1 |
| 1.119 | 2-Cl | 1 | 3-CF$_3$ | 1 |
| 1.120 | 3-Cl | 1 | 3-CF$_3$ | 1 |
| 1.121 | 4-Cl | 1 | 3-CF$_3$ | 1 |
| 1.122 | 2-CH$_3$ | 1 | 3-CF$_3$ | 1 |
| 1.123 | 3-CH$_3$ | 1 | 3-CF$_3$ | 1 |
| 1.124 | 4-CH$_3$ | 1 | 3-CF$_3$ | 1 |
| 1.125 | 2-OCH$_3$ | 1 | 3-CF$_3$ | 1 |
| 1.126 | 3-OCH$_3$ | 1 | 3-CF$_3$ | 1 |
| 1.127 | 4-OCH$_3$ | 1 | 3-CF$_3$ | 1 |
| 1.128 | 2-CF$_3$ | 1 | 3-CF$_3$ | 1 |
| 1.129 | 3-CF$_3$ | 1 | 3-CF$_3$ | 1 |
| 1.130 | 4-CF$_3$ | 1 | 3-CF$_3$ | 1 |
| 1.131 | 2,3-Cl$_2$ | 2 | 3-CF$_3$ | 1 |
| 1.132 | 2,4-Cl$_2$ | 2 | 3-CF$_3$ | 1 |
| 1.133 | 2,5-Cl$_2$ | 2 | 3-CF$_3$ | 1 |
| 1.134 | 2,6-Cl$_2$ | 2 | 3-CF$_3$ | 1 |
| 1.135 | 3,4-Cl$_2$ | 2 | 3-CF$_3$ | 1 |
| 1.136 | 3,5-Cl$_2$ | 2 | 3-CF$_3$ | 1 |
| 1.137 | 2-CH$_3$, 4-Cl | 2 | 3-CF$_3$ | 1 |
| 1.138 | 2-Cl, 4-CH$_3$ | 2 | 3-CF$_3$ | 1 |
| 1.139 | 2-CF$_3$, 4-CH$_3$ | 2 | 3-CF$_3$ | 1 |
| 1.140 | 2-CH$_3$, 4-CF$_3$ | 2 | 3-CF$_3$ | 1 |
| 1.141 | — | — | 4-F | 1 |
| 1.142 | 2-F | 1 | 4-F | 1 |
| 1.143 | 3-F | 1 | 4-F | 1 |
| 1.144 | 4-F | 1 | 4-F | 1 |
| 1.145 | 2-Cl | 1 | 4-F | 1 |
| 1.146 | 3-Cl | 1 | 4-F | 1 |
| 1.147 | 4-Cl | 1 | 4-F | 1 |
| 1.148 | 2-CH$_3$ | 1 | 4-F | 1 |
| 1.149 | 3-CH$_3$ | 1 | 4-F | 1 |
| 1.150 | 4-CH$_3$ | 1 | 4-F | 1 |
| 1.151 | 2-OCH$_3$ | 1 | 4-F | 1 |
| 1.152 | 3-OCH$_3$ | 1 | 4-F | 1 |
| 1.153 | 4-OCH$_3$ | 1 | 4-F | 1 |
| 1.154 | 2-CF$_3$ | 1 | 4-F | 1 |
| 1.155 | 3-CF$_3$ | 1 | 4-F | 1 |
| 1.156 | 4-CF$_3$ | 1 | 4-F | 1 |
| 1.157 | 2,3-Cl$_2$ | 2 | 4-F | 1 |
| 1.158 | 2,4-Cl$_2$ | 2 | 4-F | 1 |
| 1.159 | 2,5-Cl$_2$ | 2 | 4-F | 1 |
| 1.160 | 2,6-Cl$_2$ | 2 | 4-F | 1 |
| 1.161 | 3,4-Cl$_2$ | 2 | 4-F | 1 |
| 1.162 | 3,5-Cl$_2$ | 2 | 4-F | 1 |
| 1.163 | 2-CH$_3$, 4-Cl | 2 | 4-F | 1 |
| 1.164 | 2-Cl, 4-CH$_3$ | 2 | 4-F | 1 |
| 1.165 | 2-CF$_3$, 4-CH$_3$ | 2 | 4-F | 1 |
| 1.166 | 2-CH$_3$, 4-CF$_3$ | 2 | 4-F | 1 |
| 1.167 | — | — | 4-Cl | 1 |
| 1.168 | 2-F | 1 | 4-Cl | 1 |
| 1.169 | 3-F | 1 | 4-Cl | 1 |
| 1.170 | 4-F | 1 | 4-Cl | 1 |
| 1.171 | 2-Cl | 1 | 4-Cl | 1 |
| 1.172 | 3-Cl | 1 | 4-Cl | 1 |
| 1.173 | 4-Cl | 1 | 4-Cl | 1 |
| 1.174 | 2-CH$_3$ | 1 | 4-Cl | 1 |
| 1.175 | 3-CH$_3$ | 1 | 4-Cl | 1 |

TABLE 1-continued

| | | | | |
|---|---|---|---|---|
| 1.176 | 4-CH$_3$ | 1 | 4-Cl | 1 |
| 1.177 | 2-OCH$_3$ | 1 | 4-Cl | 1 |
| 1.178 | 3-OCH$_3$ | 1 | 4-Cl | 1 |
| 1.179 | 4-OCH$_3$ | 1 | 4-Cl | 1 |
| 1.180 | 2-CF$_3$ | 1 | 4-Cl | 1 |
| 1.181 | 3-CF$_3$ | 1 | 4-Cl | 1 |
| 1.182 | 4-CF$_3$ | 1 | 4-Cl | 1 |
| 1.183 | 2,3-Cl$_2$ | 2 | 4-Cl | 1 |
| 1.184 | 2,4-Cl$_2$ | 2 | 4-Cl | 1 |
| 1.185 | 2,5-Cl$_2$ | 2 | 4-Cl | 1 |
| 1.186 | 2,6-Cl$_2$ | 2 | 4-Cl | 1 |
| 1.187 | 3,4-Cl$_2$ | 2 | 4-Cl | 1 |
| 1.188 | 3,5-Cl$_2$ | 2 | 4-Cl | 1 |
| 1.189 | 2-CH$_3$, 4-Cl | 2 | 4-Cl | 1 |
| 1.190 | 2-Cl, 4-CH$_3$ | 2 | 4-Cl | 1 |
| 1.191 | 2-CF$_3$, 4-CH$_3$ | 2 | 4-Cl | 1 |
| 1.192 | 2-CH$_3$, 4-CF$_3$ | 2 | 4-Cl | 1 |
| 1.193 | — | — | 4-Me | 1 |
| 1.194 | 2-F | 1 | 4-Me | 1 |
| 1.195 | 3-F | 1 | 4-Me | 1 |
| 1.196 | 4-F | 1 | 4-Me | 1 |
| 1.197 | 2-Cl | 1 | 4-Me | 1 |
| 1.198 | 3-Cl | 1 | 4-Me | 1 |
| 1.199 | 4-Cl | 1 | 4-Me | 1 |
| 1.200 | 2-CH$_3$ | 1 | 4-Me | 1 |
| 1.201 | 3-CH$_3$ | 1 | 4-Me | 1 |
| 1.202 | 4-CH$_3$ | 1 | 4-Me | 1 |
| 1.203 | 2-OCH$_3$ | 1 | 4-Me | 1 |
| 1.204 | 3-OCH$_3$ | 1 | 4-Me | 1 |
| 1.205 | 4-OCH$_3$ | 1 | 4-Me | 1 |
| 1.206 | 2-CF$_3$ | 1 | 4-Me | 1 |
| 1.207 | 3-CF$_3$ | 1 | 4-Me | 1 |
| 1.208 | 4-CF$_3$ | 1 | 4-Me | 1 |
| 1.209 | 2,3-Cl$_2$ | 2 | 4-Me | 1 |
| 1.210 | 2,4-Cl$_2$ | 2 | 4-Me | 1 |
| 1.211 | 2,5-Cl$_2$ | 2 | 4-Me | 1 |
| 1.212 | 2,6-Cl$_2$ | 2 | 4-Me | 1 |
| 1.213 | 3,4-Cl$_2$ | 2 | 4-Me | 1 |
| 1.214 | 3,5-Cl$_2$ | 2 | 4-Me | 1 |
| 1.215 | 2-CH$_3$, 4-Cl | 2 | 4-Me | 1 |
| 1.216 | 2-Cl, 4-CH$_3$ | 2 | 4-Me | 1 |
| 1.217 | 2-CF$_3$, 4-CH$_3$ | 2 | 4-Me | 1 |
| 1.218 | 2-CH$_3$, 4-CF$_3$ | 2 | 4-Me | 1 |
| 1.219 | — | — | 4-OCH$_3$ | 1 |
| 1.220 | 2-F | 1 | 4-OCH$_3$ | 1 |
| 1.221 | 3-F | 1 | 4-OCH$_3$ | 1 |
| 1.222 | 4-F | 1 | 4-OCH$_3$ | 1 |
| 1.223 | 2-Cl | 1 | 4-OCH$_3$ | 1 |
| 1.224 | 3-Cl | 1 | 4-OCH$_3$ | 1 |
| 1.225 | 4-Cl | 1 | 4-OCH$_3$ | 1 |
| 1.226 | 2-CH$_3$ | 1 | 4-OCH$_3$ | 1 |
| 1.227 | 3-CH$_3$ | 1 | 4-OCH$_3$ | 1 |
| 1.228 | 4-CH$_3$ | 1 | 4-OCH$_3$ | 1 |
| 1.229 | 2-OCH$_3$ | 1 | 4-OCH$_3$ | 1 |
| 1.230 | 3-OCH$_3$ | 1 | 4-OCH$_3$ | 1 |
| 1.231 | 4-OCH$_3$ | 1 | 4-OCH$_3$ | 1 |
| 1.232 | 2-CF$_3$ | 1 | 4-OCH$_3$ | 1 |
| 1.233 | 3-CF$_3$ | 1 | 4-OCH$_3$ | 1 |
| 1.234 | 4-CF$_3$ | 1 | 4-OCH$_3$ | 1 |
| 1.235 | 2,3-Cl$_2$ | 2 | 4-OCH$_3$ | 1 |
| 1.236 | 2,4-Cl$_2$ | 2 | 4-OCH$_3$ | 1 |
| 1.237 | 2,5-Cl$_2$ | 2 | 4-OCH$_3$ | 1 |
| 1.238 | 2,6-Cl$_2$ | 2 | 4-OCH$_3$ | 1 |
| 1.239 | 3,4-Cl$_2$ | 2 | 4-OCH$_3$ | 1 |
| 1.240 | 3,5-Cl$_2$ | 2 | 4-OCH$_3$ | 1 |
| 1.241 | 2-CH$_3$, 4-Cl | 2 | 4-OCH$_3$ | 1 |
| 1.242 | 2-Cl, 4-CH$_3$ | 2 | 4-OCH$_3$ | 1 |
| 1.243 | 2-CF$_3$, 4-CH$_3$ | 2 | 4-OCH$_3$ | 1 |
| 1.244 | 2-CH$_3$, 4-CF$_3$ | 2 | 4-OCH$_3$ | 1 |
| 1.245 | — | — | 4-CF$_3$ | 1 |
| 1.246 | 2-F | 1 | 4-CF$_3$ | 1 |
| 1.247 | 3-F | 1 | 4-CF$_3$ | 1 |
| 1.248 | 4-F | 1 | 4-CF$_3$ | 1 |
| 1.249 | 2-Cl | 1 | 4-CF$_3$ | 1 |
| 1.250 | 3-Cl | 1 | 4-CF$_3$ | 1 |
| 1.251 | 4-Cl | 1 | 4-CF$_3$ | 1 |
| 1.252 | 2-CH$_3$ | 1 | 4-CF$_3$ | 1 |
| 1.253 | 3-CH$_3$ | 1 | 4-CF$_3$ | 1 |
| 1.254 | 4-CH$_3$ | 1 | 4-CF$_3$ | 1 |
| 1.255 | 2-OCH$_3$ | 1 | 4-CF$_3$ | 1 |
| 1.256 | 3-OCH$_3$ | 1 | 4-CF$_3$ | 1 |
| 1.257 | 4-OCH$_3$ | 1 | 4-CF$_3$ | 1 |
| 1.258 | 2-CF$_3$ | 1 | 4-CF$_3$ | 1 |
| 1.259 | 3-CF$_3$ | 1 | 4-CF$_3$ | 1 |
| 1.260 | 4-CF$_3$ | 1 | 4-CF$_3$ | 1 |
| 1.261 | 2,3-Cl$_2$ | 2 | 4-CF$_3$ | 1 |
| 1.262 | 2,4-Cl$_2$ | 2 | 4-CF$_3$ | 1 |
| 1.263 | 2,5-Cl$_2$ | 2 | 4-CF$_3$ | 1 |
| 1.264 | 2,6-Cl$_2$ | 2 | 4-CF$_3$ | 1 |
| 1.265 | 3,4-Cl$_2$ | 2 | 4-CF$_3$ | 1 |
| 1.266 | 3,5-Cl$_2$ | 2 | 4-CF$_3$ | 1 |
| 1.267 | 2-CH$_3$, 4-Cl | 2 | 4-CF$_3$ | 1 |
| 1.268 | 2-Cl, 4-CH$_3$ | 2 | 4-CF$_3$ | 1 |
| 1.269 | 2-CF$_3$, 4-CH$_3$ | 2 | 4-CF$_3$ | 1 |
| 1.270 | 2-CH$_3$, 4-CF$_3$ | 2 | 4-CF$_3$ | 1 |
| 1.271 | — | — | 5-F | 1 |
| 1.272 | 2-F | 1 | 5-F | 1 |
| 1.273 | 3-F | 1 | 5-F | 1 |
| 1.274 | 4-F | 1 | 5-F | 1 |
| 1.275 | 2-Cl | 1 | 5-F | 1 |
| 1.276 | 3-Cl | 1 | 5-F | 1 |
| 1.277 | 4-Cl | 1 | 5-F | 1 |
| 1.278 | 2-CH$_3$ | 1 | 5-F | 1 |
| 1.279 | 3-CH$_3$ | 1 | 5-F | 1 |
| 1.280 | 4-CH$_3$ | 1 | 5-F | 1 |
| 1.281 | 2-OCH$_3$ | 1 | 5-F | 1 |
| 1.282 | 3-OCH$_3$ | 1 | 5-F | 1 |
| 1.283 | 4-OCH$_3$ | 1 | 5-F | 1 |
| 1.284 | 2-CF$_3$ | 1 | 5-F | 1 |
| 1.285 | 3-CF$_3$ | 1 | 5-F | 1 |
| 1.286 | 4-CF$_3$ | 1 | 5-F | 1 |
| 1.287 | 2,3-Cl$_2$ | 2 | 5-F | 1 |
| 1.288 | 2,4-Cl$_2$ | 2 | 5-F | 1 |
| 1.289 | 2,5-Cl$_2$ | 2 | 5-F | 1 |
| 1.290 | 2,6-Cl$_2$ | 2 | 5-F | 1 |
| 1.291 | 3,4-Cl$_2$ | 2 | 5-F | 1 |
| 1.292 | 3,5-Cl$_2$ | 2 | 5-F | 1 |
| 1.293 | 2-CH$_3$, 4-Cl | 2 | 5-F | 1 |
| 1.294 | 2-Cl, 4-CH$_3$ | 2 | 5-F | 1 |
| 1.295 | 2-CF$_3$, 4-CH$_3$ | 2 | 5-F | 1 |
| 1.296 | 2-CH$_3$, 4-CF$_3$ | 2 | 5-F | 1 |
| 1.297 | — | — | 5-Cl | 1 |
| 1.298 | 2-F | 1 | 5-Cl | 1 |
| 1.299 | 3-F | 1 | 5-Cl | 1 |
| 1.300 | 4-F | 1 | 5-Cl | 1 |
| 1.301 | 2-Cl | 1 | 5-Cl | 1 |
| 1.302 | 3-Cl | 1 | 5-Cl | 1 |
| 1.303 | 4-Cl | 1 | 5-Cl | 1 |
| 1.304 | 2-CH$_3$ | 1 | 5-Cl | 1 |
| 1.305 | 3-CH$_3$ | 1 | 5-Cl | 1 |
| 1.306 | 4-CH$_3$ | 1 | 5-Cl | 1 |
| 1.307 | 2-OCH$_3$ | 1 | 5-Cl | 1 |
| 1.308 | 3-OCH$_3$ | 1 | 5-Cl | 1 |
| 1.309 | 4-OCH$_3$ | 1 | 5-Cl | 1 |
| 1.310 | 2-CF$_3$ | 1 | 5-Cl | 1 |
| 1.311 | 3-CF$_3$ | 1 | 5-Cl | 1 |
| 1.312 | 4-CF$_3$ | 1 | 5-Cl | 1 |
| 1.313 | 2,3-Cl$_2$ | 2 | 5-Cl | 1 |
| 1.314 | 2,4-Cl$_2$ | 2 | 5-Cl | 1 |
| 1.315 | 2,5-Cl$_2$ | 2 | 5-Cl | 1 |
| 1.316 | 2,6-Cl$_2$ | 2 | 5-Cl | 1 |
| 1.317 | 3,4-Cl$_2$ | 2 | 5-Cl | 1 |
| 1.318 | 3,5-Cl$_2$ | 2 | 5-Cl | 1 |
| 1.319 | 2-CH$_3$, 4-Cl | 2 | 5-Cl | 1 |
| 1.320 | 2-Cl, 4-CH$_3$ | 2 | 5-Cl | 1 |
| 1.321 | 2-CF$_3$, 4-CH$_3$ | 2 | 5-Cl | 1 |
| 1.322 | 2-CH$_3$, 4-CF$_3$ | 2 | 5-Cl | 1 |
| 1.323 | — | — | 5-Me | 1 |
| 1.324 | 2-F | 1 | 5-Me | 1 |
| 1.325 | 3-F | 1 | 5-Me | 1 |
| 1.326 | 4-F | 1 | 5-Me | 1 |
| 1.327 | 2-Cl | 1 | 5-Me | 1 |
| 1.328 | 3-Cl | 1 | 5-Me | 1 |
| 1.329 | 4-Cl | 1 | 5-Me | 1 |
| 1.330 | 2-CH$_3$ | 1 | 5-Me | 1 |
| 1.331 | 3-CH$_3$ | 1 | 5-Me | 1 |
| 1.332 | 4-CH$_3$ | 1 | 5-Me | 1 |
| 1.333 | 2-OCH$_3$ | 1 | 5-Me | 1 |
| 1.334 | 3-OCH$_3$ | 1 | 5-Me | 1 |
| 1.335 | 4-OCH$_3$ | 1 | 5-Me | 1 |
| 1.336 | 2-CF$_3$ | 1 | 5-Me | 1 |
| 1.337 | 3-CF$_3$ | 1 | 5-Me | 1 |
| 1.338 | 4-CF$_3$ | 1 | 5-Me | 1 |
| 1.339 | 2,3-Cl$_2$ | 2 | 5-Me | 1 |

TABLE 1-continued

| | | | | |
|---|---|---|---|---|
| 1.340 | 2,4-Cl$_2$ | 2 | 5-Me | 1 |
| 1.341 | 2,5-Cl$_2$ | 2 | 5-Me | 1 |
| 1.342 | 2,6-Cl$_2$ | 2 | 5-Me | 1 |
| 1.343 | 3,4-Cl$_2$ | 2 | 5-Me | 1 |
| 1.344 | 3,5-Cl$_2$ | 2 | 5-Me | 1 |
| 1.345 | 2-CH$_3$, 4-Cl | 2 | 5-Me | 1 |
| 1.346 | 2-Cl, 4-CH$_3$ | 2 | 5-Me | 1 |
| 1.347 | 2-CF$_3$, 4-CH$_3$ | 2 | 5-Me | 1 |
| 1.348 | 2-CH$_3$, 4-CF$_3$ | 2 | 5-Me | 1 |
| 1.349 | — | — | 5-OCH$_3$ | 1 |
| 1.350 | 2-F | 1 | 5-OCH$_3$ | 1 |
| 1.351 | 3-F | 1 | 5-OCH$_3$ | 1 |
| 1.352 | 4-F | 1 | 5-OCH$_3$ | 1 |
| 1.353 | 2-Cl | 1 | 5-OCH$_3$ | 1 |
| 1.354 | 3-Cl | 1 | 5-OCH$_3$ | 1 |
| 1.355 | 4-Cl | 1 | 5-OCH$_3$ | 1 |
| 1.356 | 2-CH$_3$ | 1 | 5-OCH$_3$ | 1 |
| 1.357 | 3-CH$_3$ | 1 | 5-OCH$_3$ | 1 |
| 1.358 | 4-CH$_3$ | 1 | 5-OCH$_3$ | 1 |
| 1.359 | 2-OCH$_3$ | 1 | 5-OCH$_3$ | 1 |
| 1.360 | 3-OCH$_3$ | 1 | 5-OCH$_3$ | 1 |
| 1.361 | 4-OCH$_3$ | 1 | 5-OCH$_3$ | 1 |
| 1.362 | 2-CF$_3$ | 1 | 5-OCH$_3$ | 1 |
| 1.363 | 3-CF$_3$ | 1 | 5-OCH$_3$ | 1 |
| 1.364 | 4-CF$_3$ | 1 | 5-OCH$_3$ | 1 |
| 1.365 | 2,3-Cl$_2$ | 2 | 5-OCH$_3$ | 1 |
| 1.366 | 2,4-Cl$_2$ | 2 | 5-OCH$_3$ | 1 |
| 1.367 | 2,5-Cl$_2$ | 2 | 5-OCH$_3$ | 1 |
| 1.368 | 2,6-Cl$_2$ | 2 | 5-OCH$_3$ | 1 |
| 1.369 | 3,4-Cl$_2$ | 2 | 5-OCH$_3$ | 1 |
| 1.370 | 3,5-Cl$_2$ | 2 | 5-OCH$_3$ | 1 |
| 1.371 | 2-CH$_3$, 4-Cl | 2 | 5-OCH$_3$ | 1 |
| 1.372 | 2-Cl, 4-CH$_3$ | 2 | 5-OCH$_3$ | 1 |
| 1.373 | 2-CF$_3$, 4-CH$_3$ | 2 | 5-OCH$_3$ | 1 |
| 1.374 | 2-CH$_3$, 4-CF$_3$ | 2 | 5-OCH$_3$ | 1 |
| 1.375 | — | — | 5-CF$_3$ | 1 |
| 1.376 | 2-F | 1 | 5-CF$_3$ | 1 |
| 1.377 | 3-F | 1 | 5-CF$_3$ | 1 |
| 1.378 | 4-F | 1 | 5-CF$_3$ | 1 |
| 1.379 | 2-Cl | 1 | 5-CF$_3$ | 1 |
| 1.380 | 3-Cl | 1 | 5-CF$_3$ | 1 |
| 1.381 | 4-Cl | 1 | 5-CF$_3$ | 1 |
| 1.382 | 2-CH$_3$ | 1 | 5-CF$_3$ | 1 |
| 1.383 | 3-CH$_3$ | 1 | 5-CF$_3$ | 1 |
| 1.384 | 4-CH$_3$ | 1 | 5-CF$_3$ | 1 |
| 1.385 | 2-OCH$_3$ | 1 | 5-CF$_3$ | 1 |
| 1.386 | 3-OCH$_3$ | 1 | 5-CF$_3$ | 1 |
| 1.387 | 4-OCH$_3$ | 1 | 5-CF$_3$ | 1 |
| 1.388 | 2-CF$_3$ | 1 | 5-CF$_3$ | 1 |
| 1.389 | 3-CF$_3$ | 1 | 5-CF$_3$ | 1 |
| 1.390 | 4-CF$_3$ | 1 | 5-CF$_3$ | 1 |
| 1.391 | 2,3-Cl$_2$ | 2 | 5-CF$_3$ | 1 |
| 1.392 | 2,4-Cl$_2$ | 2 | 5-CF$_3$ | 1 |
| 1.393 | 2,5-Cl$_2$ | 2 | 5-CF$_3$ | 1 |
| 1.394 | 2,6-Cl$_2$ | 2 | 5-CF$_3$ | 1 |
| 1.395 | 3,4-Cl$_2$ | 2 | 5-CF$_3$ | 1 |
| 1.396 | 3,5-Cl$_2$ | 2 | 5-CF$_3$ | 1 |
| 1.397 | 2-CH$_3$, 4-Cl | 2 | 5-CF$_3$ | 1 |
| 1.398 | 2-Cl, 4-CH$_3$ | 2 | 5-CF$_3$ | 1 |
| 1.399 | 2-CF$_3$, 4-CH$_3$ | 2 | 5-CF$_3$ | 1 |
| 1.400 | 2-CH$_3$, 4-CF$_3$ | 2 | 5-CF$_3$ | 1 |
| 1.401 | — | — | 6-F | 1 |
| 1.402 | 2-F | 1 | 6-F | 1 |
| 1.403 | 3-F | 1 | 6-F | 1 |
| 1.404 | 4-F | 1 | 6-F | 1 |
| 1.405 | 2-Cl | 1 | 6-F | 1 |
| 1.406 | 3-Cl | 1 | 6-F | 1 |
| 1.407 | 4-Cl | 1 | 6-F | 1 |
| 1.408 | 2-CH$_3$ | 1 | 6-F | 1 |
| 1.409 | 3-CH$_3$ | 1 | 6-F | 1 |
| 1.410 | 4-CH$_3$ | 1 | 6-F | 1 |
| 1.411 | 2-OCH$_3$ | 1 | 6-F | 1 |
| 1.412 | 3-OCH$_3$ | 1 | 6-F | 1 |
| 1.413 | 4-OCH$_3$ | 1 | 6-F | 1 |
| 1.414 | 2-CF$_3$ | 1 | 6-F | 1 |
| 1.415 | 3-CF$_3$ | 1 | 6-F | 1 |
| 1.416 | 4-CF$_3$ | 1 | 6-F | 1 |
| 1.417 | 2,3-Cl$_2$ | 2 | 6-F | 1 |
| 1.418 | 2,4-Cl$_2$ | 2 | 6-F | 1 |
| 1.419 | 2,5-Cl$_2$ | 2 | 6-F | 1 |
| 1.420 | 2,6-Cl$_2$ | 2 | 6-F | 1 |
| 1.421 | 3,4-Cl$_2$ | 2 | 6-F | 1 |
| 1.422 | 3,5-Cl$_2$ | 2 | 6-F | 1 |
| 1.423 | 2-CH$_3$, 4-Cl | 2 | 6-F | 1 |
| 1.424 | 2-Cl, 4-CH$_3$ | 2 | 6-F | 1 |
| 1.425 | 2-CF$_3$, 4-CH$_3$ | 2 | 6-F | 1 |
| 1.426 | 2-CH$_3$, 4-CF$_3$ | 2 | 6-F | 1 |
| 1.427 | — | — | 6-Cl | 1 |
| 1.428 | 2-F | 1 | 6-Cl | 1 |
| 1.429 | 3-F | 1 | 6-Cl | 1 |
| 1.430 | 4-F | 1 | 6-Cl | 1 |
| 1.431 | 2-Cl | 1 | 6-Cl | 1 |
| 1.432 | 3-Cl | 1 | 6-Cl | 1 |
| 1.433 | 4-Cl | 1 | 6-Cl | 1 |
| 1.434 | 2-CH$_3$ | 1 | 6-Cl | 1 |
| 1.435 | 3-CH$_3$ | 1 | 6-Cl | 1 |
| 1.436 | 4-CH$_3$ | 1 | 6-Cl | 1 |
| 1.437 | 2-OCH$_3$ | 1 | 6-Cl | 1 |
| 1.438 | 3-OCH$_3$ | 1 | 6-Cl | 1 |
| 1.439 | 4-OCH$_3$ | 1 | 6-Cl | 1 |
| 1.440 | 2-CF$_3$ | 1 | 6-Cl | 1 |
| 1.441 | 3-CF$_3$ | 1 | 6-Cl | 1 |
| 1.442 | 4-CF$_3$ | 1 | 6-Cl | 1 |
| 1.443 | 2,3-Cl$_2$ | 2 | 6-Cl | 1 |
| 1.444 | 2,4-Cl$_2$ | 2 | 6-Cl | 1 |
| 1.445 | 2,5-Cl$_2$ | 2 | 6-Cl | 1 |
| 1.446 | 2,6-Cl$_2$ | 2 | 6-Cl | 1 |
| 1.447 | 3,4-Cl$_2$ | 2 | 6-Cl | 1 |
| 1.448 | 3,5-Cl$_2$ | 2 | 6-Cl | 1 |
| 1.449 | 2-CH$_3$, 4-Cl | 2 | 6-Cl | 1 |
| 1.450 | 2-Cl, 4-CH$_3$ | 2 | 6-Cl | 1 |
| 1.451 | 2-CF$_3$, 4-CH$_3$ | 2 | 6-Cl | 1 |
| 1.452 | 2-CH$_3$, 4-CF$_3$ | 2 | 6-Cl | 1 |
| 1.453 | — | — | 6-CH$_3$ | 1 |
| 1.454 | 2-F | 1 | 6-CH$_3$ | 1 |
| 1.455 | 3-F | 1 | 6-CH$_3$ | 1 |
| 1.456 | 4-F | 1 | 6-CH$_3$ | 1 |
| 1.457 | 2-Cl | 1 | 6-CH$_3$ | 1 |
| 1.458 | 3-Cl | 1 | 6-CH$_3$ | 1 |
| 1.459 | 4-Cl | 1 | 6-CH$_3$ | 1 |
| 1.460 | 2-CH$_3$ | 1 | 6-CH$_3$ | 1 |
| 1.461 | 3-CH$_3$ | 1 | 6-CH$_3$ | 1 |
| 1.462 | 4-CH$_3$ | 1 | 6-CH$_3$ | 1 |
| 1.463 | 2-OCH$_3$ | 1 | 6-CH$_3$ | 1 |
| 1.464 | 3-OCH$_3$ | 1 | 6-CH$_3$ | 1 |
| 1.465 | 4-OCH$_3$ | 1 | 6-CH$_3$ | 1 |
| 1.466 | 2-CF$_3$ | 1 | 6-CH$_3$ | 1 |
| 1.467 | 3-CF$_3$ | 1 | 6-CH$_3$ | 1 |
| 1.468 | 4-CF$_3$ | 1 | 6-CH$_3$ | 1 |
| 1.469 | 2,3-Cl$_2$ | 2 | 6-CH$_3$ | 1 |
| 1.470 | 2,4-Cl$_2$ | 2 | 6-CH$_3$ | 1 |
| 1.471 | 2,5-Cl$_2$ | 2 | 6-CH$_3$ | 1 |
| 1.472 | 2,6-Cl$_2$ | 2 | 6-CH$_3$ | 1 |
| 1.473 | 3,4-Cl$_2$ | 2 | 6-CH$_3$ | 1 |
| 1.474 | 3,5-Cl$_2$ | 2 | 6-CH$_3$ | 1 |
| 1.475 | 2-CH$_3$, 4-Cl | 2 | 6-CH$_3$ | 1 |
| 1.476 | 2-Cl, 4-CH$_3$ | 2 | 6-CH$_3$ | 1 |
| 1.477 | 2-CF$_3$, 4-CH$_3$ | 2 | 6-CH$_3$ | 1 |
| 1.478 | 2-CH$_3$, 4-CF$_3$ | 2 | 6-CH$_3$ | 1 |
| 1.479 | — | — | 6-OCH$_3$ | 1 |
| 1.448 | 2-F | 1 | 6-OCH$_3$ | 1 |
| 1.481 | 3-F | 1 | 6-OCH$_3$ | 1 |
| 1.482 | 4-F | 1 | 6-OCH$_3$ | 1 |
| 1.483 | 2-Cl | 1 | 6-OCH$_3$ | 1 |
| 1.484 | 3-Cl | 1 | 6-OCH$_3$ | 1 |
| 1.485 | 4-Cl | 1 | 6-OCH$_3$ | 1 |
| 1.486 | 2-CH$_3$ | 1 | 6-OCH$_3$ | 1 |
| 1.487 | 3-CH$_3$ | 1 | 6-OCH$_3$ | 1 |
| 1.488 | 4-CH$_3$ | 1 | 6-OCH$_3$ | 1 |
| 1.489 | 2-OCH$_3$ | 1 | 6-OCH$_3$ | 1 |
| 1.490 | 3-OCH$_3$ | 1 | 6-OCH$_3$ | 1 |
| 1.491 | 4-OCH$_3$ | 1 | 6-OCH$_3$ | 1 |
| 1.492 | 2-CF$_3$ | 1 | 6-OCH$_3$ | 1 |
| 1.493 | 3-CF$_3$ | 1 | 6-OCH$_3$ | 1 |
| 1.494 | 4-CF$_3$ | 1 | 6-OCH$_3$ | 1 |
| 1.495 | 2,3-Cl$_2$ | 2 | 6-OCH$_3$ | 1 |
| 1.496 | 2,4-Cl$_2$ | 2 | 6-OCH$_3$ | 1 |
| 1.497 | 2,5-Cl$_2$ | 2 | 6-OCH$_3$ | 1 |
| 1.498 | 2,6-Cl$_2$ | 2 | 6-OCH$_3$ | 1 |
| 1.499 | 3,4-Cl$_2$ | 2 | 6-OCH$_3$ | 1 |
| 1.500 | 3,5-Cl$_2$ | 2 | 6-OCH$_3$ | 1 |
| 1.501 | 2-CH$_3$, 4-Cl | 2 | 6-OCH$_3$ | 1 |
| 1.502 | 2-Cl, 4-CH$_3$ | 2 | 6-OCH$_3$ | 1 |
| 1.503 | 2-CF$_3$, 4-CH$_3$ | 2 | 6-OCH$_3$ | 1 |

TABLE 1-continued

| | | | | |
|---|---|---|---|---|
| 1.504 | 2-CH₃, 4-CF₃ | 2 | 6-OCH₃ | 1 |
| 1.505 | — | — | 6-CF₃ | 1 |
| 1.506 | 2-F | 1 | 6-CF₃ | 1 |
| 1.507 | 3-F | 1 | 6-CF₃ | 1 |
| 1.508 | 4-F | 1 | 6-CF₃ | 1 |
| 1.509 | 2-Cl | 1 | 6-CF₃ | 1 |
| 1.510 | 3-Cl | 1 | 6-CF₃ | 1 |
| 1.511 | 4-Cl | 1 | 6-CF₃ | 1 |
| 1.512 | 2-CH₃ | 1 | 6-CF₃ | 1 |
| 1.513 | 3-CH₃ | 1 | 6-CF₃ | 1 |
| 1.514 | 4-CH₃ | 1 | 6-CF₃ | 1 |
| 1.515 | 2-OCH₃ | 1 | 6-CF₃ | 1 |
| 1.516 | 3-OCH₃ | 1 | 6-CF₃ | 1 |
| 1.517 | 4-OCH₃ | 1 | 6-CF₃ | 1 |
| 1.518 | 2-CF₃ | 1 | 6-CF₃ | 1 |
| 1.519 | 3-CF₃ | 1 | 6-CF₃ | 1 |
| 1.520 | 4-CF₃ | 1 | 6-CF₃ | 1 |
| 1.521 | 2,3-Cl₂ | 2 | 6-CF₃ | 1 |
| 1.522 | 2,4-Cl₂ | 2 | 6-CF₃ | 1 |
| 1.523 | 2,5-Cl₂ | 2 | 6-CF₃ | 1 |
| 1.524 | 2,6-Cl₂ | 2 | 6-CF₃ | 1 |
| 1.525 | 3,4-Cl₂ | 2 | 6-CF₃ | 1 |
| 1.526 | 3,5-Cl₂ | 2 | 6-CF₃ | 1 |
| 1.527 | 2-CH₃, 4-Cl | 2 | 6-CF₃ | 1 |
| 1.528 | 2-Cl, 4-CH₃ | 2 | 6-CF₃ | 1 |
| 1.529 | 2-CF₃, 4-CH₃ | 2 | 6-CF₃ | 1 |
| 1.530 | 2-CH₃, 4-CF₃ | 2 | 6-CF₃ | 1 |
| 1.531 | — | — | 3,5-Cl₂ | 1 |
| 1.532 | 2-F | 1 | 3,5-Cl₂ | 1 |
| 1.533 | 3-F | 1 | 3,5-Cl₂ | 1 |
| 1.534 | 4-F | 1 | 3,5-Cl₂ | 1 |
| 1.535 | 2-Cl | 1 | 3,5-Cl₂ | 1 |
| 1.536 | 3-Cl | 1 | 3,5-Cl₂ | 1 |
| 1.537 | 4-Cl | 1 | 3,5-Cl₂ | 1 |
| 1.538 | 2-CH₃ | 1 | 3,5-Cl₂ | 1 |
| 1.539 | 3-CH₃ | 1 | 3,5-Cl₂ | 1 |
| 1.540 | 4-CH₃ | 1 | 3,5-Cl₂ | 1 |
| 1.541 | 2-OCH₃ | 1 | 3,5-Cl₂ | 1 |
| 1.542 | 3-OCH₃ | 1 | 3,5-Cl₂ | 1 |
| 1.543 | 4-OCH₃ | 1 | 3,5-Cl₂ | 1 |
| 1.544 | 2-CF₃ | 1 | 3,5-Cl₂ | 1 |
| 1.545 | 3-CF₃ | 1 | 3,5-Cl₂ | 1 |
| 1.546 | 4-CF₃ | 1 | 3,5-Cl₂ | 1 |
| 1.547 | 2,3-Cl₂ | 2 | 3,5-Cl₂ | 1 |
| 1.548 | 2,4-Cl₂ | 2 | 3,5-Cl₂ | 1 |
| 1.549 | 2,5-Cl₂ | 2 | 3,5-Cl₂ | 1 |
| 1.550 | 2,6-Cl₂ | 2 | 3,5-Cl₂ | 1 |
| 1.551 | 3,4-Cl₂ | 2 | 3,5-Cl₂ | 1 |
| 1.552 | 3,5-Cl₂ | 2 | 3,5-Cl₂ | 1 |
| 1.553 | 2-CH₃, 4-Cl | 2 | 3,5-Cl₂ | 1 |
| 1.554 | 2-Cl, 4-CH₃ | 2 | 3,5-Cl₂ | 1 |
| 1.555 | 2-CF₃, 4-CH₃ | 2 | 3,5-Cl₂ | 1 |
| 1.556 | 2-CH₃, 4-CF₃ | 2 | 3,5-Cl₂ | 1 |
| 1.557 | — | — | 3-Cl,5-F | 1 |
| 1.558 | 2-F | 1 | 3-Cl,5-F | 1 |
| 1.559 | 3-F | 1 | 3-Cl,5-F | 1 |
| 1.560 | 4-F | 1 | 3-Cl,5-F | 1 |
| 1.561 | 2-Cl | 1 | 3-Cl,5-F | 1 |
| 1.562 | 3-Cl | 1 | 3-Cl,5-F | 1 |
| 1.563 | 4-Cl | 1 | 3-Cl,5-F | 1 |
| 1.564 | 2-CH₃ | 1 | 3-Cl,5-F | 1 |
| 1.565 | 3-CH₃ | 1 | 3-Cl,5-F | 1 |
| 1.566 | 4-CH₃ | 1 | 3-Cl,5-F | 1 |
| 1.567 | 2-OCH₃ | 1 | 3-Cl,5-F | 1 |
| 1.568 | 3-OCH₃ | 1 | 3-Cl,5-F | 1 |
| 1.569 | 4-OCH₃ | 1 | 3-Cl,5-F | 1 |
| 1.570 | 2-CF₃ | 1 | 3-Cl,5-F | 1 |
| 1.571 | 3-CF₃ | 1 | 3-Cl,5-F | 1 |
| 1.572 | 4-CF₃ | 1 | 3-Cl,5-F | 1 |
| 1.573 | 2,3-Cl₂ | 2 | 3-Cl,5-F | 1 |
| 1.574 | 2,4-Cl₂ | 2 | 3-Cl,5-F | 1 |
| 1.575 | 2,5-Cl₂ | 2 | 3-Cl,5-F | 1 |
| 1.576 | 2,6-Cl₂ | 2 | 3-Cl,5-F | 1 |
| 1.577 | 3,4-Cl₂ | 2 | 3-Cl,5-F | 1 |
| 1.578 | 3,5-Cl₂ | 2 | 3-Cl,5-F | 1 |
| 1.579 | 2-CH₃, 4-Cl | 2 | 3-Cl,5-F | 1 |
| 1.580 | 2-Cl, 4-CH₃ | 2 | 3-Cl,5-F | 1 |
| 1.581 | 2-CF₃, 4-CH₃ | 2 | 3-Cl,5-F | 1 |
| 1.582 | 2-CH₃, 4-CF₃ | 2 | 3-Cl,5-F | 1 |
| 1.583 | — | — | 3-F,5-Cl | 1 |
| 1.584 | 2-F | 1 | 3-F,5-Cl | 1 |
| 1.585 | 3-F | 1 | 3-F,5-Cl | 1 |
| 1.586 | 4-F | 1 | 3-F,5-Cl | 1 |
| 1.587 | 2-Cl | 1 | 3-F,5-Cl | 1 |
| 1.588 | 3-Cl | 1 | 3-F,5-Cl | 1 |
| 1.589 | 4-Cl | 1 | 3-F,5-Cl | 1 |
| 1.590 | 2-CH₃ | 1 | 3-F,5-Cl | 1 |
| 1.591 | 3-CH₃ | 1 | 3-F,5-Cl | 1 |
| 1.592 | 4-CH₃ | 1 | 3-F,5-Cl | 1 |
| 1.593 | 2-OCH₃ | 1 | 3-F,5-Cl | 1 |
| 1.594 | 3-OCH₃ | 1 | 3-F,5-Cl | 1 |
| 1.595 | 4-OCH₃ | 1 | 3-F,5-Cl | 1 |
| 1.596 | 2-CF₃ | 1 | 3-F,5-Cl | 1 |
| 1.597 | 3-CF₃ | 1 | 3-F,5-Cl | 1 |
| 1.598 | 4-CF₃ | 1 | 3-F,5-Cl | 1 |
| 1.599 | 2,3-Cl₂ | 2 | 3-F,5-Cl | 1 |
| 1.600 | 2,4-Cl₂ | 2 | 3-F,5-Cl | 1 |
| 1.601 | 2,5-Cl₂ | 2 | 3-F,5-Cl | 1 |
| 1.602 | 2,6-Cl₂ | 2 | 3-F,5-Cl | 1 |
| 1.603 | 3,4-Cl₂ | 2 | 3-F,5-Cl | 1 |
| 1.604 | 3,5-Cl₂ | 2 | 3-F,5-Cl | 1 |
| 1.605 | 2-CH₃, 4-Cl | 2 | 3-F,5-Cl | 1 |
| 1.606 | 2-Cl, 4-CH₃ | 2 | 3-F,5-Cl | 1 |
| 1.607 | 2-CF₃, 4-CH₃ | 2 | 3-F,5-Cl | 1 |
| 1.608 | 2-CH₃, 4-CF₃ | 2 | 3-F,5-Cl | 1 |
| 1.609 | — | — | 3,5,6-F₃ | 1 |
| 1.610 | 2-F | 1 | 3,5,6-F₃ | 1 |
| 1.611 | 3-F | 1 | 3,5,6-F₃ | 1 |
| 1.612 | 4-F | 1 | 3,5,6-F₃ | 1 |
| 1.613 | 2-Cl | 1 | 3,5,6-F₃ | 1 |
| 1.614 | 3-Cl | 1 | 3,5,6-F₃ | 1 |
| 1.615 | 4-Cl | 1 | 3,5,6-F₃ | 1 |
| 1.616 | 2-CH₃ | 1 | 3,5,6-F₃ | 1 |
| 1.617 | 3-CH₃ | 1 | 3,5,6-F₃ | 1 |
| 1.618 | 4-CH₃ | 1 | 3,5,6-F₃ | 1 |
| 1.619 | 2-OCH₃ | 1 | 3,5,6-F₃ | 1 |
| 1.620 | 3-OCH₃ | 1 | 3,5,6-F₃ | 1 |
| 1.621 | 4-OCH₃ | 1 | 3,5,6-F₃ | 1 |
| 1.622 | 2-CF₃ | 1 | 3,5,6-F₃ | 1 |
| 1.623 | 3-CF₃ | 1 | 3,5,6-F₃ | 1 |
| 1.624 | 4-CF₃ | 1 | 3,5,6-F₃ | 1 |
| 1.625 | 2,3-Cl₂ | 2 | 3,5,6-F₃ | 1 |
| 1.626 | 2,4-Cl₂ | 2 | 3,5,6-F₃ | 1 |
| 1.627 | 2,5-Cl₂ | 2 | 3,5,6-F₃ | 1 |
| 1.628 | 2,6-Cl₂ | 2 | 3,5,6-F₃ | 1 |
| 1.629 | 3,4-Cl₂ | 2 | 3,5,6-F₃ | 1 |
| 1.630 | 3,5-Cl₂ | 2 | 3,5,6-F₃ | 1 |
| 1.631 | 2-CH₃, 4-Cl | 2 | 3,5,6-F₃ | 1 |
| 1.632 | 2-Cl, 4-CH₃ | 2 | 3,5,6-F₃ | 1 |
| 1.633 | 2-CF₃, 4-CH₃ | 2 | 3,5,6-F₃ | 1 |
| 1.634 | 2-CH₃, 4-CF₃ | 2 | 3,5,6-F₃ | 1 |
| 1.635 | — | — | 3,5-(CH₃)₂ | 1 |
| 1.636 | 2-F | 1 | 3,5-(CH₃)₂ | 1 |
| 1.637 | 3-F | 1 | 3,5-(CH₃)₂ | 1 |
| 1.638 | 4-F | 1 | 3,5-(CH₃)₂ | 1 |
| 1.639 | 2-Cl | 1 | 3,5-(CH₃)₂ | 1 |
| 1.640 | 3-Cl | 1 | 3,5-(CH₃)₂ | 1 |
| 1.641 | 4-Cl | 1 | 3,5-(CH₃)₂ | 1 |
| 1.642 | 2-CH₃ | 1 | 3,5-(CH₃)₂ | 1 |
| 1.643 | 3-CH₃ | 1 | 3,5-(CH₃)₂ | 1 |
| 1.644 | 4-CH₃ | 1 | 3,5-(CH₃)₂ | 1 |
| 1.645 | 2-OCH₃ | 1 | 3,5-(CH₃)₂ | 1 |
| 1.646 | 3-OCH₃ | 1 | 3,5-(CH₃)₂ | 1 |
| 1.647 | 4-OCH₃ | 1 | 3,5-(CH₃)₂ | 1 |
| 1.648 | 2-CF₃ | 1 | 3,5-(CH₃)₂ | 1 |
| 1.649 | 3-CF₃ | 1 | 3,5-(CH₃)₂ | 1 |
| 1.650 | 4-CF₃ | 1 | 3,5-(CH₃)₂ | 1 |
| 1.651 | 2,3-Cl₂ | 2 | 3,5-(CH₃)₂ | 1 |
| 1.652 | 2,4-Cl₂ | 2 | 3,5-(CH₃)₂ | 1 |
| 1.653 | 2,5-Cl₂ | 2 | 3,5-(CH₃)₂ | 1 |
| 1.654 | 2,6-Cl₂ | 2 | 3,5-(CH₃)₂ | 1 |
| 1.655 | 3,4-Cl₂ | 2 | 3,5-(CH₃)₂ | 1 |
| 1.656 | 3,5-Cl₂ | 2 | 3,5-(CH₃)₂ | 1 |
| 1.657 | 2-CH₃, 4-Cl | 2 | 3,5-(CH₃)₂ | 1 |
| 1.658 | 2-Cl, 4-CH₃ | 2 | 3,5-(CH₃)₂ | 1 |
| 1.659 | 2-CF₃, 4-CH₃ | 2 | 3,5-(CH₃)₂ | 1 |
| 1.660 | 2-CH₃, 4-CF₃ | 2 | 3,5-(CH₃)₂ | 1 |
| 1.661 | — | — | 5,6-(CH₃)₂ | 1 |
| 1.662 | 2-F | 1 | 5,6-(CH₃)₂ | 1 |
| 1.663 | 3-F | 1 | 5,6-(CH₃)₂ | 1 |
| 1.664 | 4-F | 1 | 5,6-(CH₃)₂ | 1 |
| 1.665 | 2-Cl | 1 | 5,6-(CH₃)₂ | 1 |
| 1.666 | 3-Cl | 1 | 5,6-(CH₃)₂ | 1 |
| 1.667 | 4-Cl | 1 | 5,6-(CH₃)₂ | 1 |

TABLE 1-continued

| No. | X | m | Y | n |
|---|---|---|---|---|
| 1.668 | 2-CH₃ | 1 | 5,6-(CH₃)₂ | 1 |
| 1.669 | 3-CH₃ | 1 | 5,6-(CH₃)₂ | 1 |
| 1.670 | 4-CH₃ | 1 | 5,6-(CH₃)₂ | 1 |
| 1.671 | 2-OCH₃ | 1 | 5,6-(CH₃)₂ | 1 |
| 1.672 | 3-OCH₃ | 1 | 5,6-(CH₃)₂ | 1 |
| 1.673 | 4-OCH₃ | 1 | 5,6-(CH₃)₂ | 1 |
| 1.674 | 2-CF₃ | 1 | 5,6-(CH₃)₂ | 1 |
| 1.675 | 3-CF₃ | 1 | 5,6-(CH₃)₂ | 1 |
| 1.676 | 4-CF₃ | 1 | 5,6-(CH₃)₂ | 1 |
| 1.677 | 2,3-Cl₂ | 2 | 5,6-(CH₃)₂ | 1 |
| 1.678 | 2,4-Cl₂ | 2 | 5,6-(CH₃)₂ | 1 |
| 1.679 | 2,5-Cl₂ | 2 | 5,6-(CH₃)₂ | 1 |
| 1.680 | 2,6-Cl₂ | 2 | 5,6-(CH₃)₂ | 1 |
| 1.681 | 3,4-Cl₂ | 2 | 5,6-(CH₃)₂ | 1 |
| 1.682 | 3,5-Cl₂ | 2 | 5,6-(CH₃)₂ | 1 |
| 1.683 | 2-CH₃, 4-Cl | 2 | 5,6-(CH₃)₂ | 1 |
| 1.684 | 2-Cl, 4-CH₃ | 2 | 5,6-(CH₃)₂ | 1 |
| 1.685 | 2-CF₃, 4-CH₃ | 2 | 5,6-(CH₃)₂ | 1 |
| 1.686 | 2-CH₃, 4-CF₃ | 2 | 5,6-(CH₃)₂ | 1 |
| 1.687 | — | — | 3,4-(CH₃)₂ | 1 |
| 1.688 | 2-F | 1 | 3,4-(CH₃)₂ | 1 |
| 1.689 | 3-F | 1 | 3,4-(CH₃)₂ | 1 |
| 1.690 | 4-F | 1 | 3,4-(CH₃)₂ | 1 |
| 1.691 | 2-Cl | 1 | 3,4-(CH₃)₂ | 1 |
| 1.692 | 3-Cl | 1 | 3,4-(CH₃)₂ | 1 |
| 1.693 | 4-Cl | 1 | 3,4-(CH₃)₂ | 1 |
| 1.694 | 2-CH₃ | 1 | 3,4-(CH₃)₂ | 1 |
| 1.695 | 3-CH₃ | 1 | 3,4-(CH₃)₂ | 1 |
| 1.696 | 4-CH₃ | 1 | 3,4-(CH₃)₂ | 1 |
| 1.697 | 2-OCH₃ | 1 | 3,4-(CH₃)₂ | 1 |
| 1.698 | 3-OCH₃ | 1 | 3,4-(CH₃)₂ | 1 |
| 1.699 | 4-OCH₃ | 1 | 3,4-(CH₃)₂ | 1 |
| 1.700 | 2-CF₃ | 1 | 3,4-(CH₃)₂ | 1 |
| 1.701 | 3-CF₃ | 1 | 3,4-(CH₃)₂ | 1 |
| 1.702 | 4-CF₃ | 1 | 3,4-(CH₃)₂ | 1 |
| 1.703 | 2,3-Cl₂ | 2 | 3,4-(CH₃)₂ | 1 |
| 1.704 | 2,4-Cl₂ | 2 | 3,4-(CH₃)₂ | 1 |
| 1.705 | 2,5-Cl₂ | 2 | 3,4-(CH₃)₂ | 1 |
| 1.706 | 2,6-Cl₂ | 2 | 3,4-(CH₃)₂ | 1 |
| 1.707 | 3,4-Cl₂ | 2 | 3,4-(CH₃)₂ | 1 |
| 1.708 | 3,5-Cl₂ | 2 | 3,4-(CH₃)₂ | 1 |
| 1.709 | 2-CH₃, 4-Cl | 2 | 3,4-(CH₃)₂ | 1 |
| 1.710 | 2-Cl, 4-CH₃ | 2 | 3,4-(CH₃)₂ | 1 |
| 1.711 | 2-CF₃, 4-CH₃ | 2 | 3,4-(CH₃)₂ | 1 |
| 1.712 | 2-CH₃, 4-CF₃ | 2 | 3,4-(CH₃)₂ | 1 |
| 1.713 | — | — | 4,6-(OCH₃)₂ | 1 |
| 1.714 | 2-F | 1 | 4,6-(OCH₃)₂ | 1 |
| 1.715 | 3-F | 1 | 4,6-(OCH₃)₂ | 1 |
| 1.716 | 4-F | 1 | 4,6-(OCH₃)₂ | 1 |
| 1.717 | 2-Cl | 1 | 4,6-(OCH₃)₂ | 1 |
| 1.718 | 3-Cl | 1 | 4,6-(OCH₃)₂ | 1 |
| 1.719 | 4-Cl | 1 | 4,6-(OCH₃)₂ | 1 |
| 1.720 | 2-CH₃ | 1 | 4,6-(OCH₃)₂ | 1 |
| 1.721 | 3-CH₃ | 1 | 4,6-(OCH₃)₂ | 1 |
| 1.722 | 4-CH₃ | 1 | 4,6-(OCH₃)₂ | 1 |
| 1.723 | 2-OCH₃ | 1 | 4,6-(OCH₃)₂ | 1 |
| 1.724 | 3-OCH₃ | 1 | 4,6-(OCH₃)₂ | 1 |
| 1.725 | 4-OCH₃ | 1 | 4,6-(OCH₃)₂ | 1 |
| 1.726 | 2-CF₃ | 1 | 4,6-(OCH₃)₂ | 1 |
| 1.727 | 3-CF₃ | 1 | 4,6-(OCH₃)₂ | 1 |
| 1.728 | 4-CF₃ | 1 | 4,6-(OCH₃)₂ | 1 |
| 1.729 | 2,3-Cl₂ | 2 | 4,6-(OCH₃)₂ | 1 |
| 1.730 | 2,4-Cl₂ | 2 | 4,6-(OCH₃)₂ | 1 |
| 1.731 | 2,5-Cl₂ | 2 | 4,6-(OCH₃)₂ | 1 |
| 1.732 | 2,6-Cl₂ | 2 | 4,6-(OCH₃)₂ | 1 |
| 1.733 | 3,4-Cl₂ | 2 | 4,6-(OCH₃)₂ | 1 |
| 1.734 | 3,5-Cl₂ | 2 | 4,6-(OCH₃)₂ | 1 |
| 1.735 | 2-CH₃, 4-Cl | 2 | 4,6-(OCH₃)₂ | 1 |
| 1.736 | 2-Cl, 4-CH₃ | 2 | 4,6-(OCH₃)₂ | 1 |
| 1.737 | 2-CF₃, 4-CH₃ | 2 | 4,6-(OCH₃)₂ | 1 |
| 1.738 | 2-CH₃, 4-CF₃ | 2 | 4,6-(OCH₃)₂ | 1 |

The α-keto carboxylic esters VIIa are valuable intermediates, especially for the synthesis of E-oxime ethers of phenoxymethylphenylglyoxylic esters I which are used in crop protection, preferably as fungicides (cf. EP-A 253 213 and EP-A 254 426).

The final products I can be prepared by reacting the α-keto carboxylic esters VIIa, where appropriate as crude product mixtures together with the keto carboxylic ester dimethyl acetals VIIb, with O-methylhydroxylamine or one of its acid addition salts, and the resulting mixture of E/Z isomers of the oxime ethers being treated simultaneously or subsequently with an acid to convert the Z into the E isomers:

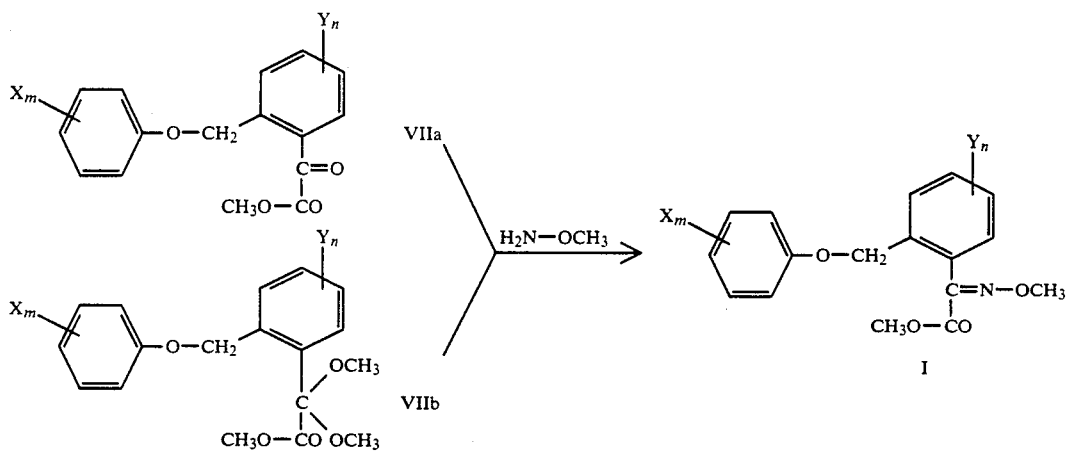

EXAMPLE 6 (according to the invention)

Methyl 2-(2-methylphenoxymethyl)phenylglyoxylate
6.1 Without diluent 4.1 g (40 mmol) of acetic anhydride were added to a solution of 10 g (40 mmol) of 2-(2-methylphenoxymethyl)benzoyl cyanide in 150 ml of methanol. Then 65 g (1.78 mol) of gaseous hydrogen chloride were passed in at −5° to −10° C., the mixture was allowed to warm to 20° C. and then stirred at this temperature for about 15 hours. Subsequently the ammonium chloride which had been formed was removed and washed with 100 ml of methylene chloride, after which the combined organic phases were concentrated. Yield: 11.3 g of a yellow-brown solid which proved on analysis by gas chromatography to have the following composition:

19.3 mol% of methyl 2-(2-methylphenoxymethyl)-benzoate (byproduct), 12.9 mol% of methyl 2-(2-methylphenoxymethyl)-phenylglyoxylate (product of the formula VIIa), 11.8 mol% of methyl 2-(2-methylphenoxymethyl)-phenylglyoxylate dimethyl acetal (product of the formula VIIb),
60.9 mol% of 2-(2-methylphenoxymethyl)phenylglyoxyl=amide (product of the formula VIIc).
6.2 With diluent (toluene)

30 ml of methanol and 20.4 g (0.2 mol) of acetic anhydride were added to a suspension of 50 g (0.2 mol) of 2-(2-methylphenoxymethyl)benzoyl cyanide in 150 ml of toluene. Then 22 g (0.6 mol) of gaseous hydrogen chloride were passed in at 25° to 30° C. and the mixture was then stirred for about 15 hours. Subsequently the ammonium chloride which had formed was removed and washed with ml of methylene chloride, after which the combined organic phases were concentrated. Yield: 50 g of a yellow-brown solid which proved on analysis by gas chromatography to have the following composition:
7.8 mol% of methyl 2-(2-methylphenoxymethyl)benzoate (byproduct),
34 1 mol% of methyl 2-(2-methylphenoxymethyl)-phenylglyoxylate (product of the formula VIIa),
54.1 mol% of 2-(2-methylphenoxymethyl)phenylglyoxylamide (product of the formula VIIc).

$^1$H NMR of methyl 2-(2-methylphenoxymethyl)phenylglyoxylate (in CDCl$_3$; TMS as internal standard): 2.28 ppm (s,3H); 3.77 ppm (s,3H); 5.38 ppm (s,2H); 6.83-7.79 ppm (m,8H);

$^1$H NMR of the 2-(2-methylphenoxymethyl)phenylglyoxylamide (in CDCl$_3$; TMS as internal standard): 2.23 ppm (s,3H); 5.31 ppm (s,2H); 5.81 (ppm (br,2H); 6.87-7.99 ppm (m,8H).

EXAMPLE 7 (according to the invention)

Conversion of 2-(2-methylphenoxymethyl)phenylglyoxylamide into methyl 2-(2-methylphenoxymethyl)-phenylglyoxylate 10 ml of concentrated aqueous sulfuric acid were added to a solution of 39.4 g of a mixture composed of 38.9 mol% of 2-(2-methylphenoxymethyl)phenylglyoxylamide and 57.6 mol% of methyl 2-(2-methylphenoxymethyl)phenylglyoxylate (according to HPLC analysis) in 200 ml of methanol. The mixture was refluxed for 2.5 hours and then stirred at 20°-25° C. for about 15 hours. HPLC analysis of a sample showed that the dissolved substance now comprised 81.6 mol% of methyl 2-(2-methylphenoxymethyl)-phenylglyoxylate and only 1.4 mol% of 2-(2-methylphenoxymethyl)-phenylglyoxylamide. After conventional working up of the mixture, it was possible to use the crude product directly for the synthesis of the corresponding final product of the formula I.

EXAMPLE 8 (according to the invention)

Cleavage of methyl 2-(2-methylphenoxymethyl)phenylglyoxylate dimethyl acetal to give methyl 2-(2-methylphenoxymethyl)phenylglyoxylate 100 ml of concentrated aqueous hydrochloric acid were added to a solution of 130.2 g of a mixture composed of 55.5 mol% of methyl 2-(2-methylphenoxymethyl)phenylglyoxylate, 32.2 mol% of methyl 2-(2-methylphenoxymethyl)phenylglyoxylate dimethyl acetal and 12.2 mol% of methyl 2-(2-methylphenoxymethyl)benzoate (according to analysis by gas chromatography) in 300 ml of methylene chloride. The mixture was stirred at 20°-25° C. for 15 hours, then washed with 100 ml of water, 100 ml of concentrated aqueous sodium carbonate solution and again with 100 ml of water, and finally dried and concentrated. Yield: 117.9 g of a yellow oil which (according to analysis by gas chromatography) comprised 83.9 mol% of methyl 2-(2-methylphenoxymethyl)phenylglyoxylate and still 12.3 mol% of methyl 2-(2-methylphenoxymethyl)-benzoate.

EXAMPLE 9 (Comparative prior art examples)

9.1) Reaction of 2-(2-methylphenoxymethyl)benzoyl cyanide with NaBr catalysis (cf. US-A 4,234,739)
Main reaction: conversion into methyl benzoate
9.1.1 in solution:

A solution of 20.5 g (81 mmol) of 2-(2-methylphenoxymethyl)benzoyl cyanide in 80 ml of methylene chloride was added dropwise to a mixture of 19.6 ml of 85% by weight sulfuric acid and 1.09 g of sodium bromide at 20°-25° C. The mixture was then heated to 40° C. and 38.9 ml of methanol were added, and the mixture was then stirred at this temperature for 3 hours. HPLC analysis of a sample showed quantitative formation of methyl 2-(2-methylphenoxymethyl)benzoate (unwanted competing product). 100 ml of water were added, and the resulting mixture was extracted twice with 50 ml of methylene chloride each time, after which the combined organic phases were worked up as usual. Yield: 95% of the competing product.

9.1.2 Without solvent:

18.9 g (78 mmol) of 2-(2-methylphenoxymethyl)-benzoyl cyanide were added to a mixture of 20 ml of 85% by weight sulfuric acid and 1.0 g of sodium bromide at about 20° C. 100 ml of methanol were then added dropwise, during which the temperature rose to 80° C. and hydrogen cyanide was formed. The mixture was then stirred at 80° C. for 3 hours and, after cooling to about 25° C., extracted with 100 ml of toluene. Analysis by gas chromatography showed quantitative formation of methyl 2-(2-methylphenoxymethyl) benzoate (unwanted competing product) with this version of the synthesis too.

Melting point: 33°-37° C.; $^1$H-NMR (in CDCl$_3$, TMS as internal standard): 2.33 ppm (s,3H); 3.87 ppm (s,3H); 5.48 ppm (s,2H); 6.83-8.01 ppm (m,8H).

9.2) Ritter reaction of 2-(2-methylphenoxymethyl)benzoyl cyanide (cf. EP-A 034,240)

Main reactions: cyanide elimination and alkylation of the phenoxy radical

A solution of 5 g (20 mmol) of 2-(2-methylphenoxymethyl)benzoyl cyanide in 80 ml of methyl tertbutyl ether was added to a mixture of 4.2 g of acetic acid and 3 g of concentrated aqueous sulfuric acid at about 20° C. The mixture was stirred for 2 hours and then 10 ml of concentrated aqueous sulfuric acid were added. The mixture was then refluxed for 2 hours and subsequently 100 ml of water were added. The organic phase was separated off, dried and concentrated. Yield: 5.9 g of a crude product which had the following composition according to gas chromatography and mass spectroscopy:
15 mol% of methyl 2-(2-methylphenoxymethyl)benzoate (unwanted competing product),
17 mol% of methyl 2-(2-methyl-4-tert-butylphenoxymethyl)benzoate (unwanted competing product),
13 mol% of N-tert-butyl-2-(2-methylphenoxymethyl)-phenylglyoxylamide,
23 mol% of N-tert-butyl-2-(2-methyl-4-tert-butylphenoxymethyl)phenylglyoxylamide (unwanted byproduct).

9.3) Reaction of 2-(2'-methylphenoxymethyl)benzoyl cyanide with sulfuric acid and acetic anhydride (cf. EP-A 035,707)

Main reaction: cyanide elimination and sulfonylation of the phenoxy radical 39 g of concentrated aqueous sulfuric acid were slowly added to a mixture of 80 ml of acetic anhydride and 50 g (0.199 mol) of 2-(2-methylphenoxymethyl)-benzoyl cyanide at 20° C. The mixture had heated to 90° C. during this and, after cooling to 25° C., 100 ml of water were added and then, to pH 3, concentrate aqueous sodium hydroxide solution. The brown precipitated which had formed was then removed and dried. Yield: 83.8% of 2-(2-methyl-4-sulfophenoxymethyl)benzoic acid (unwanted product); melting point: 242°–244° C.
$^1$H-NMR (in d6-DMSO; TMS as internal standard): 2.25 ppm (s,3H); 5.50 ppm (s,2H); 6.93–7.98 ppm (m,7H).

The present invention furthermore relates to a process for preparing α-keto carboxylic esters of the formula VII

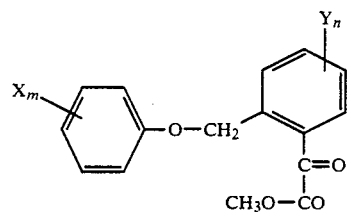

where X and Y are each halogen, $C_1$–$C_4$-alkyl, $C_1$–$C_4$-alkoxy or trifluoromethyl;
m is an integer from 0 to 4;
n is an integer from 0 to 3.

Various processes for preparing aromatic alpha-keto esters are described in the literature, but none of them have phenoxymethyl on the aromatic ring.

Thus, Synth. Commun. 11 (1981) 943 discloses the preparation of ethyl phenylglyoxylate in a Grignard reaction from phenylmagnesium bromide and diethyl oxalate:

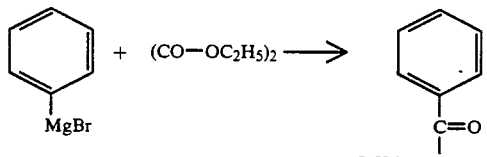

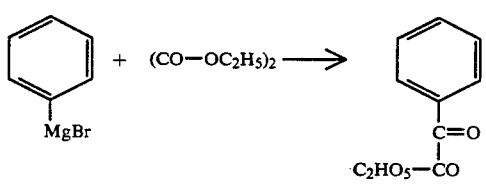

Angew. Chemie 68 (1956) 430 and idem 94 (1982) 1, Org. Synth. 24 (1944) 16 and J. Org. Chem. 29 (1964) 278 describe methods for hydrolyzing benzoyl cyanides with concentrated mineral acids and for converting the resulting keto carboxylic acids into phenylglyoxylic esters, but benzoic esters are formed as by-products:

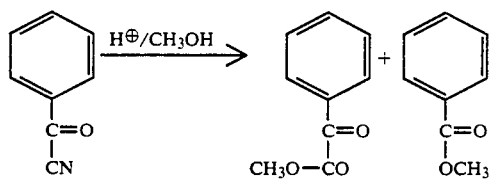

US-A 4 234 739, DE-A 2 708 189 and Tetrah. Lett., (1980) 3539 disclose how the formation of the benzoic esters can in several cases be substantially suppressed by adding a halide.

However, neither method is suitable for preparing the α-keto carboxylic esters VII because of the steric hinderance of the bulky ortho-phenoxymethyl group. The Grignard reaction therefore gives only very low yields of the required α-keto carboxylic ester VII. Pinner reaction of o-phenoxymethylbenzoyl cyanides with methanol is in competition with the predominate formation of the o-phenoxymethylbenzoic esters:

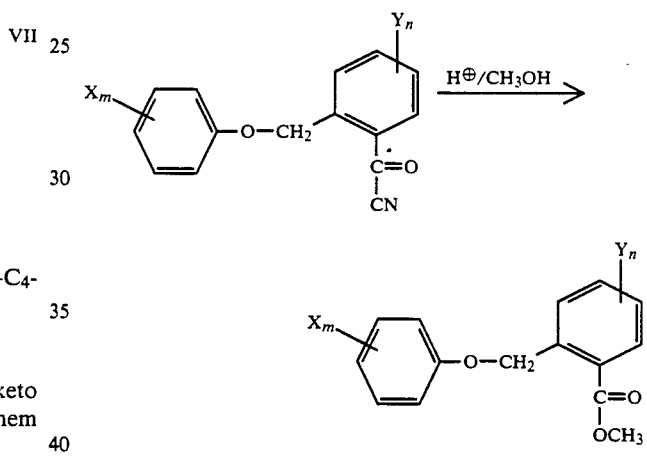

It is possible to obtain α-keto esters from beta-keto sulfoxides by bromination with bromine in the presence of sodium hydride as base [J. Am. Chem. Soc. 88 (1966) 5498] or with N-bromosuccinimide [Synthesis (1982) 41] and boiling the product with methanol in the presence of an acid by the Pummerer reaction:

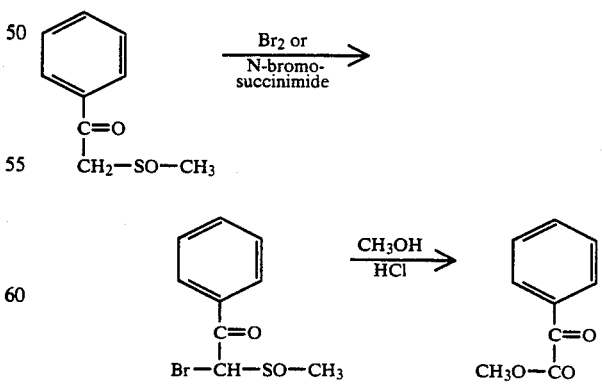

The drastic conditions necessary for this reaction (halogenating agent, strong acid, high temperature) and the inadequate yield of keto ester by the variant disclosed in J. Amer. Chem. Soc. make this process appear equally unsuitable for preparing the α-keto carboxylic esters VII. In particular, owing to the bulky ortho-phenoxymethyl group, large amounts of byproducts are to be expected, for example due to halogenation of the aromatic ring or of the methylene group in the phenoxymethyl moiety or even by cleavage of the benzylether linkage.

It is also known to convert benzoyl cyanides either into the corresponding keto tert-butylamides IX by the Ritter reaction (cf. EP-A 034 240) or into keto N-acylamides X (cf. EP-A 35 707). Both compounds can subsequently be converted into keto carboxylic acids and keto esters:

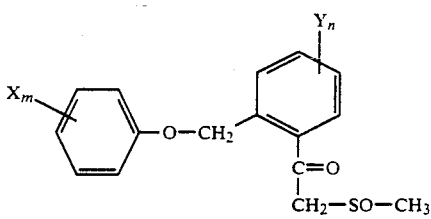

and c) reacting this mixture with methanol in the presence of an acid.

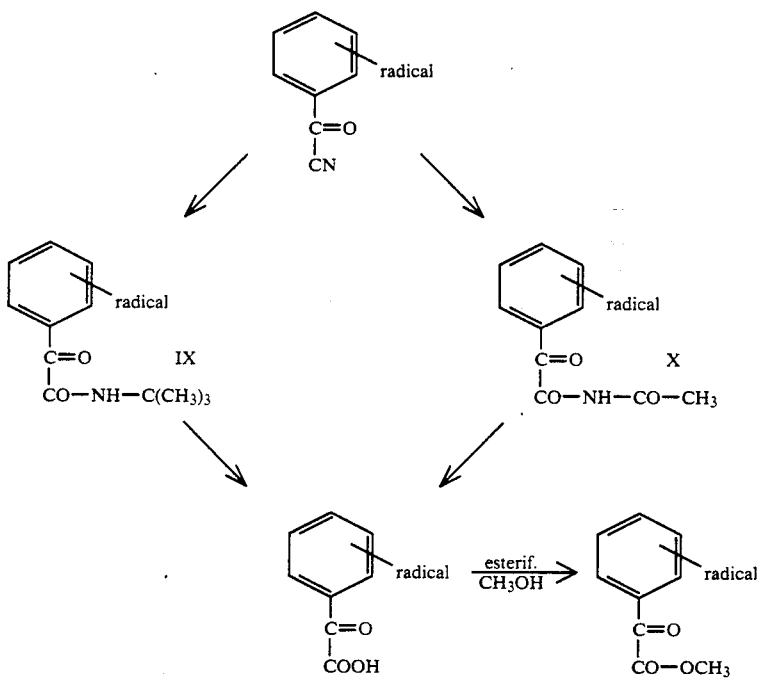

However, the α-keto carboxylic esters VII cannot be prepared by this method.

It is an object of the present invention to make the compounds VII more easily accessible.

We have found that this object is achieved by a novel process for preparing α-keto carboxylic esters VII, which comprises a) reacting an o-phenoxymethylbenzoic ester of the formula V

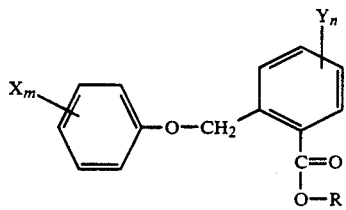

where R is $C_1$-$C_4$-alkyl, with dimethyl sulfoxide in the presence of a base, b) adding a halogenating agent to the β-keto sulfoxide product of the formula VIa We have also found novel beta-keto sulfoxides of the formula VI

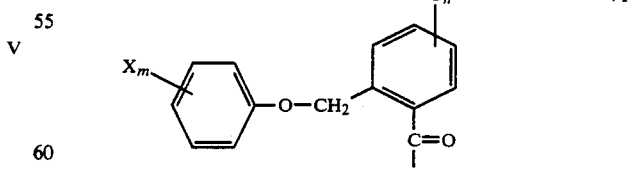

where X and Y are each halogen, $C_1$-$C_4$-alkyl, $C_1$-$C_4$-alkoxy or trifluoromethyl;
m is an integer from 0 to 4;
n is an integer from 0 to 3,
and novel α-keto carboxylic esters of the formula VII′

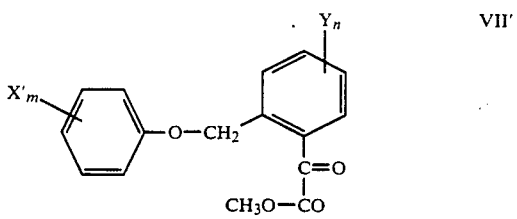

VII' where X' and Y are each halogen, $C_1$–$C_4$-alkyl, $C_1$–$C_4$-alkoxy or trifluoromethyl;

m is an integer from 0 to 4;

n is an integer from 0 to 3, with the proviso that n can be 0 only when X' is 2-chloro, 2-fluoro, 2-methyl, 4-methyl, 4-tert-butyl, 2-methoxy or 2-trifluoromethyl and m is 0 or 1, or X' is 2,4-dichloro or 4-chloro-2-methyl and m is 2 as intermediates.

The phenoxymethylbenzoic esters of the formula VI used as starting materials can be obtained, for example, by reacting phenols II with phthalides III, preferably under basic conditions [cf., for example, Coll. Czech. Chem. Comm. 32, (1967) 3448] and converting the resulting o-phenoxymethylbenzoic acids into their esters (cf. Organikum, VEB Deutscher Verlag der Wissenschaften, 15th edition, Berlin 1977, page 499):

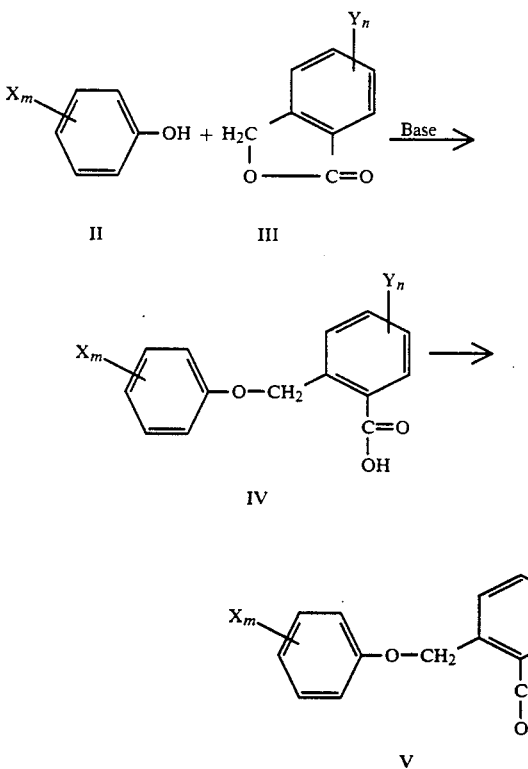

Step (a) is generally carried out in an inert solvent or diluent, for example in an ether such as tetrahydrofuran or preferably without solvent in an excess of dimethyl sulfoxide.

Suitable bases are alcoholates such as sodium methylate, sodium ethylate, sodium tert-butanolate and potassium tert-butanolate, alkali metal hydrides such as sodium hydride and alkali metal amides such as sodamide; sodium methylate is particularly preferred, in which case methanol is expediently used as solvent.

Normally the o-phenoxymethylbenzoic ester VI, base and dimethyl sulfoxide are employed in the stoichiometric ratio, but an excess of one of the components, for example up to 10 mol %, may also be advantageous. If the reaction is carried out without solvent in dimethyl sulfoxide, the latter is present in large excess. It is preferable to employ an excess of from 100 to 300 mol % of base.

The reaction is generally carried out under atmospheric pressure, in which case a temperature of from 0° to 120° C., in particular 50° to 70° C., is advisable.

In step (b), the β-keto sulfoxides VI are mixed with a halogenating agent, for example a halogen such as chlorine or bromine, an N-halosuccinimide such as N-chlorosuccinimide or N-bromosuccinimide, sulfuryl chloride or 3,3-dimethyl-5,5-dibromohydantoin, especially bromine, N-bromosuccinimide and 3,3-dimethyl-5,5-dibromohydantoin, and reacted, if required in the presence of a base.

The reaction is usually carried out in an inert solvent or diluent, for example in a hydrocarbon such as cyclohexane or in a ketone such as acetone.

Examples of suitable bases are alcoholates such as sodium methylate and sodium ethylate, and tertiary amines such as triethylamine and pyridine.

Normally the β-keto sulfoxide, halogenating agent and base are employed in the stoichiometric ratio, but an excess of one of the components, for example up to 10 mol %, may also be advantageous. It is preferable to employ an excess of from 100 to 300 mol % of halogenating agent.

This step is also expediently carried out under atmospheric pressure, in which case a temperature of from 0° to 80° C., in particular 20° to 65° C., is advisable.

Finally, the halogenated β-keto sulfoxides are reacted with methanol in the presence of a catalytic amount of a mineral acid.

Suitable mineral acids are hydrochloric acid and sulfuric acid, especially hydrochloric acid, which is preferably used as concentrated aqueous solution.

The amount of methanol is not critical. Generally stoichiometric amounts of halogenated β-keto sulfoxide and methanol, or an excess of up to about 300 mol % of methanol, are employed. If methanol is used as solvent, it is normally present in a large excess.

The statements about the temperature and the pressure made for step (b) apply.

The β-keto sulfoxides VI can also be mixed and reacted simultaneously with a halogenating agent, methanol and catalytic amounts of acid.

The reaction mixture is worked up in a conventional manner.

One variant of the process according to the invention comprises the products VI which result from the reaction of o-phenoxymethylbenzoic esters V with dimethyl sulfoxide being mixed, without isolation from the reaction mixture, with a halogenating agent, and this mixture being reacted simultaneously or subsequently with methanol in the presence of an acid.

The process according to the invention can be carried out either continuously or batchwise. In the continuous procedure, the reactants are preferably passed through a tubular reactor or a cascade of agitated vessels.

The process according to the invention provides the β-keto carboxylic esters VII in high yields and with very satisfactory purity.

The described method of preparation can be used successfully to synthesize all β-keto carboxylic esters VII complying with the definition, especially those compounds where X and Y are each selected from a group comprising:

halogen such as fluorine, chlorine, bromine and iodine, especially fluorine and chlorine;

branched or unbranched $C_1$–$C_4$-alkyl such as methyl, ethyl, isopropyl and n-propyl; especially methyl and ethyl;

branched or unbranched $C_1$–$C_4$-alkoxy such as methoxy, ethoxy, 1-methylethoxy and n-propoxy;

trifluoromethyl;

m is 0, 1, 2, 3 or 4, especially 0, 1 or 2;

n is 0, 1, 2 or 3, especially 0 or 1.

Some α-keto carboxylic esters VII have been disclosed in EP-A 253 213.

α-Keto carboxylic esters of the formula VII′

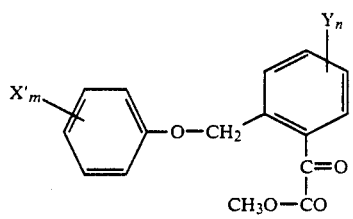

VII′ where X′ and Y are each halogen, $C_1$–$C_4$-alkyl, $C_1$–$C_4$-alkoxy or trifluoromethyl;

m is an integer from 0 to 4;

n is an integer from 0 to 3, with the proviso that n can be 0 only when X′ is 2-chloro, 2-fluoro, 2methyl, 4-methyl, 4-tert-butyl, 2-methoxy or 2-trifluoromethyl and m is 0 or 1, or X′ is 2,4-dichloro or 4-chloro-2-methyl and m is 2, are novel.

Likewise novel are the β-keto sulfoxides obtained from stage (a), of the formula VI

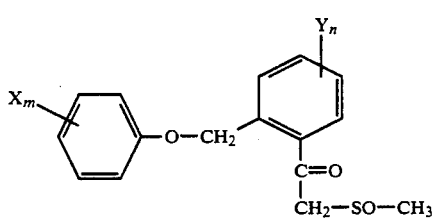

VI where X and Y are each halogen, $C_1$–$C_4$-alkyl, $C_1$–$C_4$-alkoxy or trifluoromethyl;

m is an integer from 0 to 4;

n is an integer from 0 to 3.

Especially suitable methyl α-keto carboxylates VII are to be found in Table 1, and preferred β-keto sulfoxides VI are to be found in Table 2.

TABLE 2

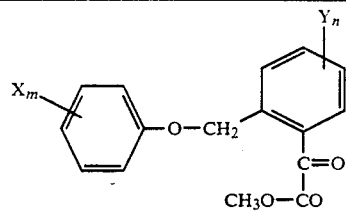

VII

| No. | x | m | y | n |
|---|---|---|---|---|
| 2.001 | — | 0 | — | 0 |
| 2.002 | 2-F | 1 | — | 0 |
| 2.003 | 2-Cl | 1 | — | 0 |
| 2.004 | 3-Cl | 1 | — | 0 |
| 2.005 | 4-Cl | 1 | — | 0 |
| 2.006 | 2,4-$Cl_2$ | 2 | — | 0 |
| 2.007 | 2-$CH_3$, 4-Cl | 2 | — | 0 |
| 2.008 | 2-$CH_3$ | 1 | — | 0 |
| 2.009 | 4-$CH_3$ | 1 | — | 0 |
| 2.010 | 4-tert. $C_4H_9$ | 1 | — | 0 |
| 2.011 | — | — | 3-F | 1 |
| 2.012 | 2-F | 1 | 3-F | 1 |
| 2.013 | 3-F | 1 | 3-F | 1 |
| 2.014 | 4-F | 1 | 3-F | 1 |
| 2.015 | 2-Cl | 1 | 3-F | 1 |
| 2.016 | 3-Cl | 1 | 3-F | 1 |
| 2.017 | 4-Cl | 1 | 3-F | 1 |
| 2.018 | 2-$CH_3$ | 1 | 3-F | 1 |
| 2.019 | 3-$CH_3$ | 1 | 3-F | 1 |
| 2.020 | 4-$CH_3$ | 1 | 3-F | 1 |
| 2.021 | 2-$OCH_3$ | 1 | 3-F | 1 |
| 2.022 | 3-$OCH_3$ | 1 | 3-F | 1 |
| 2.023 | 4-$OCH_3$ | 1 | 3-F | 1 |
| 2.024 | 2-$CF_3$ | 1 | 3-F | 1 |
| 2.025 | 3-$CF_3$ | 1 | 3-F | 1 |
| 2.026 | 4-$CF_3$ | 1 | 3-F | 1 |
| 2.027 | 2,3-$Cl_2$ | 2 | 3-F | 1 |
| 2.028 | 2,4-$Cl_2$ | 2 | 3-F | 1 |
| 2.029 | 2,5-$Cl_2$ | 2 | 3-F | 1 |
| 2.030 | 2,6-$Cl_2$ | 2 | 3-F | 1 |
| 2.031 | 3,4-$Cl_2$ | 2 | 3-F | 1 |
| 2.032 | 3,5-$Cl_2$ | 2 | 3-F | 1 |
| 2.033 | 2-$CH_3$, 4-Cl | 2 | 3-F | 1 |
| 2.034 | 2-Cl, 4-$CH_3$ | 2 | 3-F | 1 |
| 2.035 | 2-$CF_3$, 4-$CH_3$ | 2 | 3-F | 1 |
| 2.036 | 2-$CH_3$, 4-$CF_3$ | 2 | 3-F | 1 |
| 2.037 | — | — | 3-Cl | 1 |
| 2.038 | 2-F | 1 | 3-Cl | 1 |
| 2.039 | 3-F | 1 | 3-Cl | 1 |
| 2.040 | 4-F | 1 | 3-Cl | 1 |
| 2.041 | 2-Cl | 1 | 3-Cl | 1 |
| 2.042 | 3-Cl | 1 | 3-Cl | 1 |
| 2.043 | 4-Cl | 1 | 3-Cl | 1 |
| 2.044 | 2-$CH_3$ | 1 | 3-Cl | 1 |
| 2.045 | 3-$CH_3$ | 1 | 3-Cl | 1 |
| 2.046 | 4-$CH_3$ | 1 | 3-Cl | 1 |
| 2.047 | 2-$OCH_3$ | 1 | 3-Cl | 1 |
| 2.048 | 3-$OCH_3$ | 1 | 3-Cl | 1 |
| 2.049 | 4-$OCH_3$ | 1 | 3-Cl | 1 |
| 2.050 | 2-$CF_3$ | 1 | 3-Cl | 1 |
| 2.051 | 3-$CF_3$ | 1 | 3-Cl | 1 |
| 2.052 | 4-$CF_3$ | 1 | 3-Cl | 1 |
| 2.053 | 2,3-$Cl_2$ | 2 | 3-Cl | 1 |
| 2.054 | 2,4-$Cl_2$ | 2 | 3-Cl | 1 |
| 2.055 | 2,5-$Cl_2$ | 2 | 3-Cl | 1 |
| 2.056 | 2,6-$Cl_2$ | 2 | 3-Cl | 1 |
| 2.057 | 3,4-$Cl_2$ | 2 | 3-Cl | 1 |
| 2.058 | 3,5-$Cl_2$ | 2 | 3-Cl | 1 |
| 2.059 | 2-$CH_3$, 4-Cl | 2 | 3-Cl | 1 |
| 2.060 | 2-Cl, 4-$CH_3$ | 2 | 3-Cl | 1 |
| 2.061 | 2-$CF_3$, 4-$CH_3$ | 2 | 3-Cl | 1 |
| 2.062 | 2-$CH_3$, 4-$CF_3$ | 2 | 3-Cl | 1 |
| 2.063 | — | — | 3-$CH_3$ | 1 |
| 2.064 | 2-F | 1 | 3-$CH_3$ | 1 |
| 2.065 | 3-F | 1 | 3-$CH_3$ | 1 |
| 2.066 | 4-F | 1 | 3-$CH_3$ | 1 |
| 2.067 | 2-Cl | 1 | 3-$CH_3$ | 1 |
| 2.068 | 3-Cl | 1 | 3-$CH_3$ | 1 |
| 2.069 | 4-Cl | 1 | 3-$CH_3$ | 1 |
| 2.070 | 2-$CH_3$ | 1 | 3-$CH_3$ | 1 |

TABLE 2-continued

VII

[Structure: X_m-phenyl-O-CH_2-phenyl-Y_n with C(=O)-O-CH_3 group]

| No. | x | m | y | n |
|---|---|---|---|---|
| 2.071 | 3-CH₃ | 1 | 3-CH₃ | 1 |
| 2.072 | 4-CH₃ | 1 | 3-CH₃ | 1 |
| 2.073 | 2-OCH₃ | 1 | 3-CH₃ | 1 |
| 2.074 | 3-OCH₃ | 1 | 3-CH₃ | 1 |
| 2.075 | 4-OCH₃ | 1 | 3-CH₃ | 1 |
| 2.076 | 2-CF₃ | 1 | 3-CH₃ | 1 |
| 2.077 | 3-CF₃ | 1 | 3-CH₃ | 1 |
| 2.078 | 4-CF₃ | 1 | 3-CH₃ | 1 |
| 2.079 | 2,3-Cl₂ | 2 | 3-CH₃ | 1 |
| 2.080 | 2,4-Cl₂ | 2 | 3-CH₃ | 1 |
| 2.081 | 2,5-Cl₂ | 2 | 3-CH₃ | 1 |
| 2.082 | 2,6-Cl₂ | 2 | 3-CH₃ | 1 |
| 2.083 | 3,4-Cl₂ | 2 | 3-CH₃ | 1 |
| 2.084 | 3,5-Cl₂ | 2 | 3-CH₃ | 1 |
| 2.085 | 2-CH₃, 4-Cl | 2 | 3-CH₃ | 1 |
| 2.086 | 2-Cl, 4-CH₃ | 2 | 3-CH₃ | 1 |
| 2.087 | 2-CF₃, 4-CH₃ | 2 | 3-CH₃ | 1 |
| 2.088 | 2-CH₃, 4-CF₃ | 2 | 3-CH₃ | 1 |
| 2.089 | — | — | 3-OCH₃ | 1 |
| 2.090 | 2-F | 1 | 3-OCH₃ | 1 |
| 2.091 | 3-F | 1 | 3-OCH₃ | 1 |
| 2.092 | 4-F | 1 | 3-OCH₃ | 1 |
| 2.093 | 2-Cl | 1 | 3-OCH₃ | 1 |
| 2.094 | 3-Cl | 1 | 3-OCH₃ | 1 |
| 2.095 | 4-Cl | 1 | 3-OCH₃ | 1 |
| 2.096 | 2-CH₃ | 1 | 3-OCH₃ | 1 |
| 2.097 | 3-CH₃ | 1 | 3-OCH₃ | 1 |
| 2.098 | 4-CH₃ | 1 | 3-OCH₃ | 1 |
| 2.099 | 2-OCH₃ | 1 | 3-OCH₃ | 1 |
| 2.100 | 3-OCH₃ | 1 | 3-OCH₃ | 1 |
| 2.101 | 4-OCH₃ | 1 | 3-OCH₃ | 1 |
| 2.102 | 2-CF₃ | 1 | 3-OCH₃ | 1 |
| 2.103 | 3-CF₃ | 1 | 3-OCH₃ | 1 |
| 2.104 | 4-CF₃ | 1 | 3-OCH₃ | 1 |
| 2.105 | 2,3-Cl₂ | 2 | 3-OCH₃ | 1 |
| 2.106 | 2,4-Cl₂ | 2 | 3-OCH₃ | 1 |
| 2.107 | 2,5-Cl₂ | 2 | 3-OCH₃ | 1 |
| 2.108 | 2,6-Cl₂ | 2 | 3-OCH₃ | 1 |
| 2.109 | 3,4-Cl₂ | 2 | 3-OCH₃ | 1 |
| 2.110 | 3,5-Cl₂ | 2 | 3-OCH₃ | 1 |
| 2.111 | 2-CH₃, 4-Cl | 2 | 3-OCH₃ | 1 |
| 2.112 | 2-Cl, 4-CH₃ | 2 | 3-OCH₃ | 1 |
| 2.113 | 2-CF₃, 4-CH₃ | 2 | 3-OCH₃ | 1 |
| 2.114 | 2-CH₃, 4-CF₃ | 2 | 3-OCH₃ | 1 |
| 2.115 | — | — | 3-CH₃ | 1 |
| 2.116 | 2-F | 1 | 3-CF₃ | 1 |
| 2.117 | 3-F | 1 | 3-CF₃ | 1 |
| 2.118 | 4-F | 1 | 3-CF₃ | 1 |
| 2.119 | 2-Cl | 1 | 3-CF₃ | 1 |
| 2.120 | 3-Cl | 1 | 3-CF₃ | 1 |
| 2.121 | 4-Cl | 1 | 3-CF₃ | 1 |
| 2.122 | 2-CH₃ | 1 | 3-CF₃ | 1 |
| 2.123 | 3-CH₃ | 1 | 3-CF₃ | 1 |
| 2.124 | 4-CH₃ | 1 | 3-CF₃ | 1 |
| 2.125 | 2-OCH₃ | 1 | 3-CF₃ | 1 |
| 2.126 | 3-OCH₃ | 1 | 3-CF₃ | 1 |
| 2.127 | 4-OCH₃ | 1 | 3-CF₃ | 1 |
| 2.128 | 2-CF₃ | 1 | 3-CF₃ | 1 |
| 2.129 | 3-CF₃ | 1 | 3-CF₃ | 1 |
| 2.130 | 4-CF₃ | 1 | 3-CF₃ | 1 |
| 2.131 | 2,3-Cl₂ | 2 | 3-CF₃ | 1 |
| 2.132 | 2,4-Cl₂ | 2 | 3-CF₃ | 1 |
| 2.133 | 2,5-Cl₂ | 2 | 3-CF₃ | 1 |
| 2.134 | 2,6-Cl₂ | 2 | 3-CF₃ | 1 |
| 2.135 | 3,4-Cl₂ | 2 | 3-CF₃ | 1 |
| 2.136 | 3,5-Cl₂ | 2 | 3-CF₃ | 1 |
| 2.137 | 2-CH₃, 4-Cl | 2 | 3-CF₃ | 1 |
| 2.138 | 2-Cl, 4-CH₃ | 2 | 3-CF₃ | 1 |
| 2.139 | 2-CF₃, 4-CH₃ | 2 | 3-CF₃ | 1 |
| 2.140 | 2-CH₃, 4-CF₃ | 2 | 3-CF₃ | 1 |
| 2.141 | — | — | 4-F | 1 |
| 2.142 | 2-F | 1 | 4-F | 1 |
| 2.143 | 3-F | 1 | 4-F | 1 |
| 2.144 | 4-F | 1 | 4-F | 1 |
| 2.145 | 2-Cl | 1 | 4-F | 1 |
| 2.146 | 3-Cl | 1 | 4-F | 1 |
| 2.147 | 4-Cl | 1 | 4-F | 1 |
| 2.148 | 2-CH₃ | 1 | 4-F | 1 |
| 2.149 | 3-CH₃ | 1 | 4-F | 1 |
| 2.150 | 4-CH₃ | 1 | 4-F | 1 |
| 2.151 | 2-OCH₃ | 1 | 4-F | 1 |
| 2.152 | 3-OCH₃ | 1 | 4-F | 1 |
| 2.153 | 4-OCH₃ | 1 | 4-F | 1 |
| 2.154 | 2-CF₃ | 1 | 4-F | 1 |
| 2.155 | 3-CF₃ | 1 | 4-F | 1 |
| 2.156 | 4-CF₃ | 1 | 4-F | 1 |
| 2.157 | 2,3-Cl₂ | 2 | 4-F | 1 |
| 2.158 | 2,4-Cl₂ | 2 | 4-F | 1 |
| 2.159 | 2,5-Cl₂ | 2 | 4-F | 1 |
| 2.160 | 2,6-Cl₂ | 2 | 4-F | 1 |
| 2.161 | 3,4-Cl₂ | 2 | 4-F | 1 |
| 2.162 | 3,5-Cl₂ | 2 | 4-F | 1 |
| 2.163 | 2-CH₃, 4-Cl | 2 | 4-F | 1 |
| 2.164 | 2-Cl, 4-CH₃ | 2 | 4-F | 1 |
| 2.165 | 2-CF₃, 4-CH₃ | 2 | 4-F | 1 |
| 2.166 | 2-CH₃, 4-CF₃ | 2 | 4-F | 1 |
| 2.167 | — | — | 4-Cl | 1 |
| 2.168 | 2-F | 1 | 4-Cl | 1 |
| 2.169 | 3-F | 1 | 4-Cl | 1 |
| 2.170 | 4-F | 1 | 4-Cl | 1 |
| 2.171 | 2-Cl | 1 | 4-Cl | 1 |
| 2.172 | 3-Cl | 1 | 4-Cl | 1 |
| 2.173 | 4-Cl | 1 | 4-Cl | 1 |
| 2.174 | 2-CH₃ | 1 | 4-Cl | 1 |
| 2.175 | 3-CH₃ | 1 | 4-Cl | 1 |
| 2.176 | 4-CH₃ | 1 | 4-Cl | 1 |
| 2.177 | 2-OCH₃ | 1 | 4-Cl | 1 |
| 2.178 | 3-OCH₃ | 1 | 4-Cl | 1 |
| 2.179 | 4-OCH₃ | 1 | 4-Cl | 1 |
| 2.180 | 2-CF₃ | 1 | 4-Cl | 1 |
| 2.181 | 3-CF₃ | 1 | 4-Cl | 1 |
| 2.182 | 4-CF₃ | 1 | 4-Cl | 1 |
| 2.183 | 2,3-Cl₂ | 2 | 4-Cl | 1 |
| 2.184 | 2,4-Cl₂ | 2 | 4-Cl | 1 |
| 2.185 | 2,5-Cl₂ | 2 | 4-Cl | 1 |
| 2.186 | 2,6-Cl₂ | 2 | 4-Cl | 1 |
| 2.187 | 3,4-Cl₂ | 2 | 4-Cl | 1 |
| 2.188 | 3,5-Cl₂ | 2 | 4-Cl | 1 |
| 2.189 | 2-CH₃, 4-Cl | 2 | 4-Cl | 1 |
| 2.190 | 2-Cl, 4-CH₃ | 2 | 4-Cl | 1 |
| 2.191 | 2-CF₃, 4-CH₃ | 2 | 4-Cl | 1 |
| 2.192 | 2-CH₃, 4-CF₃ | 2 | 4-Cl | 1 |
| 2.193 | — | — | 4-Me | 1 |
| 2.194 | 2-F | 1 | 4-Me | 1 |
| 2.195 | 3-F | 1 | 4-Me | 1 |
| 2.196 | 4-F | 1 | 4-Me | 1 |
| 2.197 | 2-Cl | 1 | 4-Me | 1 |
| 2.198 | 3-Cl | 1 | 4-Me | 1 |
| 2.199 | 4-Cl | 1 | 4-Me | 1 |
| 2.200 | 2-CH₃ | 1 | 4-Me | 1 |
| 2.201 | 3-CH₃ | 1 | 4-Me | 1 |
| 2.202 | 4-CH₃ | 1 | 4-Me | 1 |
| 2.203 | 2-OCH₃ | 1 | 4-Me | 1 |
| 2.204 | 3-OCH₃ | 1 | 4-Me | 1 |
| 2.205 | 4-OCH₃ | 1 | 4-Me | 1 |
| 2.206 | 2-CF₃ | 1 | 4-Me | 1 |
| 2.207 | 3-CF₃ | 1 | 4-Me | 1 |
| 2.208 | 4-CF₃ | 1 | 4-Me | 1 |
| 2.209 | 2,3-Cl₂ | 2 | 4-Me | 1 |
| 2.210 | 2,4-Cl₂ | 2 | 4-Me | 1 |

TABLE 2-continued

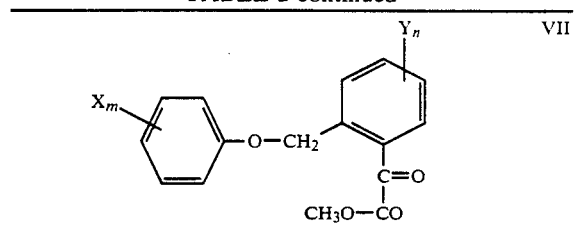

VII

| No. | x | m | y | n |
|---|---|---|---|---|
| 2.211 | 2,5-Cl$_2$ | 2 | 4-Me | 1 |
| 2.212 | 2,6-Cl$_2$ | 2 | 4-Me | 1 |
| 2.213 | 3,4-Cl$_2$ | 2 | 4-Me | 1 |
| 2.214 | 3,5-Cl$_2$ | 2 | 4-Me | 1 |
| 2.215 | 2-CH$_3$, 4-Cl | 2 | 4-Me | 1 |
| 2.216 | 2-Cl, 4-CH$_3$ | 2 | 4-Me | 1 |
| 2.217 | 2-CF$_3$, 4-CH$_3$ | 2 | 4-Me | 1 |
| 2.218 | 2-CH$_3$, 4-CF$_3$ | 2 | 4-Me | 1 |
| 2.219 | — | — | 4-OCH$_3$ | 1 |
| 2.220 | 2-F | 1 | 4-OCH$_3$ | 1 |
| 2.221 | 3-F | 1 | 4-OCH$_3$ | 1 |
| 2.222 | 4-F | 1 | 4-OCH$_3$ | 1 |
| 2.223 | 2-Cl | 1 | 4-OCH$_3$ | 1 |
| 2.224 | 3-Cl | 1 | 4-OCH$_3$ | 1 |
| 2.225 | 4-Cl | 1 | 4-OCH$_3$ | 1 |
| 2.226 | 2-CH$_3$ | 1 | 4-OCH$_3$ | 1 |
| 2.227 | 3-CH$_3$ | 1 | 4-OCH$_3$ | 1 |
| 2.228 | 4-CH$_3$ | 1 | 4-OCH$_3$ | 1 |
| 2.229 | 2-OCH$_3$ | 1 | 4-OCH$_3$ | 1 |
| 2.230 | 3-OCH$_3$ | 1 | 4-OCH$_3$ | 1 |
| 2.231 | 4-OCH$_3$ | 1 | 4-OCH$_3$ | 1 |
| 2.232 | 2-CF$_3$ | 1 | 4-OCH$_3$ | 1 |
| 2.233 | 3-CF$_3$ | 1 | 4-OCH$_3$ | 1 |
| 2.234 | 4-CF$_3$ | 1 | 4-OCH$_3$ | 1 |
| 2.235 | 2,3-Cl$_2$ | 2 | 4-OCH$_3$ | 1 |
| 2.236 | 2,4-Cl$_2$ | 2 | 4-OCH$_3$ | 1 |
| 2.237 | 2,5-Cl$_2$ | 2 | 4-OCH$_3$ | 1 |
| 2.238 | 2,6-Cl$_2$ | 2 | 4-OCH$_3$ | 1 |
| 2.239 | 3,4-Cl$_2$ | 2 | 4-OCH$_3$ | 1 |
| 2.240 | 3,5-Cl$_2$ | 2 | 4-OCH$_3$ | 1 |
| 2.241 | 2-CH$_3$, 4-Cl | 2 | 4-OCH$_3$ | 1 |
| 2.242 | 2-Cl, 4-CH$_3$ | 2 | 4-OCH$_3$ | 1 |
| 2.243 | 2-CF$_3$, 4-CH$_3$ | 2 | 4-OCH$_3$ | 1 |
| 2.244 | 2-CH$_3$, 4-CF$_3$ | 2 | 4-OCH$_3$ | 1 |
| 2.245 | — | — | 4-CF$_3$ | 1 |
| 2.246 | 2-F | 1 | 4-CF$_3$ | 1 |
| 2.247 | 3-F | 1 | 4-CF$_3$ | 1 |
| 2.248 | 4-F | 1 | 4-CF$_3$ | 1 |
| 2.249 | 2-Cl | 1 | 4-CF$_3$ | 1 |
| 2.250 | 3-Cl | 1 | 4-CF$_3$ | 1 |
| 2.251 | 4-Cl | 1 | 4-CF$_3$ | 1 |
| 2.252 | 2-CH$_3$ | 1 | 4-CF$_3$ | 1 |
| 2.253 | 3-CH$_3$ | 1 | 4-CF$_3$ | 1 |
| 2.254 | 4-CH$_3$ | 1 | 4-CF$_3$ | 1 |
| 2.255 | 2-OCH$_3$ | 1 | 4-CF$_3$ | 1 |
| 2.256 | 3-OCH$_3$ | 1 | 4-CF$_3$ | 1 |
| 2.257 | 4-OCH$_3$ | 1 | 4-CF$_3$ | 1 |
| 2.258 | 2-CF$_3$ | 1 | 4-CF$_3$ | 1 |
| 2.259 | 3-CF$_3$ | 1 | 4-CF$_3$ | 1 |
| 2.260 | 4-CF$_3$ | 1 | 4-CF$_3$ | 1 |
| 2.261 | 2,3-Cl$_2$ | 2 | 4-CF$_3$ | 1 |
| 2.262 | 2,4-Cl$_2$ | 2 | 4-CF$_3$ | 1 |
| 2.263 | 2,5-Cl$_2$ | 2 | 4-CF$_3$ | 1 |
| 2.264 | 2,6-Cl$_2$ | 2 | 4-CF$_3$ | 1 |
| 2.265 | 3,4-Cl$_2$ | 2 | 4-CF$_3$ | 1 |
| 2.266 | 3,5-Cl$_2$ | 2 | 4-CF$_3$ | 1 |
| 2.267 | 2-CH$_3$, 4-Cl | 2 | 4-CF$_3$ | 1 |
| 2.268 | 2-Cl, 4-CH$_3$ | 2 | 4-CF$_3$ | 1 |
| 2.269 | 2-CF$_3$, 4-CH$_3$ | 2 | 4-CF$_3$ | 1 |
| 2.270 | 2-CH$_3$, 4-CF$_3$ | 2 | 4-CF$_3$ | 1 |
| 2.271 | — | — | 5-F | 1 |
| 2.272 | 2-F | 1 | 5-F | 1 |
| 2.273 | 3-F | 1 | 5-F | 1 |
| 2.274 | 4-F | 1 | 5-F | 1 |
| 2.275 | 2-Cl | 1 | 5-F | 1 |
| 2.276 | 3-Cl | 1 | 5-F | 1 |
| 2.277 | 4-Cl | 1 | 5-F | 1 |
| 2.278 | 2-CH$_3$ | 1 | 5-F | 1 |
| 2.279 | 3-CH$_3$ | 1 | 5-F | 1 |
| 2.280 | 4-CH$_3$ | 1 | 5-F | 1 |

TABLE 2-continued

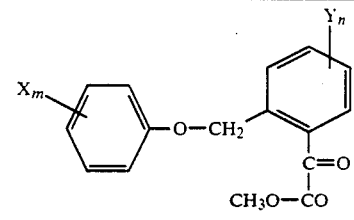

VII

| No. | x | m | y | n |
|---|---|---|---|---|
| 2.281 | 2-OCH$_3$ | 1 | 5-F | 1 |
| 2.282 | 3-OCH$_3$ | 1 | 5-F | 1 |
| 2.283 | 4-OCH$_3$ | 1 | 5-F | 1 |
| 2.284 | 2-CF$_3$ | 1 | 5-F | 1 |
| 2.285 | 3-CF$_3$ | 1 | 5-F | 1 |
| 2.286 | 4-CF$_3$ | 1 | 5-F | 1 |
| 2.287 | 2,3-Cl$_2$ | 2 | 5-F | 1 |
| 2.288 | 2,4-Cl$_2$ | 2 | 5-F | 1 |
| 2.289 | 2,5-Cl$_2$ | 2 | 5-F | 1 |
| 2.290 | 2,6-Cl$_2$ | 2 | 5-F | 1 |
| 2.291 | 3,4-Cl$_2$ | 2 | 5-F | 1 |
| 2.292 | 3,5-Cl$_2$ | 2 | 5-F | 1 |
| 2.293 | 2-CH$_3$, 4-Cl | 2 | 5-F | 1 |
| 2.294 | 2-Cl, 4-CH$_3$ | 2 | 5-F | 1 |
| 2.295 | 2-CF$_3$, 4-CH$_3$ | 2 | 5-F | 1 |
| 2.296 | 2-CH$_3$, 4-CF$_3$ | 2 | 5-F | 1 |
| 2.297 | — | — | 5-Cl | 1 |
| 2.298 | 2-F | 1 | 5-Cl | 1 |
| 2.299 | 3-F | 1 | 5-Cl | 1 |
| 2.300 | 4-F | 1 | 5-Cl | 1 |
| 2.301 | 2-Cl | 1 | 5-Cl | 1 |
| 2.302 | 3-Cl | 1 | 5-Cl | 1 |
| 2.303 | 4-Cl | 1 | 5-Cl | 1 |
| 2.304 | 2-CH$_3$ | 1 | 5-Cl | 1 |
| 2.305 | 3-CH$_3$ | 1 | 5-Cl | 1 |
| 2.306 | 4-CH$_3$ | 1 | 5-Cl | 1 |
| 2.307 | 2-OCH$_3$ | 1 | 5-Cl | 1 |
| 2.308 | 3-OCH$_3$ | 1 | 5-Cl | 1 |
| 2.309 | 4-OCH$_3$ | 1 | 5-Cl | 1 |
| 2.310 | 2-CF$_3$ | 1 | 5-Cl | 1 |
| 2.311 | 3-CF$_3$ | 1 | 5-Cl | 1 |
| 2.312 | 4-CF$_3$ | 1 | 5-Cl | 1 |
| 2.313 | 2,3-Cl$_2$ | 2 | 5-Cl | 1 |
| 2.314 | 2,4-Cl$_2$ | 2 | 5-Cl | 1 |
| 2.315 | 2,5-Cl$_2$ | 2 | 5-Cl | 1 |
| 2.316 | 2,6-Cl$_2$ | 2 | 5-Cl | 1 |
| 2.317 | 3,4-Cl$_2$ | 2 | 5-Cl | 1 |
| 2.318 | 3,5-Cl$_2$ | 2 | 5-Cl | 1 |
| 2.319 | 2-CH$_3$, 4-Cl | 2 | 5-Cl | 1 |
| 2.320 | 2-Cl, 4-CH$_3$ | 2 | 5-Cl | 1 |
| 2.321 | 2-CF$_3$, 4-CH$_3$ | 2 | 5-Cl | 1 |
| 2.322 | 2-CH$_3$, 4-CF$_3$ | 2 | 5-Cl | 1 |
| 2.323 | — | — | 5-Me | 1 |
| 2.324 | 2-F | 1 | 5-Me | 1 |
| 2.325 | 3-F | 1 | 5-Me | 1 |
| 2.326 | 4-F | 1 | 5-Me | 1 |
| 2.327 | 2-Cl | 1 | 5-Me | 1 |
| 2.328 | 3-Cl | 1 | 5-Me | 1 |
| 2.329 | 4-Cl | 1 | 5-Me | 1 |
| 2.330 | 2-CH$_3$ | 1 | 5-Me | 1 |
| 2.331 | 3-CH$_3$ | 1 | 5-Me | 1 |
| 2.332 | 4-CH$_3$ | 1 | 5-Me | 1 |
| 2.333 | 2-OCH$_3$ | 1 | 5-Me | 1 |
| 2.334 | 3-OCH$_3$ | 1 | 5-Me | 1 |
| 2.335 | 4-OCH$_3$ | 1 | 5-Me | 1 |
| 2.336 | 2-CF$_3$ | 1 | 5-Me | 1 |
| 2.337 | 3-CF$_3$ | 1 | 5-Me | 1 |
| 2.338 | 4-CF$_3$ | 1 | 5-Me | 1 |
| 2.339 | 2,3-Cl$_2$ | 2 | 5-Me | 1 |
| 2.340 | 2,4-Cl$_2$ | 2 | 5-Me | 1 |
| 2.341 | 2,5-Cl$_2$ | 2 | 5-Me | 1 |
| 2.342 | 2,6-Cl$_2$ | 2 | 5-Me | 1 |
| 2.343 | 3,4-Cl$_2$ | 2 | 5-Me | 1 |
| 2.344 | 3,5-Cl$_2$ | 2 | 5-Me | 1 |
| 2.345 | 2-CH$_3$, 4-Cl | 2 | 5-Me | 1 |
| 2.346 | 2-Cl, 4-CH$_3$ | 2 | 5-Me | 1 |
| 2.347 | 2-CF$_3$, 4-CH$_3$ | 2 | 5-Me | 1 |
| 2.348 | 2-CH$_3$, 4-CF$_3$ | 2 | 5-Me | 1 |
| 2.349 | — | — | 5-OCH$_3$ | 1 |
| 2.350 | 2-F | 1 | 5-OCH$_3$ | 1 |

TABLE 2-continued

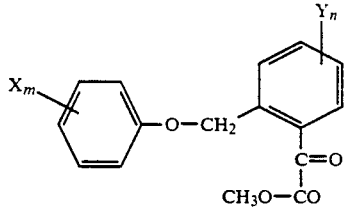

| No. | x | m | y | n |
|---|---|---|---|---|
| 2.351 | 3-F | 1 | 5-OCH₃ | 1 |
| 2.352 | 4-F | 1 | 5-OCH₃ | 1 |
| 2.353 | 2-Cl | 1 | 5-OCH₃ | 1 |
| 2.354 | 3-Cl | 1 | 5-OCH₃ | 1 |
| 2.355 | 4-Cl | 1 | 5-OCH₃ | 1 |
| 2.356 | 2-CH₃ | 1 | 5-OCH₃ | 1 |
| 2.357 | 3-CH₃ | 1 | 5-OCH₃ | 1 |
| 2.358 | 4-CH₃ | 1 | 5-OCH₃ | 1 |
| 2.359 | 2-OCH₃ | 1 | 5-OCH₃ | 1 |
| 2.360 | 3-OCH₃ | 1 | 5-OCH₃ | 1 |
| 2.361 | 4-OCH₃ | 1 | 5-OCH₃ | 1 |
| 2.362 | 2-CF₃ | 1 | 5-OCH₃ | 1 |
| 2.363 | 3-CF₃ | 1 | 5-OCH₃ | 1 |
| 2.364 | 4-CF₃ | 1 | 5-OCH₃ | 1 |
| 2.365 | 2,3-Cl₂ | 2 | 5-OCH₃ | 1 |
| 2.366 | 2,4-Cl₂ | 2 | 5-OCH₃ | 1 |
| 2.367 | 2,5-Cl₂ | 2 | 5-OCH₃ | 1 |
| 2.368 | 2,6-Cl₂ | 2 | 5-OCH₃ | 1 |
| 2.369 | 3,4-Cl₂ | 2 | 5-OCH₃ | 1 |
| 2.370 | 3,5-Cl₂ | 2 | 5-OCH₃ | 1 |
| 2.371 | 2-CH₃, 4-Cl | 2 | 5-OCH₃ | 1 |
| 2.372 | 2-Cl, 4-CH₃ | 2 | 5-OCH₃ | 1 |
| 2.373 | 2-CF₃, 4-CH₃ | 2 | 5-OCH₃ | 1 |
| 2.374 | 2-CH₃, 4-CF₃ | 2 | 5-OCH₃ | 1 |
| 2.375 | — | — | 5-CF₃ | 1 |
| 2.376 | 2-F | 1 | 5-CF₃ | 1 |
| 2.377 | 3-F | 1 | 5-CF₃ | 1 |
| 2.378 | 4-F | 1 | 5-CF₃ | 1 |
| 2.379 | 2-Cl | 1 | 5-CF₃ | 1 |
| 2.380 | 3-Cl | 1 | 5-CF₃ | 1 |
| 2.381 | 4-Cl | 1 | 5-CF₃ | 1 |
| 2.382 | 2-CH₃ | 1 | 5-CF₃ | 1 |
| 2.383 | 3-CH₃ | 1 | 5-CF₃ | 1 |
| 2.384 | 4-CH₃ | 1 | 5-CF₃ | 1 |
| 2.385 | 2-OCH₃ | 1 | 5-CF₃ | 1 |
| 2.386 | 3-OCH₃ | 1 | 5-CF₃ | 1 |
| 2.387 | 4-OCH₃ | 1 | 5-CF₃ | 1 |
| 2.388 | 2-CF₃ | 1 | 5-CF₃ | 1 |
| 2.389 | 3-CF₃ | 1 | 5-CF₃ | 1 |
| 2.390 | 4-CF₃ | 1 | 5-CF₃ | 1 |
| 2.391 | 2,3-Cl₂ | 2 | 5-CF₃ | 1 |
| 2.392 | 2,4-Cl₂ | 2 | 5-CF₃ | 1 |
| 2.393 | 2,5-Cl₂ | 2 | 5-CF₃ | 1 |
| 2.394 | 2,6-Cl₂ | 2 | 5-CF₃ | 1 |
| 2.395 | 3,4-Cl₂ | 2 | 5-CF₃ | 1 |
| 2.396 | 3,5-Cl₂ | 2 | 5-CF₃ | 1 |
| 2.397 | 2-CH₃, 4-Cl | 2 | 5-CF₃ | 1 |
| 2.398 | 2-Cl, 4-CH₃ | 2 | 5-CF₃ | 1 |
| 2.399 | 2-CF₃, 4-CH₃ | 2 | 5-CF₃ | 1 |
| 2.400 | 2-CH₃, 4-CF₃ | 2 | 5-CF₃ | 1 |
| 2.401 | — | — | 6-F | 1 |
| 2.402 | 2-F | 1 | 6-F | 1 |
| 2.403 | 3-F | 1 | 6-F | 1 |
| 2.404 | 4-F | 1 | 6-F | 1 |
| 2.405 | 2-Cl | 1 | 6-F | 1 |
| 2.406 | 3-Cl | 1 | 6-F | 1 |
| 2.407 | 4-Cl | 1 | 6-F | 1 |
| 2.408 | 2-CH₃ | 1 | 6-F | 1 |
| 2.409 | 3-CH₃ | 1 | 6-F | 1 |
| 2.410 | 4-CH₃ | 1 | 6-F | 1 |
| 2.411 | 2-OCH₃ | 1 | 6-F | 1 |
| 2.412 | 3-OCH₃ | 1 | 6-F | 1 |
| 2.413 | 4-OCH₃ | 1 | 6-F | 1 |
| 2.414 | 2-CF₃ | 1 | 6-F | 1 |
| 2.415 | 3-CF₃ | 1 | 6-F | 1 |
| 2.416 | 4-CF₃ | 1 | 6-F | 1 |
| 2.417 | 2,3-Cl₂ | 2 | 6-F | 1 |
| 2.418 | 2,4-Cl₂ | 2 | 6-F | 1 |
| 2.419 | 2,5-Cl₂ | 2 | 6-F | 1 |
| 2.420 | 2,6-Cl₂ | 2 | 6-F | 1 |

TABLE 2-continued

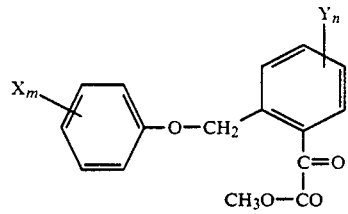

| No. | x | m | y | n |
|---|---|---|---|---|
| 2.421 | 3,4-Cl₂ | 2 | 6-F | 1 |
| 2.422 | 3,5-Cl₂ | 2 | 6-F | 1 |
| 2.423 | 2-CH₃, 4-Cl | 2 | 6-F | 1 |
| 2.424 | 2-Cl, 4-CH₃ | 2 | 6-F | 1 |
| 2.425 | 2-CF₃, 4-CH₃ | 2 | 6-F | 1 |
| 2.426 | 2-CH₃, 4-CF₃ | 2 | 6-F | 1 |
| 2.427 | — | — | 6-Cl | 1 |
| 2.428 | 2-F | 1 | 6-Cl | 1 |
| 2.429 | 3-F | 1 | 6-Cl | 1 |
| 2.430 | 4-F | 1 | 6-Cl | 1 |
| 2.431 | 2-Cl | 1 | 6-Cl | 1 |
| 2.432 | 3-Cl | 1 | 6-Cl | 1 |
| 2.433 | 4-Cl | 1 | 6-Cl | 1 |
| 2.434 | 2-CH₃ | 1 | 6-Cl | 1 |
| 2.435 | 3-CH₃ | 1 | 6-Cl | 1 |
| 2.436 | 4-CH₃ | 1 | 6-Cl | 1 |
| 2.437 | 2-OCH₃ | 1 | 6-Cl | 1 |
| 2.438 | 3-OCH₃ | 1 | 6-Cl | 1 |
| 2.439 | 4-OCH₃ | 1 | 6-Cl | 1 |
| 2.440 | 2-CF₃ | 1 | 6-Cl | 1 |
| 2.441 | 3-CF₃ | 1 | 6-Cl | 1 |
| 2.442 | 4-CF₃ | 1 | 6-Cl | 1 |
| 2.443 | 2,3-Cl₂ | 2 | 6-Cl | 1 |
| 2.444 | 2,4-Cl₂ | 2 | 6-Cl | 1 |
| 2.445 | 2,5-Cl₂ | 2 | 6-Cl | 1 |
| 2.446 | 2,6-Cl₂ | 2 | 6-Cl | 1 |
| 2.447 | 3,4-Cl₂ | 2 | 6-Cl | 1 |
| 2.448 | 3,5-Cl₂ | 2 | 6-Cl | 1 |
| 2.449 | 2-CH₃, 4-Cl | 2 | 6-Cl | 1 |
| 2.450 | 2-Cl, 4-CH₃ | 2 | 6-Cl | 1 |
| 2.451 | 2-CF₃, 4-CH₃ | 2 | 6-Cl | 1 |
| 2.452 | 2-CH₃, 4-CF₃ | 2 | 6-Cl | 1 |
| 2.453 | — | — | 6-CH₃ | 1 |
| 2.454 | 2-F | 1 | 6-CH₃ | 1 |
| 2.455 | 3-F | 1 | 6-CH₃ | 1 |
| 2.456 | 4-F | 1 | 6-CH₃ | 1 |
| 2.457 | 2-Cl | 1 | 6-CH₃ | 1 |
| 2.458 | 3-Cl | 1 | 6-CH₃ | 1 |
| 2.459 | 4-Cl | 1 | 6-CH₃ | 1 |
| 2.460 | 2-CH₃ | 1 | 6-CH₃ | 1 |
| 2.461 | 3-CH₃ | 1 | 6-CH₃ | 1 |
| 2.462 | 4-CH₃ | 1 | 6-CH₃ | 1 |
| 2.463 | 2-OCH₃ | 1 | 6-CH₃ | 1 |
| 2.464 | 3-OCH₃ | 1 | 6-CH₃ | 1 |
| 2.465 | 4-OCH₃ | 1 | 6-CH₃ | 1 |
| 2.466 | 2-CF₃ | 1 | 6-CH₃ | 1 |
| 2.467 | 3-CF₃ | 1 | 6-CH₃ | 1 |
| 2.468 | 4-CF₃ | 1 | 6-CH₃ | 1 |
| 2.469 | 2,3-Cl₂ | 2 | 6-CH₃ | 1 |
| 2.470 | 2,4-Cl₂ | 2 | 6-CH₃ | 1 |
| 2.471 | 2,5-Cl₂ | 2 | 6-CH₃ | 1 |
| 2.472 | 2,6-Cl₂ | 2 | 6-CH₃ | 1 |
| 2.473 | 3,4-Cl₂ | 2 | 6-CH₃ | 1 |
| 2.474 | 3,5-Cl₂ | 2 | 6-CH₃ | 1 |
| 2.475 | 2-CH₃, 4-Cl | 2 | 6-CH₃ | 1 |
| 2.476 | 2-Cl, 4-CH₃ | 2 | 6-CH₃ | 1 |
| 2.477 | 2-CF₃, 4-CH₃ | 2 | 6-CH₃ | 1 |
| 2.478 | 2-CH₃, 4-CF₃ | 2 | 6-CH₃ | 1 |
| 2.479 | — | — | 6-OCH₃ | 1 |
| 2.448 | 2-F | 1 | 6-OCH₃ | 1 |
| 2.481 | 3-F | 1 | 6-OCH₃ | 1 |
| 2.482 | 4-F | 1 | 6-OCH₃ | 1 |
| 2.483 | 2-Cl | 1 | 6-OCH₃ | 1 |
| 2.484 | 3-Cl | 1 | 6-OCH₃ | 1 |
| 2.485 | 4-Cl | 1 | 6-OCH₃ | 1 |
| 2.486 | 2-CH₃ | 1 | 6-OCH₃ | 1 |
| 2.487 | 3-CH₃ | 1 | 6-OCH₃ | 1 |
| 2.488 | 4-CH₃ | 1 | 6-OCH₃ | 1 |
| 2.489 | 2-OCH₃ | 1 | 6-OCH₃ | 1 |
| 2.490 | 3-OCH₃ | 1 | 6-OCH₃ | 1 |

TABLE 2-continued

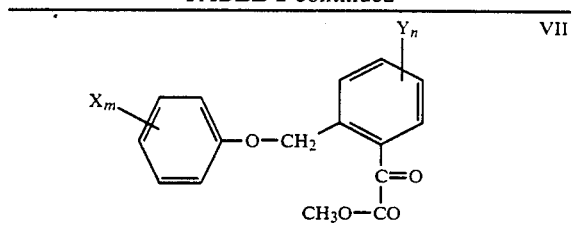

VII

| No. | x | m | y | n |
|---|---|---|---|---|
| 2.491 | 4-OCH₃ | 1 | 6-OCH₃ | 1 |
| 2.492 | 2-CF₃ | 1 | 6-OCH₃ | 1 |
| 2.493 | 3-CF₃ | 1 | 6-OCH₃ | 1 |
| 2.494 | 4-CF₃ | 1 | 6-OCH₃ | 1 |
| 2.495 | 2,3-Cl₂ | 2 | 6-OCH₃ | 1 |
| 2.496 | 2,4-Cl₂ | 2 | 6-OCH₃ | 1 |
| 2.497 | 2,5-Cl₂ | 2 | 6-OCH₃ | 1 |
| 2.498 | 2,6-Cl₂ | 2 | 6-OCH₃ | 1 |
| 2.499 | 3,4-Cl₂ | 2 | 6-OCH₃ | 1 |
| 2.500 | 3,5-Cl₂ | 2 | 6-OCH₃ | 1 |
| 2.501 | 2-CH₃, 4-Cl | 2 | 6-OCH₃ | 1 |
| 2.502 | 2-Cl, 4-CH₃ | 2 | 6-OCH₃ | 1 |
| 2.503 | 2-CF₃, 4-CH₃ | 2 | 6-OCH₃ | 1 |
| 2.504 | 2-CH₃, 4-CF₃ | 2 | 6-OCH₃ | 1 |
| 2.505 | — | — | 6-CF₃ | 1 |
| 2.506 | 2-F | 1 | 6-CF₃ | 1 |
| 2.507 | 3-F | 1 | 6-CF₃ | 1 |
| 2.508 | 4-F | 1 | 6-CF₃ | 1 |
| 2.509 | 2-Cl | 1 | 6-CF₃ | 1 |
| 2.510 | 3-Cl | 1 | 6-CF₃ | 1 |
| 2.511 | 4-Cl | 1 | 6-CF₃ | 1 |
| 2.512 | 2-CH₃ | 1 | 6-CF₃ | 1 |
| 2.513 | 3-CH₃ | 1 | 6-CF₃ | 1 |
| 2.514 | 4-CH₃ | 1 | 6-CF₃ | 1 |
| 2.515 | 2-OCH₃ | 1 | 6-CF₃ | 1 |
| 2.516 | 3-OCH₃ | 1 | 6-CF₃ | 1 |
| 2.517 | 4-OCH₃ | 1 | 6-CF₃ | 1 |
| 2.518 | 2-CF₃ | 1 | 6-CF₃ | 1 |
| 2.519 | 3-CF₃ | 1 | 6-CF₃ | 1 |
| 2.520 | 4-CF₃ | 1 | 6-CF₃ | 1 |
| 2.521 | 2,3-Cl₂ | 2 | 6-CF₃ | 1 |
| 2.522 | 2,4-Cl₂ | 2 | 6-CF₃ | 1 |
| 2.523 | 2,5-Cl₂ | 2 | 6-CF₃ | 1 |
| 2.524 | 2,6-Cl₂ | 2 | 6-CF₃ | 1 |
| 2.525 | 3,4-Cl₂ | 2 | 6-CF₃ | 1 |
| 2.526 | 3,5-Cl₂ | 2 | 6-CF₃ | 1 |
| 2.527 | 2-CH₃, 4-Cl | 2 | 6-CF₃ | 1 |
| 2.528 | 2-Cl, 4-CH₃ | 2 | 6-CF₃ | 1 |
| 2.529 | 2-CF₃, 4-CH₃ | 2 | 6-CF₃ | 1 |
| 2.530 | 2-CH₃, 4-CF₃ | 2 | 6-CF₃ | 1 |
| 2.531 | — | — | 3,5-Cl₂ | 1 |
| 2.532 | 2-F | 1 | 3,5-Cl₂ | 1 |
| 2.533 | 3-F | 1 | 3,5-Cl₂ | 1 |
| 2.534 | 4-F | 1 | 3,5-Cl₂ | 1 |
| 2.535 | 2-Cl | 1 | 3,5-Cl₂ | 1 |
| 2.536 | 3-Cl | 1 | 3,5-Cl₂ | 1 |
| 2.537 | 4-Cl | 1 | 3,5-Cl₂ | 1 |
| 2.538 | 2-CH₃ | 1 | 3,5-Cl₂ | 1 |
| 2.539 | 3-CH₃ | 1 | 3,5-Cl₂ | 1 |
| 2.540 | 4-CH₃ | 1 | 3,5-Cl₂ | 1 |
| 2.541 | 2-OCH₃ | 1 | 3,5-Cl₂ | 1 |
| 2.542 | 3-OCH₃ | 1 | 3,5-Cl₂ | 1 |
| 2.543 | 4-OCH₃ | 1 | 3,5-Cl₂ | 1 |
| 2.544 | 2-CF₃ | 1 | 3,5-Cl₂ | 1 |
| 2.545 | 3-CF₃ | 1 | 3,5-Cl₂ | 1 |
| 2.546 | 4-CF₃ | 1 | 3,5-Cl₂ | 1 |
| 2.547 | 2,3-Cl₂ | 2 | 3,5-Cl₂ | 1 |
| 2.548 | 2,4-Cl₂ | 2 | 3,5-Cl₂ | 1 |
| 2.549 | 2,5-Cl₂ | 2 | 3,5-Cl₂ | 1 |
| 2.550 | 2,6-Cl₂ | 2 | 3,5-Cl₂ | 1 |
| 2.551 | 3,4-Cl₂ | 2 | 3,5-Cl₂ | 1 |
| 2.552 | 3,5-Cl₂ | 2 | 3,5-Cl₂ | 1 |
| 2.553 | 2-CH₃, 4-Cl | 2 | 3,5-Cl₂ | 1 |
| 2.554 | 2-Cl, 4-CH₃ | 2 | 3,5-Cl₂ | 1 |
| 2.555 | 2-CF₃, 4-CH₃ | 2 | 3,5-Cl₂ | 1 |
| 2.556 | 2-CH₃, 4-CF₃ | 2 | 3,5-Cl₂ | 1 |
| 2.557 | — | — | 3-Cl, 5-F | 1 |
| 2.558 | 2-F | 1 | 3-Cl, 5-F | 1 |
| 2.559 | 3-F | 1 | 3-Cl, 5-F | 1 |
| 2.560 | 4-F | 1 | 3-Cl, 5-F | 1 |
| 2.561 | 2-Cl | 1 | 3-Cl, 5-F | 1 |
| 2.562 | 3-Cl | 1 | 3-Cl, 5-F | 1 |
| 2.563 | 4-Cl | 1 | 3-Cl, 5-F | 1 |
| 2.564 | 2-CH₃ | 1 | 3-Cl, 5-F | 1 |
| 2.565 | 3-CH₃ | 1 | 3-Cl, 5-F | 1 |
| 2.566 | 4-CH₃ | 1 | 3-Cl, 5-F | 1 |
| 2.567 | 2-OCH₃ | 1 | 3-Cl, 5-F | 1 |
| 2.568 | 3-OCH₃ | 1 | 3-Cl, 5-F | 1 |
| 2.569 | 4-OCH₃ | 1 | 3-Cl, 5-F | 1 |
| 2.570 | 2-CF₃ | 1 | 3-Cl, 5-F | 1 |
| 2.571 | 3-CF₃ | 1 | 3-Cl, 5-F | 1 |
| 2.572 | 4-CF₃ | 1 | 3-Cl, 5-F | 1 |
| 2.573 | 2,3-Cl₂ | 2 | 3-Cl, 5-F | 1 |
| 2.574 | 2,4-Cl₂ | 2 | 3-Cl, 5-F | 1 |
| 2.575 | 2,5-Cl₂ | 2 | 3-Cl, 5-F | 1 |
| 2.576 | 2,6-Cl₂ | 2 | 3-Cl, 5-F | 1 |
| 2.577 | 3,4-Cl₂ | 2 | 3-Cl, 5-F | 1 |
| 2.578 | 3,5-Cl₂ | 2 | 3-Cl, 5-F | 1 |
| 2.579 | 2-CH₃, 4-Cl | 2 | 3-Cl, 5-F | 1 |
| 2.580 | 2-Cl, 4-CH₃ | 2 | 3-Cl, 5-F | 1 |
| 2.581 | 2-CF₃, 4-CH₃ | 2 | 3-Cl, 5-F | 1 |
| 2.582 | 2-CH₃, 4-CF₃ | 2 | 3-Cl, 5-F | 1 |
| 2.583 | — | — | 3-F, 5-Cl | 1 |
| 2.584 | 2-F | 1 | 3-F, 5-Cl | 1 |
| 2.585 | 3-F | 1 | 3-F, 5-Cl | 1 |
| 2.586 | 4-F | 1 | 3-F, 5-Cl | 1 |
| 2.587 | 2-Cl | 1 | 3-F, 5-Cl | 1 |
| 2.588 | 3-Cl | 1 | 3-F, 5-Cl | 1 |
| 2.589 | 4-Cl | 1 | 3-F, 5-Cl | 1 |
| 2.590 | 2-CH₃ | 1 | 3-F, 5-Cl | 1 |
| 2.591 | 3-CH₃ | 1 | 3-F, 5-Cl | 1 |
| 2.592 | 4-CH₃ | 1 | 3-F, 5-Cl | 1 |
| 2.593 | 2-OCH₃ | 1 | 3-F, 5-Cl | 1 |
| 2.594 | 3-OCH₃ | 1 | 3-F, 5-Cl | 1 |
| 2.595 | 4-OCH₃ | 1 | 3-F, 5-Cl | 1 |
| 2.596 | 2-CF₃ | 1 | 3-F, 5-Cl | 1 |
| 2.597 | 3-CF₃ | 1 | 3-F, 5-Cl | 1 |
| 2.598 | 4-CF₃ | 1 | 3-F, 5-Cl | 1 |
| 2.599 | 2,3-Cl₂ | 2 | 3-F, 5-Cl | 1 |
| 2.600 | 2,4-Cl₂ | 2 | 3-F, 5-Cl | 1 |
| 2.601 | 2,5-Cl₂ | 2 | 3-F, 5-Cl | 1 |
| 2.602 | 2,6-Cl₂ | 2 | 3-F, 5-Cl | 1 |
| 2.603 | 3,4-Cl₂ | 2 | 3-F, 5-Cl | 1 |
| 2.604 | 3,5-Cl₂ | 2 | 3-F, 5-Cl | 1 |
| 2.605 | 2-CH₃, 4-Cl | 2 | 3-F, 5-Cl | 1 |
| 2.606 | 2-Cl, 4-CH₃ | 2 | 3-F, 5-Cl | 1 |
| 2.607 | 2-CF₃, 4-CH₃ | 2 | 3-F, 5-Cl | 1 |
| 2.608 | 2-CH₃, 4-CF₃ | 2 | 3-F, 5-Cl | 1 |
| 2.609 | — | — | 3,5,6-F₃ | 1 |
| 2.610 | 2-F | 1 | 3,5,6-F₃ | 1 |
| 2.611 | 3-F | 1 | 3,5,6-F₃ | 1 |
| 2.612 | 4-F | 1 | 3,5,6-F₃ | 1 |
| 2.613 | 2-Cl | 1 | 3,5,6-F₃ | 1 |
| 2.614 | 3-Cl | 1 | 3,5,6-F₃ | 1 |
| 2.615 | 4-Cl | 1 | 3,5,6-F₃ | 1 |
| 2.616 | 2-CH₃ | 1 | 3,5,6-F₃ | 1 |
| 2.617 | 3-CH₃ | 1 | 3,5,6-F₃ | 1 |
| 2.618 | 4-CH₃ | 1 | 3,5,6-F₃ | 1 |
| 2.619 | 2-OCH₃ | 1 | 3,5,6-F₃ | 1 |
| 2.620 | 3-OCH₃ | 1 | 3,5,6-F₃ | 1 |
| 2.621 | 4-OCH₃ | 1 | 3,5,6-F₃ | 1 |
| 2.622 | 2-CF₃ | 1 | 3,5,6-F₃ | 1 |
| 2.623 | 3-CF₃ | 1 | 3,5,6-F₃ | 1 |
| 2.624 | 4-CF₃ | 1 | 3,5,6-F₃ | 1 |
| 2.625 | 2,3-Cl₂ | 2 | 3,5,6-F₃ | 1 |
| 2.626 | 2,4-Cl₂ | 2 | 3,5,6-F₃ | 1 |
| 2.627 | 2,5-Cl₂ | 2 | 3,5,6-F₃ | 1 |
| 2.628 | 2,6-Cl₂ | 2 | 3,5,6-F₃ | 1 |
| 2.629 | 3,4-Cl₂ | 2 | 3,5,6-F₃ | 1 |
| 2.630 | 3,5-Cl₂ | 2 | 3,5,6-F₃ | 1 |

TABLE 2-continued

Structure VII: Ar(X_m)–O–CH$_2$–Ar'(Y_n)–C(=O)–CO–OCH$_3$

| No. | x | m | y | n |
|---|---|---|---|---|
| 2.631 | 2-CH$_3$, 4-Cl | 2 | 3,5,6-F$_3$ | 1 |
| 2.632 | 2-Cl, 4-CH$_3$ | 2 | 3,5,6-F$_3$ | 1 |
| 2.633 | 2-CF$_3$, 4-CH$_3$ | 2 | 3,5,6-F$_3$ | 1 |
| 2.634 | 2-CH$_3$, 4-CF$_3$ | 2 | 3,5,6-F$_3$ | 1 |
| 2.635 | — | — | 3,5-(CH$_3$)$_2$ | 1 |
| 2.636 | 2-F | 1 | 3,5-(CH$_3$)$_2$ | 1 |
| 2.637 | 3-F | 1 | 3,5-(CH$_3$)$_2$ | 1 |
| 2.638 | 4-F | 1 | 3,5-(CH$_3$)$_2$ | 1 |
| 2.639 | 2-Cl | 1 | 3,5-(CH$_3$)$_2$ | 1 |
| 2.640 | 3-Cl | 1 | 3,5-(CH$_3$)$_2$ | 1 |
| 2.641 | 4-Cl | 1 | 3,5-(CH$_3$)$_2$ | 1 |
| 2.642 | 2-CH$_3$ | 1 | 3,5-(CH$_3$)$_2$ | 1 |
| 2.643 | 3-CH$_3$ | 1 | 3,5-(CH$_3$)$_2$ | 1 |
| 2.644 | 4-CH$_3$ | 1 | 3,5-(CH$_3$)$_2$ | 1 |
| 2.645 | 2-OCH$_3$ | 1 | 3,5-(CH$_3$)$_2$ | 1 |
| 2.646 | 3-OCH$_3$ | 1 | 3,5-(CH$_3$)$_2$ | 1 |
| 2.647 | 4-OCH$_3$ | 1 | 3,5-(CH$_3$)$_2$ | 1 |
| 2.648 | 2-CF$_3$ | 1 | 3,5-(CH$_3$)$_2$ | 1 |
| 2.649 | 3-CF$_3$ | 1 | 3,5-(CH$_3$)$_2$ | 1 |
| 2.650 | 4-CF$_3$ | 1 | 3,5-(CH$_3$)$_2$ | 1 |
| 2.651 | 2,3-Cl$_2$ | 2 | 3,5-(CH$_3$)$_2$ | 1 |
| 2.652 | 2,4-Cl$_2$ | 2 | 3,5-(CH$_3$)$_2$ | 1 |
| 2.653 | 2,5-Cl$_2$ | 2 | 3,5-(CH$_3$)$_2$ | 1 |
| 2.654 | 2,6-Cl$_2$ | 2 | 3,5-(CH$_3$)$_2$ | 1 |
| 2.655 | 3,4-Cl$_2$ | 2 | 3,5-(CH$_3$)$_2$ | 1 |
| 2.656 | 3,5-Cl$_2$ | 2 | 3,5-(CH$_3$)$_2$ | 1 |
| 2.657 | 2-CH$_3$, 4-Cl | 2 | 3,5-(CH$_3$)$_2$ | 1 |
| 2.658 | 2-Cl, 4-CH$_3$ | 2 | 3,5-(CH$_3$)$_2$ | 1 |
| 2.659 | 2-CF$_3$, 4-CH$_3$ | 2 | 3,5-(CH$_3$)$_2$ | 1 |
| 2.660 | 2-CH$_3$, 4-CF$_3$ | 2 | 3,5-(CH$_3$)$_2$ | 1 |
| 2.661 | — | — | 5,6-(CH$_3$)$_2$ | 1 |
| 2.662 | 2-F | 1 | 5,6-(CH$_3$)$_2$ | 1 |
| 2.663 | 3-F | 1 | 5,6-(CH$_3$)$_2$ | 1 |
| 2.664 | 4-F | 1 | 5,6-(CH$_3$)$_2$ | 1 |
| 2.665 | 2-Cl | 1 | 5,6-(CH$_3$)$_2$ | 1 |
| 2.666 | 3-Cl | 1 | 5,6-(CH$_3$)$_2$ | 1 |
| 2.667 | 4-Cl | 1 | 5,6-(CH$_3$)$_2$ | 1 |
| 2.668 | 2-CH$_3$ | 1 | 5,6-(CH$_3$)$_2$ | 1 |
| 2.669 | 3-CH$_3$ | 1 | 5,6-(CH$_3$)$_2$ | 1 |
| 2.670 | 4-CH$_3$ | 1 | 5,6-(CH$_3$)$_2$ | 1 |
| 2.671 | 2-OCH$_3$ | 1 | 5,6-(CH$_3$)$_2$ | 1 |
| 2.672 | 3-OCH$_3$ | 1 | 5,6-(CH$_3$)$_2$ | 1 |
| 2.673 | 4-OCH$_3$ | 1 | 5,6-(CH$_3$)$_2$ | 1 |
| 2.674 | 2-CF$_3$ | 1 | 5,6-(CH$_3$)$_2$ | 1 |
| 2.675 | 3-CF$_3$ | 1 | 5,6-(CH$_3$)$_2$ | 1 |
| 2.676 | 4-CF$_3$ | 1 | 5,6-(CH$_3$)$_2$ | 1 |
| 2.677 | 2,3-Cl$_2$ | 2 | 5,6-(CH$_3$)$_2$ | 1 |
| 2.678 | 2,4-Cl$_2$ | 2 | 5,6-(CH$_3$)$_2$ | 1 |
| 2.679 | 2,5-Cl$_2$ | 2 | 5,6-(CH$_3$)$_2$ | 1 |
| 2.680 | 2,6-Cl$_2$ | 2 | 5,6-(CH$_3$)$_2$ | 1 |
| 2.681 | 3,4-Cl$_2$ | 2 | 5,6-(CH$_3$)$_2$ | 1 |
| 2.682 | 3,5-Cl$_2$ | 2 | 5,6-(CH$_3$)$_2$ | 1 |
| 2.683 | 2-CH$_3$, 4-Cl | 2 | 5,6-(CH$_3$)$_2$ | 1 |
| 2.684 | 2-Cl, 4-CH$_3$ | 2 | 5,6-(CH$_3$)$_2$ | 1 |
| 2.685 | 2-CF$_3$, 4-CH$_3$ | 2 | 5,6-(CH$_3$)$_2$ | 1 |
| 2.686 | 2-CH$_3$, 4-CF$_3$ | 2 | 5,6-(CH$_3$)$_2$ | 1 |
| 2.687 | — | — | 3,4-(CH$_3$)$_2$ | 1 |
| 2.688 | 2-F | 1 | 3,4-(CH$_3$)$_2$ | 1 |
| 2.689 | 3-F | 1 | 3,4-(CH$_3$)$_2$ | 1 |
| 2.690 | 4-F | 1 | 3,4-(CH$_3$)$_2$ | 1 |
| 2.691 | 2-Cl | 1 | 3,4-(CH$_3$)$_2$ | 1 |
| 2.692 | 3-Cl | 1 | 3,4-(CH$_3$)$_2$ | 1 |
| 2.693 | 4-Cl | 1 | 3,4-(CH$_3$)$_2$ | 1 |
| 2.694 | 2-CH$_3$ | 1 | 3,4-(CH$_3$)$_2$ | 1 |
| 2.695 | 3-CH$_3$ | 1 | 3,4-(CH$_3$)$_2$ | 1 |
| 2.696 | 4-CH$_3$ | 1 | 3,4-(CH$_3$)$_2$ | 1 |
| 2.697 | 2-OCH$_3$ | 1 | 3,4-(CH$_3$)$_2$ | 1 |
| 2.698 | 3-OCH$_3$ | 1 | 3,4-(CH$_3$)$_2$ | 1 |
| 2.699 | 4-OCH$_3$ | 1 | 3,4-(CH$_3$)$_2$ | 1 |
| 2.700 | 2-CF$_3$ | 1 | 3,4-(CH$_3$)$_2$ | 1 |
| 2.701 | 3-CF$_3$ | 1 | 3,4-(CH$_3$)$_2$ | 1 |
| 2.702 | 4-CF$_3$ | 1 | 3,4-(CH$_3$)$_2$ | 1 |
| 2.703 | 2,3-Cl$_2$ | 2 | 3,4-(CH$_3$)$_2$ | 1 |
| 2.704 | 2,4-Cl$_2$ | 2 | 3,4-(CH$_3$)$_2$ | 1 |
| 2.705 | 2,5-Cl$_2$ | 2 | 3,4-(CH$_3$)$_2$ | 1 |
| 2.706 | 2,6-Cl$_2$ | 2 | 3,4-(CH$_3$)$_2$ | 1 |
| 2.707 | 3,4-Cl$_2$ | 2 | 3,4-(CH$_3$)$_2$ | 1 |
| 2.708 | 3,5-Cl$_2$ | 2 | 3,4-(CH$_3$)$_2$ | 1 |
| 2.709 | 2-CH$_3$, 4-Cl | 2 | 3,4-(CH$_3$)$_2$ | 1 |
| 2.710 | 2-Cl, 4-CH$_3$ | 2 | 3,4-(CH$_3$)$_2$ | 1 |
| 2.711 | 2-CF$_3$, 4-CH$_3$ | 2 | 3,4-(CH$_3$)$_2$ | 1 |
| 2.712 | 2-CH$_3$, 4-CF$_3$ | 2 | 3,4-(CH$_3$)$_2$ | 1 |
| 2.713 | — | — | 4,6-(OCH$_3$)$_2$ | 1 |
| 2.714 | 2-F | 1 | 4,6-(OCH$_3$)$_2$ | 1 |
| 2.715 | 3-F | 1 | 4,6-(OCH$_3$)$_2$ | 1 |
| 2.716 | 4-F | 1 | 4,6-(OCH$_3$)$_2$ | 1 |
| 2.717 | 2-Cl | 1 | 4,6-(OCH$_3$)$_2$ | 1 |
| 2.718 | 3-Cl | 1 | 4,6-(OCH$_3$)$_2$ | 1 |
| 2.719 | 4-Cl | 1 | 4,6-(OCH$_3$)$_2$ | 1 |
| 2.720 | 2-CH$_3$ | 1 | 4,6-(OCH$_3$)$_2$ | 1 |
| 2.721 | 3-CH$_3$ | 1 | 4,6-(OCH$_3$)$_2$ | 1 |
| 2.722 | 4-CH$_3$ | 1 | 4,6-(OCH$_3$)$_2$ | 1 |
| 2.723 | 2-OCH$_3$ | 1 | 4,6-(OCH$_3$)$_2$ | 1 |
| 2.724 | 3-OCH$_3$ | 1 | 4,6-(OCH$_3$)$_2$ | 1 |
| 2.725 | 4-OCH$_3$ | 1 | 4,6-(OCH$_3$)$_2$ | 1 |
| 2.726 | 2-CF$_3$ | 1 | 4,6-(OCH$_3$)$_2$ | 1 |
| 2.727 | 3-CF$_3$ | 1 | 4,6-(OCH$_3$)$_2$ | 1 |
| 2.728 | 4-CF$_3$ | 1 | 4,6-(OCH$_3$)$_2$ | 1 |
| 2.729 | 2,3-Cl$_2$ | 2 | 4,6-(OCH$_3$)$_2$ | 1 |
| 2.730 | 2,4-Cl$_2$ | 2 | 4,6-(OCH$_3$)$_2$ | 1 |
| 2.731 | 2,5-Cl$_2$ | 2 | 4,6-(OCH$_3$)$_2$ | 1 |
| 2.732 | 2,6-Cl$_2$ | 2 | 4,6-(OCH$_3$)$_2$ | 1 |
| 2.733 | 3,4-Cl$_2$ | 2 | 4,6-(OCH$_3$)$_2$ | 1 |
| 2.734 | 3,5-Cl$_2$ | 2 | 4,6-(OCH$_3$)$_2$ | 1 |
| 2.735 | 2-CH$_3$, 4-Cl | 2 | 4,6-(OCH$_3$)$_2$ | 1 |
| 2.736 | 2-Cl, 4-CH$_3$ | 2 | 4,6-(OCH$_3$)$_2$ | 1 |
| 2.737 | 2-CF$_3$, 4-CH$_3$ | 2 | 4,6-(OCH$_3$)$_2$ | 1 |
| 2.738 | 2-CH$_3$, 4-CF$_3$ | 2 | 4,6-(OCH$_3$)$_2$ | 1 |

TABLE 3

Structure VI: Ar(X_m)–O–CH$_2$–Ar'(Y_n)–C(=O)–CH$_2$–SO–CH$_3$

| No. | x | m | Y | n |
|---|---|---|---|---|
| 3.001 | — | — | — | 0 |
| 3.002 | 2-F | 1 | — | 0 |
| 3.003 | 2-Cl | 1 | — | 0 |
| 3.004 | 3-Cl | 1 | — | 0 |
| 3.005 | 4-Cl | 1 | — | 0 |
| 3.006 | 2,4-Cl$_2$ | 2 | — | 0 |
| 3.007 | 2-CH$_3$, 4-Cl | 2 | — | 0 |
| 3.008 | 2-CH$_3$ | 1 | — | 0 |
| 3.009 | 4-CH$_3$ | 1 | — | 0 |
| 3.010 | 4-tert. C$_4$H$_9$ | 1 | — | 0 |
| 3.011 | — | — | 3-F | 1 |
| 3.012 | 2-F | 1 | 3-F | 1 |
| 3.013 | 3-F | 1 | 3-F | 1 |
| 3.014 | 4-F | 1 | 3-F | 1 |
| 3.015 | 2-Cl | 1 | 3-F | 1 |

TABLE 3-continued

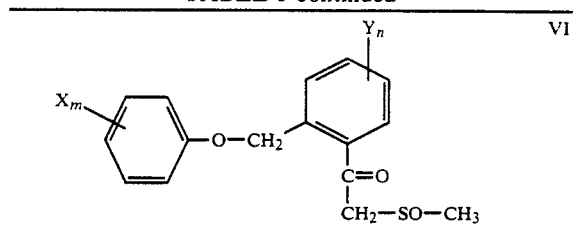

VI

| No. | x | m | Y | n |
|---|---|---|---|---|
| 3.016 | 3-Cl | 1 | 3-F | 1 |
| 3.017 | 4-Cl | 1 | 3-F | 1 |
| 3.018 | 2-CH$_3$ | 1 | 3-F | 1 |
| 3.019 | 3-CH$_3$ | 1 | 3-F | 1 |
| 3.020 | 4-CH$_3$ | 1 | 3-F | 1 |
| 3.021 | 2-OCH$_3$ | 1 | 3-F | 1 |
| 3.022 | 3-OCH$_3$ | 1 | 3-F | 1 |
| 3.023 | 4-OCH$_3$ | 1 | 3-F | 1 |
| 3.024 | 2-CF$_3$ | 1 | 3-F | 1 |
| 3.025 | 3-CF$_3$ | 1 | 3-F | 1 |
| 3.026 | 4-CF$_3$ | 1 | 3-F | 1 |
| 3.027 | 2,3-Cl$_2$ | 2 | 3-F | 1 |
| 3.028 | 2,4-Cl$_2$ | 2 | 3-F | 1 |
| 3.029 | 2,5-Cl$_2$ | 2 | 3-F | 1 |
| 3.030 | 2,6-Cl$_2$ | 2 | 3-F | 1 |
| 3.031 | 3,4-Cl$_2$ | 2 | 3-F | 1 |
| 3.032 | 3,5-Cl$_2$ | 2 | 3-F | 1 |
| 3.033 | 2-CH$_3$, 4-Cl | 2 | 3-F | 1 |
| 3.034 | 2-Cl, 4-CH$_3$ | 2 | 3-F | 1 |
| 3.035 | 2-CF$_3$, 4-CH$_3$ | 2 | 3-F | 1 |
| 3.036 | 2-CH$_3$, 4-CF$_3$ | 2 | 3-F | 1 |
| 3.037 | — | — | 3-Cl | 1 |
| 3.038 | 2-F | 1 | 3-Cl | 1 |
| 3.039 | 3-F | 1 | 3-Cl | 1 |
| 3.040 | 4-F | 1 | 3-Cl | 1 |
| 3.041 | 2-Cl | 1 | 3-Cl | 1 |
| 3.042 | 3-Cl | 1 | 3-Cl | 1 |
| 3.043 | 4-Cl | 1 | 3-Cl | 1 |
| 3.044 | 2-CH$_3$ | 1 | 3-Cl | 1 |
| 3.045 | 3-CH$_3$ | 1 | 3-Cl | 1 |
| 3.046 | 4-CH$_3$ | 1 | 3-Cl | 1 |
| 3.047 | 2-OCH$_3$ | 1 | 3-Cl | 1 |
| 3.048 | 3-OCH$_3$ | 1 | 3-Cl | 1 |
| 3.049 | 4-OCH$_3$ | 1 | 3-Cl | 1 |
| 3.050 | 2-CF$_3$ | 1 | 3-Cl | 1 |
| 3.051 | 3-CF$_3$ | 1 | 3-Cl | 1 |
| 3.052 | 4-CF$_3$ | 1 | 3-Cl | 1 |
| 3.053 | 2,3-Cl$_2$ | 2 | 3-Cl | 1 |
| 3.054 | 2,4-Cl$_2$ | 2 | 3-Cl | 1 |
| 3.055 | 2,5-Cl$_2$ | 2 | 3-Cl | 1 |
| 3.056 | 2,6-Cl$_2$ | 2 | 3-Cl | 1 |
| 3.057 | 3,4-Cl$_2$ | 2 | 3-Cl | 1 |
| 3.058 | 3,5-Cl$_2$ | 2 | 3-Cl | 1 |
| 3.059 | 2-CH$_3$, 4-Cl | 2 | 3-Cl | 1 |
| 3.060 | 2-Cl, 4-CH$_3$ | 2 | 3-Cl | 1 |
| 3.061 | 2-CF$_3$, 4-CH$_3$ | 2 | 3-Cl | 1 |
| 3.062 | 2-CH$_3$, 4-CF$_3$ | 2 | 3-Cl | 1 |
| 3.063 | — | — | 3-CH$_3$ | 1 |
| 3.064 | 2-F | 1 | 3-CH$_3$ | 1 |
| 3.065 | 3-F | 1 | 3-CH$_3$ | 1 |
| 3.066 | 4-F | 1 | 3-CH$_3$ | 1 |
| 3.067 | 2-Cl | 1 | 3-CH$_3$ | 1 |
| 3.068 | 3-Cl | 1 | 3-CH$_3$ | 1 |
| 3.069 | 4-Cl | 1 | 3-CH$_3$ | 1 |
| 3.070 | 2-CH$_3$ | 1 | 3-CH$_3$ | 1 |
| 3.071 | 3-CH$_3$ | 1 | 3-CH$_3$ | 1 |
| 3.072 | 4-CH$_3$ | 1 | 3-CH$_3$ | 1 |
| 3.073 | 2-OCH$_3$ | 1 | 3-CH$_3$ | 1 |
| 3.074 | 3-OCH$_3$ | 1 | 3-CH$_3$ | 1 |
| 3.075 | 4-OCH$_3$ | 1 | 3-CH$_3$ | 1 |
| 3.076 | 2-CF$_3$ | 1 | 3-CH$_3$ | 1 |
| 3.077 | 3-CF$_3$ | 1 | 3-CH$_3$ | 1 |
| 3.078 | 4-CF$_3$ | 1 | 3-CH$_3$ | 1 |
| 3.079 | 2,3-Cl$_2$ | 2 | 3-CH$_3$ | 1 |
| 3.080 | 2,4-Cl$_2$ | 2 | 3-CH$_3$ | 1 |
| 3.081 | 2,5-Cl$_2$ | 2 | 3-CH$_3$ | 1 |
| 3.082 | 2,6-Cl$_2$ | 2 | 3-CH$_3$ | 1 |
| 3.083 | 3,4-Cl$_2$ | 2 | 3-CH$_3$ | 1 |
| 3.084 | 3,5-Cl$_2$ | 2 | 3-CH$_3$ | 1 |
| 3.085 | 2-CH$_3$, 4-Cl | 2 | 3-CH$_3$ | 1 |
| 3.086 | 2-Cl, 4-CH$_3$ | 2 | 3-CH$_3$ | 1 |
| 3.087 | 2-CF$_3$, 4-CH$_3$ | 2 | 3-CH$_3$ | 1 |
| 3.088 | 2-CH$_3$, 4-CF$_3$ | 2 | 3-CH$_3$ | 1 |
| 3.089 | — | — | 3-OCH$_3$ | 1 |
| 3.090 | 2-F | 1 | 3-OCH$_3$ | 1 |
| 3.091 | 3-F | 1 | 3-OCH$_3$ | 1 |
| 3.092 | 4-F | 1 | 3-OCH$_3$ | 1 |
| 3.093 | 2-Cl | 1 | 3-OCH$_3$ | 1 |
| 3.094 | 3-Cl | 1 | 3-OCH$_3$ | 1 |
| 3.095 | 4-Cl | 1 | 3-OCH$_3$ | 1 |
| 3.096 | 2-CH$_3$ | 1 | 3-OCH$_3$ | 1 |
| 3.097 | 3-CH$_3$ | 1 | 3-OCH$_3$ | 1 |
| 3.098 | 4-CH$_3$ | 1 | 3-OCH$_3$ | 1 |
| 3.099 | 2-OCH$_3$ | 1 | 3-OCH$_3$ | 1 |
| 3.100 | 3-OCH$_3$ | 1 | 3-OCH$_3$ | 1 |
| 3.101 | 4-OCH$_3$ | 1 | 3-OCH$_3$ | 1 |
| 3.102 | 2-CF$_3$ | 1 | 3-OCH$_3$ | 1 |
| 3.103 | 3-CF$_3$ | 1 | 3-OCH$_3$ | 1 |
| 3.104 | 4-CF$_3$ | 1 | 3-OCH$_3$ | 1 |
| 3.105 | 2,3-Cl$_2$ | 2 | 3-OCH$_3$ | 1 |
| 3.106 | 2,4-Cl$_2$ | 2 | 3-OCH$_3$ | 1 |
| 3.107 | 2,5-Cl$_2$ | 2 | 3-OCH$_3$ | 1 |
| 3.108 | 2,6-Cl$_2$ | 2 | 3-OCH$_3$ | 1 |
| 3.109 | 3,4-Cl$_2$ | 2 | 3-OCH$_3$ | 1 |
| 3.110 | 3,5-Cl$_2$ | 2 | 3-OCH$_3$ | 1 |
| 3.111 | 2-CH$_3$, 4-Cl | 2 | 3-OCH$_3$ | 1 |
| 3.112 | 2-Cl, 4-CH$_3$ | 2 | 3-OCH$_3$ | 1 |
| 3.113 | 2-CF$_3$, 4-CH$_3$ | 2 | 3-OCH$_3$ | 1 |
| 3.114 | 2-CH$_3$, 4-CF$_3$ | 2 | 3-OCH$_3$ | 1 |
| 3.115 | — | — | 3-CF$_3$ | 1 |
| 3.116 | 2-F | 1 | 3-CF$_3$ | 1 |
| 3.117 | 3-F | 1 | 3-CF$_3$ | 1 |
| 3.118 | 4-F | 1 | 3-CF$_3$ | 1 |
| 3.119 | 2-Cl | 1 | 3-CF$_3$ | 1 |
| 3.120 | 3-Cl | 1 | 3-CF$_3$ | 1 |
| 3.121 | 4-Cl | 1 | 3-CF$_3$ | 1 |
| 3.122 | 2-CH$_3$ | 1 | 3-CF$_3$ | 1 |
| 3.123 | 3-CH$_3$ | 1 | 3-CF$_3$ | 1 |
| 3.124 | 4-CH$_3$ | 1 | 3-CF$_3$ | 1 |
| 3.125 | 2-OCH$_3$ | 1 | 3-CF$_3$ | 1 |
| 3.126 | 3-OCH$_3$ | 1 | 3-CF$_3$ | 1 |
| 3.127 | 4-OCH$_3$ | 1 | 3-CF$_3$ | 1 |
| 3.128 | 2-CF$_3$ | 1 | 3-CF$_3$ | 1 |
| 3.129 | 3-CF$_3$ | 1 | 3-CF$_3$ | 1 |
| 3.130 | 4-CF$_3$ | 1 | 3-CF$_3$ | 1 |
| 3.131 | 2,3-Cl$_2$ | 2 | 3-CF$_3$ | 1 |
| 3.132 | 2,4-Cl$_2$ | 2 | 3-CF$_3$ | 1 |
| 3.133 | 2,5-Cl$_2$ | 2 | 3-CF$_3$ | 1 |
| 3.134 | 2,6-Cl$_2$ | 2 | 3-CF$_3$ | 1 |
| 3.135 | 3,4-Cl$_2$ | 2 | 3-CF$_3$ | 1 |
| 3.136 | 3,5-Cl$_2$ | 2 | 3-CF$_3$ | 1 |
| 3.137 | 2-CH$_3$, 4-Cl | 2 | 3-CF$_3$ | 1 |
| 3.138 | 2-Cl, 4-CH$_3$ | 2 | 3-CF$_3$ | 1 |
| 3.139 | 2-CF$_3$, 4-CH$_3$ | 2 | 3-CF$_3$ | 1 |
| 3.140 | 2-CH$_3$, 4-CF$_3$ | 2 | 3-CF$_3$ | 1 |
| 3.141 | — | — | 4-F | 1 |
| 3.142 | 2-F | 1 | 4-F | 1 |
| 3.143 | 3-F | 1 | 4-F | 1 |
| 3.144 | 4-F | 1 | 4-F | 1 |
| 3.145 | 2-Cl | 1 | 4-F | 1 |
| 3.146 | 3-Cl | 1 | 4-F | 1 |
| 3.147 | 4-Cl | 1 | 4-F | 1 |
| 3.148 | 2-CH$_3$ | 1 | 4-F | 1 |
| 3.149 | 3-CH$_3$ | 1 | 4-F | 1 |
| 3.150 | 4-CH$_3$ | 1 | 4-F | 1 |
| 3.151 | 2-OCH$_3$ | 1 | 4-F | 1 |
| 3.152 | 3-OCH$_3$ | 1 | 4-F | 1 |
| 3.153 | 4-OCH$_3$ | 1 | 4-F | 1 |
| 3.154 | 2-CF$_3$ | 1 | 4-F | 1 |
| 3.155 | 3-CF$_3$ | 1 | 4-F | 1 |

TABLE 3-continued

Structure VI: X_m-phenyl-O-CH2-phenyl(Y_n)-C(=O)-CH2-SO-CH3

| No. | x | m | Y | n |
|---|---|---|---|---|
| 3.156 | 4-CF₃ | 1 | 4-F | 1 |
| 3.157 | 2,3-Cl₂ | 2 | 4-F | 1 |
| 3.158 | 2,4-Cl₂ | 2 | 4-F | 1 |
| 3.159 | 2,5-Cl₂ | 2 | 4-F | 1 |
| 3.160 | 2,6-Cl₂ | 2 | 4-F | 1 |
| 3.161 | 3,4-Cl₂ | 2 | 4-F | 1 |
| 3.162 | 3,5-Cl₂ | 2 | 4-F | 1 |
| 3.163 | 2-CH₃, 4-Cl | 2 | 4-F | 1 |
| 3.164 | 2-Cl, 4-CH₃ | 2 | 4-F | 1 |
| 3.165 | 2-CF₃, 4-CH₃ | 2 | 4-F | 1 |
| 3.166 | 2-CH₃, 4-CF₃ | 2 | 4-F | 1 |
| 3.167 | — | — | 4-Cl | 1 |
| 3.168 | 2-F | 1 | 4-Cl | 1 |
| 3.169 | 3-F | 1 | 4-Cl | 1 |
| 3.170 | 4-F | 1 | 4-Cl | 1 |
| 3.171 | 2-Cl | 1 | 4-Cl | 1 |
| 3.172 | 3-Cl | 1 | 4-Cl | 1 |
| 3.173 | 4-Cl | 1 | 4-Cl | 1 |
| 3.174 | 2-CH₃ | 1 | 4-Cl | 1 |
| 3.175 | 3-CH₃ | 1 | 4-Cl | 1 |
| 3.176 | 4-CH₃ | 1 | 4-Cl | 1 |
| 3.177 | 2-OCH₃ | 1 | 4-Cl | 1 |
| 3.178 | 3-OCH₃ | 1 | 4-Cl | 1 |
| 3.179 | 4-OCH₃ | 1 | 4-Cl | 1 |
| 3.180 | 2-CF₃ | 1 | 4-Cl | 1 |
| 3.181 | 3-CF₃ | 1 | 4-Cl | 1 |
| 3.182 | 4-CF₃ | 1 | 4-Cl | 1 |
| 3.183 | 2,3-Cl₂ | 2 | 4-Cl | 1 |
| 3.184 | 2,4-Cl₂ | 2 | 4-Cl | 1 |
| 3.185 | 2,5-Cl₂ | 2 | 4-Cl | 1 |
| 3.186 | 2,6-Cl₂ | 2 | 4-Cl | 1 |
| 3.187 | 3,4-Cl₂ | 2 | 4-Cl | 1 |
| 3.188 | 3,5-Cl₂ | 2 | 4-Cl | 1 |
| 3.189 | 2-CH₃, 4-Cl | 2 | 4-Cl | 1 |
| 3.190 | 2-Cl, 4-CH₃ | 2 | 4-Cl | 1 |
| 3.191 | 2-CF₃, 4-CH₃ | 2 | 4-Cl | 1 |
| 3.192 | 2-CH₃, 4-CF₃ | 2 | 4-Cl | 1 |
| 3.193 | — | — | 4-Me | 1 |
| 3.194 | 2-F | 1 | 4-Me | 1 |
| 3.195 | 3-F | 1 | 4-Me | 1 |
| 3.196 | 4-F | 1 | 4-Me | 1 |
| 3.197 | 2-Cl | 1 | 4-Me | 1 |
| 3.198 | 3-Cl | 1 | 4-Me | 1 |
| 3.199 | 4-Cl | 1 | 4-Me | 1 |
| 3.200 | 2-CH₃ | 1 | 4-Me | 1 |
| 3.201 | 3-CH₃ | 1 | 4-Me | 1 |
| 3.202 | 4-CH₃ | 1 | 4-Me | 1 |
| 3.203 | 2-OCH₃ | 1 | 4-Me | 1 |
| 3.204 | 3-OCH₃ | 1 | 4-Me | 1 |
| 3.205 | 4-OCH₃ | 1 | 4-Me | 1 |
| 3.206 | 2-CF₃ | 1 | 4-Me | 1 |
| 3.207 | 3-CF₃ | 1 | 4-Me | 1 |
| 3.208 | 4-CF₃ | 1 | 4-Me | 1 |
| 3.209 | 2,3-Cl₂ | 2 | 4-Me | 1 |
| 3.210 | 2,4-Cl₂ | 2 | 4-Me | 1 |
| 3.211 | 2,5-Cl₂ | 2 | 4-Me | 1 |
| 3.212 | 2,6-Cl₂ | 2 | 4-Me | 1 |
| 3.213 | 3,4-Cl₂ | 2 | 4-Me | 1 |
| 3.214 | 3,5-Cl₂ | 2 | 4-Me | 1 |
| 3.215 | 2-CH₃, 4-Cl | 2 | 4-Me | 1 |
| 3.216 | 2-Cl, 4-CH₃ | 2 | 4-Me | 1 |
| 3.217 | 2-CF₃, 4-CH₃ | 2 | 4-Me | 1 |
| 3.218 | 2-CH₃, 4-CF₃ | 2 | 4-Me | 1 |
| 3.219 | — | — | 4-OCH₃ | 1 |
| 3.220 | 2-F | 1 | 4-OCH₃ | 1 |
| 3.221 | 3-F | 1 | 4-OCH₃ | 1 |
| 3.222 | 4-F | 1 | 4-OCH₃ | 1 |
| 3.223 | 2-Cl | 1 | 4-OCH₃ | 1 |
| 3.224 | 3-Cl | 1 | 4-OCH₃ | 1 |
| 3.225 | 4-Cl | 1 | 4-OCH₃ | 1 |
| 3.226 | 2-CH₃ | 1 | 4-OCH₃ | 1 |
| 3.227 | 3-CH₃ | 1 | 4-OCH₃ | 1 |
| 3.228 | 4-CH₃ | 1 | 4-OCH₃ | 1 |
| 3.229 | 2-OCH₃ | 1 | 4-OCH₃ | 1 |
| 3.230 | 3-OCH₃ | 1 | 4-OCH₃ | 1 |
| 3.231 | 4-OCH₃ | 1 | 4-OCH₃ | 1 |
| 3.232 | 2-CF₃ | 1 | 4-OCH₃ | 1 |
| 3.233 | 3-CF₃ | 1 | 4-OCH₃ | 1 |
| 3.234 | 4-CF₃ | 1 | 4-OCH₃ | 1 |
| 3.235 | 2,3-Cl₂ | 2 | 4-OCH₃ | 1 |
| 3.236 | 2,4-Cl₂ | 2 | 4-OCH₃ | 1 |
| 3.237 | 2,5-Cl₂ | 2 | 4-OCH₃ | 1 |
| 3.238 | 2,6-Cl₂ | 2 | 4-OCH₃ | 1 |
| 3.239 | 3,4-Cl₂ | 2 | 4-OCH₃ | 1 |
| 3.240 | 3,5-Cl₂ | 2 | 4-OCH₃ | 1 |
| 3.241 | 2-CH₃, 4-Cl | 2 | 4-OCH₃ | 1 |
| 3.242 | 2-Cl, 4-CH₃ | 2 | 4-OCH₃ | 1 |
| 3.243 | 2-CF₃, 4-CH₃ | 2 | 4-OCH₃ | 1 |
| 3.244 | 2-CH₃, 4-CF₃ | 2 | 4-OCH₃ | 1 |
| 3.245 | — | — | 4-CF₃ | 1 |
| 3.246 | 2-F | 1 | 4-CF₃ | 1 |
| 3.247 | 3-F | 1 | 4-CF₃ | 1 |
| 3.248 | 4-F | 1 | 4-CF₃ | 1 |
| 3.249 | 2-Cl | 1 | 4-CF₃ | 1 |
| 3.250 | 3-Cl | 1 | 4-CF₃ | 1 |
| 3.251 | 4-Cl | 1 | 4-CF₃ | 1 |
| 3.252 | 2-CH₃ | 1 | 4-CF₃ | 1 |
| 3.253 | 3-CH₃ | 1 | 4-CF₃ | 1 |
| 3.254 | 4-CH₃ | 1 | 4-CF₃ | 1 |
| 3.255 | 2-OCH₃ | 1 | 4-CF₃ | 1 |
| 3.256 | 3-OCH₃ | 1 | 4-CF₃ | 1 |
| 3.257 | 4-OCH₃ | 1 | 4-CF₃ | 1 |
| 3.258 | 2-CF₃ | 1 | 4-CF₃ | 1 |
| 3.259 | 3-CF₃ | 1 | 4-CF₃ | 1 |
| 3.260 | 4-CF₃ | 1 | 4-CF₃ | 1 |
| 3.261 | 2,3-Cl₂ | 2 | 4-CF₃ | 1 |
| 3.262 | 2,4-Cl₂ | 2 | 4-CF₃ | 1 |
| 3.263 | 2,5-Cl₂ | 2 | 4-CF₃ | 1 |
| 3.264 | 2,6-Cl₂ | 2 | 4-CF₃ | 1 |
| 3.265 | 3,4-Cl₂ | 2 | 4-CF₃ | 1 |
| 3.266 | 3,5-Cl₂ | 2 | 4-CF₃ | 1 |
| 3.267 | 2-CH₃, 4-Cl | 2 | 4-CF₃ | 1 |
| 3.268 | 2-Cl, 4-CH₃ | 2 | 4-CF₃ | 1 |
| 3.269 | 2-CF₃, 4-CH₃ | 2 | 4-CF₃ | 1 |
| 3.270 | 2-CH₃, 4-CF₃ | 2 | 4-CF₃ | 1 |
| 3.271 | — | — | 5-F | 1 |
| 3.272 | 2-F | 1 | 5-F | 1 |
| 3.273 | 3-F | 1 | 5-F | 1 |
| 3.274 | 4-F | 1 | 5-F | 1 |
| 3.275 | 2-Cl | 1 | 5-F | 1 |
| 3.276 | 3-Cl | 1 | 5-F | 1 |
| 3.277 | 4-Cl | 1 | 5-F | 1 |
| 3.278 | 2-CH₃ | 1 | 5-F | 1 |
| 3.279 | 3-CH₃ | 1 | 5-F | 1 |
| 3.280 | 4-CH₃ | 1 | 5-F | 1 |
| 3.281 | 2-OCH₃ | 1 | 5-F | 1 |
| 3.282 | 3-OCH₃ | 1 | 5-F | 1 |
| 3.283 | 4-OCH₃ | 1 | 5-F | 1 |
| 3.284 | 2-CF₃ | 1 | 5-F | 1 |
| 3.285 | 3-CF₃ | 1 | 5-F | 1 |
| 3.286 | 4-CF₃ | 1 | 5-F | 1 |
| 3.287 | 2,3-Cl₂ | 2 | 5-F | 1 |
| 3.288 | 2,4-Cl₂ | 2 | 5-F | 1 |
| 3.289 | 2,5-Cl₂ | 2 | 5-F | 1 |
| 3.290 | 2,6-Cl₂ | 2 | 5-F | 1 |
| 3.291 | 3,4-Cl₂ | 2 | 5-F | 1 |
| 3.292 | 3,5-Cl₂ | 2 | 5-F | 1 |
| 3.293 | 2-CH₃, 4-Cl | 2 | 5-F | 1 |
| 3.294 | 2-Cl, 4-CH₃ | 2 | 5-F | 1 |
| 3.295 | 2-CF₃, 4-CH₃ | 2 | 5-F | 1 |

TABLE 3-continued

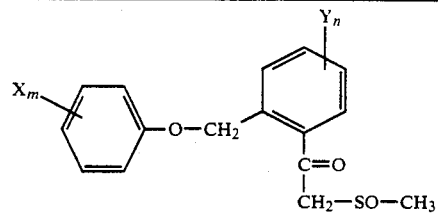

VI

| No. | x | m | Y | n |
|---|---|---|---|---|
| 3.296 | 2-CH$_3$, 4-CF$_3$ | 2 | 5-F | 1 |
| 3.297 | — | — | 5-Cl | 1 |
| 3.298 | 2-F | 1 | 5-Cl | 1 |
| 3.299 | 3-F | 1 | 5-Cl | 1 |
| 3.300 | 4-F | 1 | 5-Cl | 1 |
| 3.301 | 2-Cl | 1 | 5-Cl | 1 |
| 3.302 | 3-Cl | 1 | 5-Cl | 1 |
| 3.303 | 4-Cl | 1 | 5-Cl | 1 |
| 3.304 | 2-CH$_3$ | 1 | 5-Cl | 1 |
| 3.305 | 3-CH$_3$ | 1 | 5-Cl | 1 |
| 3.306 | 4-CH$_3$ | 1 | 5-Cl | 1 |
| 3.307 | 2-OCH$_3$ | 1 | 5-Cl | 1 |
| 3.308 | 3-OCH$_3$ | 1 | 5-Cl | 1 |
| 3.309 | 4-OCH$_3$ | 1 | 5-Cl | 1 |
| 3.310 | 2-CF$_3$ | 1 | 5-Cl | 1 |
| 3.311 | 3-CF$_3$ | 1 | 5-Cl | 1 |
| 3.312 | 4-CF$_3$ | 1 | 5-Cl | 1 |
| 3.313 | 2,3-Cl$_2$ | 2 | 5-Cl | 1 |
| 3.314 | 2,4-Cl$_2$ | 2 | 5-Cl | 1 |
| 3.315 | 2,5-Cl$_2$ | 2 | 5-Cl | 1 |
| 3.316 | 2,6-Cl$_2$ | 2 | 5-Cl | 1 |
| 3.317 | 3,4-Cl$_2$ | 2 | 5-Cl | 1 |
| 3.318 | 3,5-Cl$_2$ | 2 | 5-Cl | 1 |
| 3.319 | 2-CH$_3$, 4-Cl | 2 | 5-Cl | 1 |
| 3.320 | 2-Cl, 4-CH$_3$ | 2 | 5-Cl | 1 |
| 3.321 | 2-CF$_3$, 4-CH$_3$ | 2 | 5-Cl | 1 |
| 3.322 | 2-CH$_3$, 4-CF$_3$ | 2 | 5-Cl | 1 |
| 3.323 | — | — | 5-Me | 1 |
| 3.324 | 2-F | 1 | 5-Me | 1 |
| 3.325 | 3-F | 1 | 5-Me | 1 |
| 3.326 | 4-F | 1 | 5-Me | 1 |
| 3.327 | 2-Cl | 1 | 5-Me | 1 |
| 3.328 | 3-Cl | 1 | 5-Me | 1 |
| 3.329 | 4-Cl | 1 | 5-Me | 1 |
| 3.330 | 2-CH$_3$ | 1 | 5-Me | 1 |
| 3.331 | 3-CH$_3$ | 1 | 5-Me | 1 |
| 3.332 | 4-CH$_3$ | 1 | 5-Me | 1 |
| 3.333 | 2-OCH$_3$ | 1 | 5-Me | 1 |
| 3.334 | 3-OCH$_3$ | 1 | 5-Me | 1 |
| 3.335 | 4-OCH$_3$ | 1 | 5-Me | 1 |
| 3.336 | 2-CF$_3$ | 1 | 5-Me | 1 |
| 3.337 | 3-CF$_3$ | 1 | 5-Me | 1 |
| 3.338 | 4-CF$_3$ | 1 | 5-Me | 1 |
| 3.339 | 2,3-Cl$_2$ | 2 | 5-Me | 1 |
| 3.340 | 2,4-Cl$_2$ | 2 | 5-Me | 1 |
| 3.341 | 2,5-Cl$_2$ | 2 | 5-Me | 1 |
| 3.342 | 2,6-Cl$_2$ | 2 | 5-Me | 1 |
| 3.343 | 3,4-Cl$_2$ | 2 | 5-Me | 1 |
| 3.344 | 3,5-Cl$_2$ | 2 | 5-Me | 1 |
| 3.345 | 2-CH$_3$, 4-Cl | 2 | 5-Me | 1 |
| 3.346 | 2-Cl, 4-CH$_3$ | 2 | 5-Me | 1 |
| 3.347 | 2-CF$_3$, 4-CH$_3$ | 2 | 5-Me | 1 |
| 3.348 | 2-CH$_3$, 4-CF$_3$ | 2 | 5-Me | 1 |
| 3.349 | — | — | 5-OCH$_3$ | 1 |
| 3.350 | 2-F | 1 | 5-OCH$_3$ | 1 |
| 3.351 | 3-F | 1 | 5-OCH$_3$ | 1 |
| 3.352 | 4-F | 1 | 5-OCH$_3$ | 1 |
| 3.353 | 2-Cl | 1 | 5-OCH$_3$ | 1 |
| 3.354 | 3-Cl | 1 | 5-OCH$_3$ | 1 |
| 3.355 | 4-Cl | 1 | 5-OCH$_3$ | 1 |
| 3.356 | 2-CH$_3$ | 1 | 5-OCH$_3$ | 1 |
| 3.357 | 3-CH$_3$ | 1 | 5-OCH$_3$ | 1 |
| 3.358 | 4-CH$_3$ | 1 | 5-OCH$_3$ | 1 |
| 3.359 | 2-OCH$_3$ | 1 | 5-OCH$_3$ | 1 |
| 3.360 | 3-OCH$_3$ | 1 | 5-OCH$_3$ | 1 |
| 3.361 | 4-OCH$_3$ | 1 | 5-OCH$_3$ | 1 |
| 3.362 | 2-CF$_3$ | 1 | 5-OCH$_3$ | 1 |
| 3.363 | 3-CF$_3$ | 1 | 5-OCH$_3$ | 1 |
| 3.364 | 4-CF$_3$ | 1 | 5-OCH$_3$ | 1 |
| 3.365 | 2,3-Cl$_2$ | 2 | 5-OCH$_3$ | 1 |

TABLE 3-continued

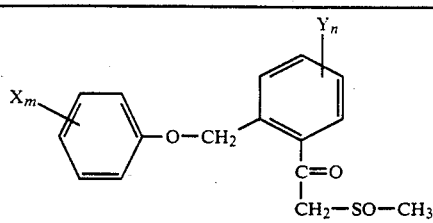

VI

| No. | x | m | Y | n |
|---|---|---|---|---|
| 3.366 | 2,4-Cl$_2$ | 2 | 5-OCH$_3$ | 1 |
| 3.367 | 2,5-Cl$_2$ | 2 | 5-OCH$_3$ | 1 |
| 3.368 | 2,6-Cl$_2$ | 2 | 5-OCH$_3$ | 1 |
| 3.369 | 3,4-Cl$_2$ | 2 | 5-OCH$_3$ | 1 |
| 3.370 | 3,5-Cl$_2$ | 2 | 5-OCH$_3$ | 1 |
| 3.371 | 2-CH$_3$, 4-Cl | 2 | 5-OCH$_3$ | 1 |
| 3.372 | 2-Cl, 4-CH$_3$ | 2 | 5-OCH$_3$ | 1 |
| 3.373 | 2-CF$_3$, 4-CH$_3$ | 2 | 5-OCH$_3$ | 1 |
| 3.374 | 2-CH$_3$, 4-CF$_3$ | 2 | 5-OCH$_3$ | 1 |
| 3.375 | — | — | 5-CF$_3$ | 1 |
| 3.338 | 4-CF$_3$ | 1 | 5-Me | 1 |
| 3.339 | 2,3-Cl$_2$ | 2 | 5-Me | 1 |
| 3.340 | 2,4-Cl$_2$ | 2 | 5-Me | 1 |
| 3.341 | 2,5-Cl$_2$ | 2 | 5-Me | 1 |
| 3.342 | 2,6-Cl$_2$ | 2 | 5-Me | 1 |
| 3.343 | 3,4-Cl$_2$ | 2 | 5-Me | 1 |
| 3.344 | 3,5-Cl$_2$ | 2 | 5-Me | 1 |
| 3.345 | 2-CH$_3$, 4-Cl | 2 | 5-Me | 1 |
| 3.346 | 2-Cl, 4-CH$_3$ | 2 | 5-Me | 1 |
| 3.347 | 2-CF$_3$, 4-CH$_3$ | 2 | 5-Me | 1 |
| 3.348 | 2-CH$_3$, 4-CF$_3$ | 2 | 5-Me | 1 |
| 3.349 | — | — | 5-OCH$_3$ | 1 |
| 3.350 | 2-F | 1 | 5-OCH$_3$ | 1 |
| 3.351 | 3-F | 1 | 5-OCH$_3$ | 1 |
| 3.352 | 4-F | 1 | 5-OCH$_3$ | 1 |
| 3.353 | 2-Cl | 1 | 5-OCH$_3$ | 1 |
| 3.354 | 3-Cl | 1 | 5-OCH$_3$ | 1 |
| 3.355 | 4-Cl | 1 | 5-OCH$_3$ | 1 |
| 3.356 | 2-CH$_3$ | 1 | 5-OCH$_3$ | 1 |
| 3.357 | 3-CH$_3$ | 1 | 5-OCH$_3$ | 1 |
| 3.358 | 4-CH$_3$ | 1 | 5-OCH$_3$ | 1 |
| 3.359 | 2-OCH$_3$ | 1 | 5-OCH$_3$ | 1 |
| 3.360 | 3-OCH$_3$ | 1 | 5-OCH$_3$ | 1 |
| 3.361 | 4-OCH$_3$ | 1 | 5-OCH$_3$ | 1 |
| 3.362 | 2-CF$_3$ | 1 | 5-OCH$_3$ | 1 |
| 3.363 | 3-CF$_3$ | 1 | 5-OCH$_3$ | 1 |
| 3.364 | 4-CF$_3$ | 1 | 5-OCH$_3$ | 1 |
| 3.365 | 2,3-Cl$_2$ | 2 | 5-OCH$_3$ | 1 |
| 3.366 | 2,4-Cl$_2$ | 2 | 5-OCH$_3$ | 1 |
| 3.367 | 2,5-Cl$_2$ | 2 | 5-OCH$_3$ | 1 |
| 3.368 | 2,6-Cl$_2$ | 2 | 5-OCH$_3$ | 1 |
| 3.369 | 3,4-Cl$_2$ | 2 | 5-OCH$_3$ | 1 |
| 3.370 | 3,5-Cl$_2$ | 2 | 5-OCH$_3$ | 1 |
| 3.371 | 2-CH$_3$, 4-Cl | 2 | 5-OCH$_3$ | 1 |
| 3.372 | 2-Cl, 4-CH$_3$ | 2 | 5-OCH$_3$ | 1 |
| 3.373 | 2-CF$_3$, 4-CH$_3$ | 2 | 5-OCH$_3$ | 1 |
| 3.374 | 2-CH$_3$, 4-CF$_3$ | 2 | 5-OCH$_3$ | 1 |
| 3.375 | — | — | 5-CF$_3$ | 1 |
| 3.376 | 2-F | 1 | 5-CF$_3$ | 1 |
| 3.377 | 3-F | 1 | 5-CF$_3$ | 1 |
| 3.378 | 4-F | 1 | 5-CF$_3$ | 1 |
| 3.379 | 2-Cl | 1 | 5-CF$_3$ | 1 |
| 3.380 | 3-Cl | 1 | 5-CF$_3$ | 1 |
| 3.381 | 4-Cl | 1 | 5-CF$_3$ | 1 |
| 3.382 | 2-CH$_3$ | 1 | 5-CF$_3$ | 1 |
| 3.383 | 3-CH$_3$ | 1 | 5-CF$_3$ | 1 |
| 3.384 | 4-CH$_3$ | 1 | 5-CF$_3$ | 1 |
| 3.385 | 2-OCH$_3$ | 1 | 5-CF$_3$ | 1 |
| 3.386 | 3-OCH$_3$ | 1 | 5-CF$_3$ | 1 |
| 3.387 | 4-OCH$_3$ | 1 | 5-CF$_3$ | 1 |
| 3.388 | 2-CF$_3$ | 1 | 5-CF$_3$ | 1 |
| 3.389 | 3-CF$_3$ | 1 | 5-CF$_3$ | 1 |
| 3.390 | 4-CF$_3$ | 1 | 5-CF$_3$ | 1 |
| 3.391 | 2,3-Cl$_2$ | 2 | 5-CF$_3$ | 1 |
| 3.392 | 2,4-Cl$_2$ | 2 | 5-CF$_3$ | 1 |
| 3.393 | 2,5-Cl$_2$ | 2 | 5-CF$_3$ | 1 |
| 3.394 | 2,6-Cl$_2$ | 2 | 5-CF$_3$ | 1 |
| 3.395 | 3,4-Cl$_2$ | 2 | 5-CF$_3$ | 1 |
| 3.396 | 3,5-Cl$_2$ | 2 | 5-CF$_3$ | 1 |
| 3.397 | 2-CH$_3$, 4-Cl | 2 | 5-CF$_3$ | 1 |

TABLE 3-continued

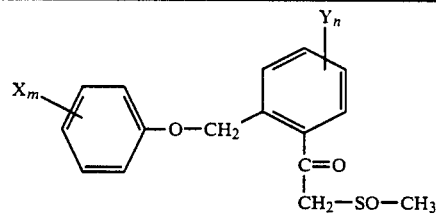

VI

| No. | x | m | Y | n |
|---|---|---|---|---|
| 3.398 | 2-Cl, 4-CH$_3$ | 2 | 5-CF$_3$ | 1 |
| 3.399 | 2-CF$_3$, 4-CH$_3$ | 2 | 5-CF$_3$ | 1 |
| 3.400 | 2-CH$_3$, 4-CF$_3$ | 2 | 5-CF$_3$ | 1 |
| 3.401 | — | — | 6-F | 1 |
| 3.402 | 2-F | 1 | 6-F | 1 |
| 3.403 | 3-F | 1 | 6-F | 1 |
| 3.404 | 4-F | 1 | 6-F | 1 |
| 3.405 | 2-Cl | 1 | 6-F | 1 |
| 3.406 | 3-Cl | 1 | 6-F | 1 |
| 3.407 | 4-Cl | 1 | 6-F | 1 |
| 3.408 | 2-CH$_3$ | 1 | 6-F | 1 |
| 3.409 | 3-CH$_3$ | 1 | 6-F | 1 |
| 3.410 | 4-CH$_3$ | 1 | 6-F | 1 |
| 3.411 | 2-OCH$_3$ | 1 | 6-F | 1 |
| 3.412 | 3-OCH$_3$ | 1 | 6-F | 1 |
| 3.413 | 4-OCH$_3$ | 1 | 6-F | 1 |
| 3.414 | 2-CF$_3$ | 1 | 6-F | 1 |
| 3.415 | 3-CF$_3$ | 1 | 6-F | 1 |
| 3.416 | 4-CF$_3$ | 1 | 6-F | 1 |
| 3.417 | 2,3-Cl$_2$ | 2 | 6-F | 1 |
| 3.418 | 2,4-Cl$_2$ | 2 | 6-F | 1 |
| 3.419 | 2,5-Cl$_2$ | 2 | 6-F | 1 |
| 3.420 | 2,6-Cl$_2$ | 2 | 6-F | 1 |
| 3.421 | 3,4-Cl$_2$ | 2 | 6-F | 1 |
| 3.422 | 3,5-Cl$_2$ | 2 | 6-F | 1 |
| 3.423 | 2-CH$_3$, 4-Cl | 2 | 6-F | 1 |
| 3.424 | 2-Cl, 4-CH$_3$ | 2 | 6-F | 1 |
| 3.425 | 2-CF$_3$, 4-CH$_3$ | 2 | 6-F | 1 |
| 3.426 | 2-CH$_3$, 4-CF$_3$ | 2 | 6-F | 1 |
| 3.427 | — | — | 6-Cl | 1 |
| 3.428 | 2-F | 1 | 6-Cl | 1 |
| 3.429 | 3-F | 1 | 6-Cl | 1 |
| 3.430 | 4-F | 1 | 6-Cl | 1 |
| 3.431 | 2-Cl | 1 | 6-Cl | 1 |
| 3.432 | 3-Cl | 1 | 6-Cl | 1 |
| 3.433 | 4-Cl | 1 | 6-Cl | 1 |
| 3.434 | 2-CH$_3$ | 1 | 6-Cl | 1 |
| 3.435 | 3-CH$_3$ | 1 | 6-Cl | 1 |
| 3.436 | 4-CH$_3$ | 1 | 6-Cl | 1 |
| 3.437 | 2-OCH$_3$ | 1 | 6-Cl | 1 |
| 3.438 | 3-OCH$_3$ | 1 | 6-Cl | 1 |
| 3.439 | 4-OCH$_3$ | 1 | 6-Cl | 1 |
| 3.440 | 2-CF$_3$ | 1 | 6-Cl | 1 |
| 3.441 | 3-CF$_3$ | 1 | 6-Cl | 1 |
| 3.442 | 4-CF$_3$ | 1 | 6-Cl | 1 |
| 3.443 | 2,3-Cl$_2$ | 2 | 6-Cl | 1 |
| 3.444 | 2,4-Cl$_2$ | 2 | 6-Cl | 1 |
| 3.445 | 2,5-Cl$_2$ | 2 | 6-Cl | 1 |
| 3.446 | 2,6-Cl$_2$ | 2 | 6-Cl | 1 |
| 3.447 | 3,4-Cl$_2$ | 2 | 6-Cl | 1 |
| 3.448 | 3,5-Cl$_2$ | 2 | 6-Cl | 1 |
| 3.449 | 2-CH$_3$, 4-Cl | 2 | 6-Cl | 1 |
| 3.450 | 2-Cl, 4-CH$_3$ | 2 | 6-Cl | 1 |
| 3.451 | 2-CF$_3$, 4-CH$_3$ | 2 | 6-Cl | 1 |
| 3.452 | 2-CH$_3$, 4-CF$_3$ | 2 | 6-Cl | 1 |
| 3.453 | — | — | 6-CH$_3$ | 1 |
| 3.454 | 2-F | 1 | 6-CH$_3$ | 1 |
| 3.455 | 3-F | 1 | 6-CH$_3$ | 1 |
| 3.456 | 4-F | 1 | 6-CH$_3$ | 1 |
| 3.457 | 2-Cl | 1 | 6-CH$_3$ | 1 |
| 3.458 | 3-Cl | 1 | 6-CH$_3$ | 1 |
| 3.459 | 4-Cl | 1 | 6-CH$_3$ | 1 |
| 3.460 | 2-CH$_3$ | 1 | 6-CH$_3$ | 1 |
| 3.461 | 3-CH$_3$ | 1 | 6-CH$_3$ | 1 |
| 3.462 | 4-CH$_3$ | 1 | 6-CH$_3$ | 1 |
| 3.463 | 2-OCH$_3$ | 1 | 6-CH$_3$ | 1 |
| 3.464 | 3-OCH$_3$ | 1 | 6-CH$_3$ | 1 |
| 3.465 | 4-OCH$_3$ | 1 | 6-CH$_3$ | 1 |
| 3.466 | 2-CF$_3$ | 1 | 6-CH$_3$ | 1 |
| 3.467 | 3-CF$_3$ | 1 | 6-CH$_3$ | 1 |
| 3.468 | 4-CF$_3$ | 1 | 6-CH$_3$ | 1 |
| 3.469 | 2,3-Cl$_2$ | 2 | 6-CH$_3$ | 1 |
| 3.470 | 2,4-Cl$_2$ | 2 | 6-CH$_3$ | 1 |
| 3.471 | 2,5-Cl$_2$ | 2 | 6-CH$_3$ | 1 |
| 3.472 | 2,6-Cl$_2$ | 2 | 6-CH$_3$ | 1 |
| 3.473 | 3,4-Cl$_2$ | 2 | 6-CH$_3$ | 1 |
| 3.474 | 3,5-Cl$_2$ | 2 | 6-CH$_3$ | 1 |
| 3.475 | 2-CH$_3$, 4-Cl | 2 | 6-CH$_3$ | 1 |
| 3.476 | 2-Cl, 4-CH$_3$ | 2 | 6-CH$_3$ | 1 |
| 3.477 | 2-CF$_3$, 4-CH$_3$ | 2 | 6-CH$_3$ | 1 |
| 3.478 | 2-CH$_3$, 4-CF$_3$ | 2 | 6-CH$_3$ | 1 |
| 3.479 | — | — | 6-OCH$_3$ | 1 |
| 3.480 | 2-F | 1 | 6-OCH$_3$ | 1 |
| 3.481 | 3-F | 1 | 6-OCH$_3$ | 1 |
| 3.482 | 4-F | 1 | 6-OCH$_3$ | 1 |
| 3.483 | 2-Cl | 1 | 6-OCH$_3$ | 1 |
| 3.484 | 3-Cl | 1 | 6-OCH$_3$ | 1 |
| 3.485 | 4-Cl | 1 | 6-OCH$_3$ | 1 |
| 3.486 | 2-CH$_3$ | 1 | 6-OCH$_3$ | 1 |
| 3.487 | 3-CH$_3$ | 1 | 6-OCH$_3$ | 1 |
| 3.488 | 4-CH$_3$ | 1 | 6-OCH$_3$ | 1 |
| 3.489 | 2-OCH$_3$ | 1 | 6-OCH$_3$ | 1 |
| 3.490 | 3-OCH$_3$ | 1 | 6-OCH$_3$ | 1 |
| 3.491 | 4-OCH$_3$ | 1 | 6-OCH$_3$ | 1 |
| 3.492 | 2-CF$_3$ | 1 | 6-OCH$_3$ | 1 |
| 3.493 | 3-CF$_3$ | 1 | 6-OCH$_3$ | 1 |
| 3.494 | 4-CF$_3$ | 1 | 6-OCH$_3$ | 1 |
| 3.495 | 2,3-Cl$_2$ | 2 | 6-OCH$_3$ | 1 |
| 3.496 | 2,4-Cl$_2$ | 2 | 6-OCH$_3$ | 1 |
| 3.497 | 2,5-Cl$_2$ | 2 | 6-OCH$_3$ | 1 |
| 3.498 | 2,6-Cl$_2$ | 2 | 6-OCH$_3$ | 1 |
| 3.499 | 3,4-Cl$_2$ | 2 | 6-OCH$_3$ | 1 |
| 3.500 | 3,5-Cl$_2$ | 2 | 6-OCH$_3$ | 1 |
| 3.501 | 2-CH$_3$, 4-Cl | 2 | 6-OCH$_3$ | 1 |
| 3.502 | 2-Cl, 4-CH$_3$ | 2 | 6-OCH$_3$ | 1 |
| 3.503 | 2-CF$_3$, 4-CH$_3$ | 2 | 6-OCH$_3$ | 1 |
| 3.504 | 2-CH$_3$, 4-CF$_3$ | 2 | 6-OCH$_3$ | 1 |
| 3.505 | — | — | 6-CF$_3$ | 1 |
| 3.506 | 2-F | 1 | 6-CF$_3$ | 1 |
| 3.507 | 3-F | 1 | 6-CF$_3$ | 1 |
| 3.508 | 4-F | 1 | 6-CF$_3$ | 1 |
| 3.509 | 2-Cl | 1 | 6-CF$_3$ | 1 |
| 3.510 | 3-Cl | 1 | 6-CF$_3$ | 1 |
| 3.511 | 4-Cl | 1 | 6-CF$_3$ | 1 |
| 3.512 | 2-CH$_3$ | 1 | 6-CF$_3$ | 1 |
| 3.513 | 3-CH$_3$ | 1 | 6-CF$_3$ | 1 |
| 3.514 | 4-CH$_3$ | 1 | 6-CF$_3$ | 1 |
| 3.515 | 2-OCH$_3$ | 1 | 6-CF$_3$ | 1 |
| 3.516 | 3-OCH$_3$ | 1 | 6-CF$_3$ | 1 |
| 3.517 | 4-OCH$_3$ | 1 | 6-CF$_3$ | 1 |
| 3.518 | 2-CF$_3$ | 1 | 6-CF$_3$ | 1 |
| 3.519 | 3-CF$_3$ | 1 | 6-CF$_3$ | 1 |
| 3.520 | 4-CF$_3$ | 1 | 6-CF$_3$ | 1 |
| 3.521 | 2,3-Cl$_2$ | 2 | 6-CF$_3$ | 1 |
| 3.522 | 2,4-Cl$_2$ | 2 | 6-CF$_3$ | 1 |
| 3.523 | 2,5-Cl$_2$ | 2 | 6-CF$_3$ | 1 |
| 3.524 | 2,6-Cl$_2$ | 2 | 6-CF$_3$ | 1 |
| 3.525 | 3,4-Cl$_2$ | 2 | 6-CF$_3$ | 1 |
| 3.526 | 3,5-Cl$_2$ | 2 | 6-CF$_3$ | 1 |
| 3.527 | 2-CH$_3$, 4-Cl | 2 | 6-CF$_3$ | 1 |
| 3.528 | 2-Cl, 4-CH$_3$ | 2 | 6-CF$_3$ | 1 |
| 3.529 | 2-CF$_3$, 4-CH$_3$ | 2 | 6-CF$_3$ | 1 |
| 3.530 | 2-CH$_3$, 4-CF$_3$ | 2 | 6-CF$_3$ | 1 |
| 3.531 | — | — | 3,5-Cl$_2$ | 1 |
| 3.532 | 2-F | 1 | 3,5-Cl$_2$ | 1 |
| 3.533 | 3-F | 1 | 3,5-Cl$_2$ | 1 |
| 3.534 | 4-F | 1 | 3,5-Cl$_2$ | 1 |
| 3.535 | 2-Cl | 1 | 3,5-Cl$_2$ | 1 |
| 3.536 | 3-Cl | 1 | 3,5-Cl$_2$ | 1 |
| 3.537 | 4-Cl | 1 | 3,5-Cl$_2$ | 1 |

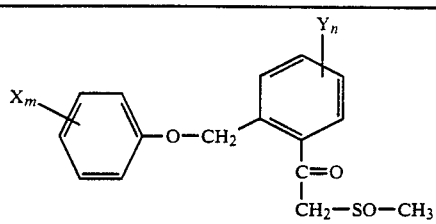

TABLE 3-continued

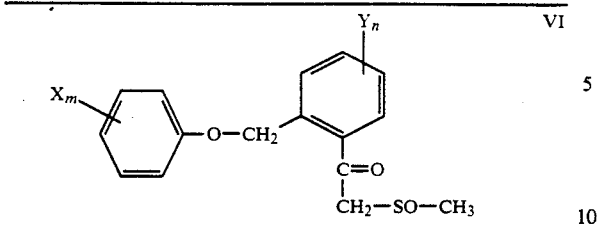

VI

| No. | x | m | Y | n |
|---|---|---|---|---|
| 3.538 | 2-CH$_3$ | 1 | 3,5-Cl$_2$ | 1 |
| 3.539 | 3-CH$_3$ | 1 | 3,5-Cl$_2$ | 1 |
| 3.540 | 4-CH$_3$ | 1 | 3,5-Cl$_2$ | 1 |
| 3.541 | 2-OCH$_3$ | 1 | 3,5-Cl$_2$ | 1 |
| 3.542 | 3-OCH$_3$ | 1 | 3,5-Cl$_2$ | 1 |
| 3.543 | 4-OCH$_3$ | 1 | 3,5-Cl$_2$ | 1 |
| 3.544 | 2-CF$_3$ | 1 | 3,5-Cl$_2$ | 1 |
| 3.545 | 3-CF$_3$ | 1 | 3,5-Cl$_2$ | 1 |
| 3.546 | 4-CF$_3$ | 1 | 3,5-Cl$_2$ | 1 |
| 3.547 | 2,3-Cl$_2$ | 2 | 3,5-Cl$_2$ | 1 |
| 3.548 | 2,4-Cl$_2$ | 2 | 3,5-Cl$_2$ | 1 |
| 3.549 | 2,5-Cl$_2$ | 2 | 3,5-Cl$_2$ | 1 |
| 3.550 | 2,6-Cl$_2$ | 2 | 3,5-Cl$_2$ | 1 |
| 3.551 | 3,4-Cl$_2$ | 2 | 3,5-Cl$_2$ | 1 |
| 3.552 | 3,5-Cl$_2$ | 2 | 3,5-Cl$_2$ | 1 |
| 3.553 | 2-CH$_3$, 4-Cl | 2 | 3,5-Cl$_2$ | 1 |
| 3.554 | 2-Cl, 4-CH$_3$ | 2 | 3,5-Cl$_2$ | 1 |
| 3.555 | 2-CF$_3$, 4-CH$_3$ | 2 | 3,5-Cl$_2$ | 1 |
| 3.556 | 2-CH$_3$, 4-CF$_3$ | 2 | 3,5-Cl$_2$ | 1 |
| 3.557 | — | — | 3-Cl, 5-F | 1 |
| 3.558 | 2-F | 1 | 3-Cl, 5-F | 1 |
| 3.559 | 3-F | 1 | 3-Cl, 5-F | 1 |
| 3.560 | 4-F | 1 | 3-Cl, 5-F | 1 |
| 3.561 | 2-Cl | 1 | 3-Cl, 5-F | 1 |
| 3.562 | 3-Cl | 1 | 3-Cl, 5-F | 1 |
| 3.563 | 4-Cl | 1 | 3-Cl, 5-F | 1 |
| 3.564 | 2-CH$_3$ | 1 | 3-Cl, 5-F | 1 |
| 3.565 | 3-CH$_3$ | 1 | 3-Cl, 5-F | 1 |
| 3.566 | 4-CH$_3$ | 1 | 3-Cl, 5-F | 1 |
| 3.567 | 2-OCH$_3$ | 1 | 3-Cl, 5-F | 1 |
| 3.568 | 3-OCH$_3$ | 1 | 3-Cl, 5-F | 1 |
| 3.569 | 4-OCH$_3$ | 1 | 3-Cl, 5-F | 1 |
| 3.570 | 2-CF$_3$ | 1 | 3-Cl, 5-F | 1 |
| 3.571 | 3-CF$_3$ | 1 | 3-Cl, 5-F | 1 |
| 3.572 | 4-CF$_3$ | 1 | 3-Cl, 5-F | 1 |
| 3.573 | 2,3-Cl$_2$ | 2 | 3-Cl, 5-F | 1 |
| 3.574 | 2,4-Cl$_2$ | 2 | 3-Cl, 5-F | 1 |
| 3.575 | 2,5-Cl$_2$ | 2 | 3-Cl, 5-F | 1 |
| 3.576 | 2,6-Cl$_2$ | 2 | 3-Cl, 5-F | 1 |
| 3.577 | 3,4-Cl$_2$ | 2 | 3-Cl, 5-F | 1 |
| 3.578 | 3,5-Cl$_2$ | 2 | 3-Cl, 5-F | 1 |
| 3.579 | 2-CH$_3$, 4-Cl | 2 | 3-Cl, 5-F | 1 |
| 3.580 | 2-Cl, 4-CH$_3$ | 2 | 3-Cl, 5-F | 1 |
| 3.581 | 2-CF$_3$, 4-CH$_3$ | 2 | 3-Cl, 5-F | 1 |
| 3.582 | 2-CH$_3$, 4-CF$_3$ | 2 | 3-Cl, 5-F | 1 |
| 3.583 | — | — | 3-F, 5-Cl | 1 |
| 3.584 | 2-F | 1 | 3-F, 5-Cl | 1 |
| 3.585 | 3-F | 1 | 3-F, 5-Cl | 1 |
| 3.586 | 4-F | 1 | 3-F, 5-Cl | 1 |
| 3.587 | 2-Cl | 1 | 3-F, 5-Cl | 1 |
| 3.588 | 3-Cl | 1 | 3-F, 5-Cl | 1 |
| 3.589 | 4-Cl | 1 | 3-F, 5-Cl | 1 |
| 3.590 | 2-CH$_3$ | 1 | 3-F, 5-Cl | 1 |
| 3.591 | 3-CH$_3$ | 1 | 3-F, 5-Cl | 1 |
| 3.592 | 4-CH$_3$ | 1 | 3-F, 5-Cl | 1 |
| 3.593 | 2-OCH$_3$ | 1 | 3-F, 5-Cl | 1 |
| 3.594 | 3-OCH$_3$ | 1 | 3-F, 5-Cl | 1 |
| 3.595 | 4-OCH$_3$ | 1 | 3-F, 5-Cl | 1 |
| 3.596 | 2-CF$_3$ | 1 | 3-F, 5-Cl | 1 |
| 3.597 | 3-CF$_3$ | 1 | 3-F, 5-Cl | 1 |
| 3.598 | 4-CF$_3$ | 1 | 3-F, 5-Cl | 1 |
| 3.599 | 2,3-Cl$_2$ | 2 | 3-F, 5-Cl | 1 |
| 3.600 | 2,4-Cl$_2$ | 2 | 3-F, 5-Cl | 1 |
| 3.601 | 2,5-Cl$_2$ | 2 | 3-F, 5-Cl | 1 |
| 3.602 | 2,6-Cl$_2$ | 2 | 3-F, 5-Cl | 1 |
| 3.603 | 3,4-Cl$_2$ | 2 | 3-F, 5-Cl | 1 |
| 3.604 | 3,5-Cl$_2$ | 2 | 3-F, 5-Cl | 1 |
| 3.605 | 2-CH$_3$, 4-Cl | 2 | 3-F, 5-Cl | 1 |
| 3.606 | 2-Cl, 4-CH$_3$ | 2 | 3-F, 5-Cl | 1 |
| 3.607 | 2-CF$_3$, 4-CH$_3$ | 2 | 3-F, 5-Cl | 1 |
| 3.608 | 2-CH$_3$, 4-CF$_3$ | 2 | 3-F, 5-Cl | 1 |
| 3.609 | — | — | 3,5,6-F$_3$ | 1 |
| 3.610 | 2-F | 1 | 3,5,6-F$_3$ | 1 |
| 3.611 | 3-F | 1 | 3,5,6-F$_3$ | 1 |
| 3.612 | 4-F | 1 | 3,5,6-F$_3$ | 1 |
| 3.613 | 2-Cl | 1 | 3,5,6-F$_3$ | 1 |
| 3.614 | 3-Cl | 1 | 3,5,6-F$_3$ | 1 |
| 3.615 | 4-Cl | 1 | 3,5,6-F$_3$ | 1 |
| 3.616 | 2-CH$_3$ | 1 | 3,5,6-F$_3$ | 1 |
| 3.617 | 3-CH$_3$ | 1 | 3,5,6-F$_3$ | 1 |
| 3.618 | 4-CH$_3$ | 1 | 3,5,6-F$_3$ | 1 |
| 3.619 | 2-OCH$_3$ | 1 | 3,5,6-F$_3$ | 1 |
| 3.620 | 3-OCH$_3$ | 1 | 3,5,6-F$_3$ | 1 |
| 3.621 | 4-OCH$_3$ | 1 | 3,5,6-F$_3$ | 1 |
| 3.622 | 2-CF$_3$ | 1 | 3,5,6-F$_3$ | 1 |
| 3.623 | 3-CF$_3$ | 1 | 3,5,6-F$_3$ | 1 |
| 3.624 | 4-CF$_3$ | 1 | 3,5,6-F$_3$ | 1 |
| 3.625 | 2,3-Cl$_2$ | 2 | 3,5,6-F$_3$ | 1 |
| 3.626 | 2,4-Cl$_2$ | 2 | 3,5,6-F$_3$ | 1 |
| 3.627 | 2,5-Cl$_2$ | 2 | 3,5,6-F$_3$ | 1 |
| 3.628 | 2,6-Cl$_2$ | 2 | 3,5,6-F$_3$ | 1 |
| 3.629 | 3,4-Cl$_2$ | 2 | 3,5,6-F$_3$ | 1 |
| 3.630 | 3,5-Cl$_2$ | 2 | 3,5,6-F$_3$ | 1 |
| 3.631 | 2-CH$_3$, 4-Cl | 2 | 3,5,6-F$_3$ | 1 |
| 3.632 | 2-Cl, 4-CH$_3$ | 2 | 3,5,6-F$_3$ | 1 |
| 3.633 | 2-CF$_3$, 4-CH$_3$ | 2 | 3,5,6-F$_3$ | 1 |
| 3.634 | 2-CH$_3$, 4-CF$_3$ | 2 | 3,5,6-F$_3$ | 1 |
| 3.635 | — | — | 3,5-(CH$_3$)$_2$ | 1 |
| 3.636 | 2-F | 1 | 3,5-(CH$_3$)$_2$ | 1 |
| 3.637 | 3-F | 1 | 3,5-(CH$_3$)$_2$ | 1 |
| 3.638 | 4-F | 1 | 3,5-(CH$_3$)$_2$ | 1 |
| 3.639 | 2-Cl | 1 | 3,5-(CH$_3$)$_2$ | 1 |
| 3.640 | 3-Cl | 1 | 3,5-(CH$_3$)$_2$ | 1 |
| 3.641 | 4-Cl | 1 | 3,5-(CH$_3$)$_2$ | 1 |
| 3.642 | 2-CH$_3$ | 1 | 3,5-(CH$_3$)$_2$ | 1 |
| 3.643 | 3-CH$_3$ | 1 | 3,5-(CH$_3$)$_2$ | 1 |
| 3.644 | 4-CH$_3$ | 1 | 3,5-(CH$_3$)$_2$ | 1 |
| 3.645 | 2-OCH$_3$ | 1 | 3,5-(CH$_3$)$_2$ | 1 |
| 3.646 | 3-OCH$_3$ | 1 | 3,5-(CH$_3$)$_2$ | 1 |
| 3.647 | 4-OCH$_3$ | 1 | 3,5-(CH$_3$)$_2$ | 1 |
| 3.648 | 2-CF$_3$ | 1 | 3,5-(CH$_3$)$_2$ | 1 |
| 3.649 | 3-CF$_3$ | 1 | 3,5-(CH$_3$)$_2$ | 1 |
| 3.650 | 4-CF$_3$ | 1 | 3,5-(CH$_3$)$_2$ | 1 |
| 3.651 | 2,3-Cl$_2$ | 2 | 3,5-(CH$_3$)$_2$ | 1 |
| 3.652 | 2,4-Cl$_2$ | 2 | 3,5-(CH$_3$)$_2$ | 1 |
| 3.653 | 2,5-Cl$_2$ | 2 | 3,5-(CH$_3$)$_2$ | 1 |
| 3.654 | 2,6-Cl$_2$ | 2 | 3,5-(CH$_3$)$_2$ | 1 |
| 3.655 | 3,4-Cl$_2$ | 2 | 3,5-(CH$_3$)$_2$ | 1 |
| 3.656 | 3,5-Cl$_2$ | 2 | 3,5-(CH$_3$)$_2$ | 1 |
| 3.657 | 2-CH$_3$, 4-Cl | 2 | 3,5-(CH$_3$)$_2$ | 1 |
| 3.658 | 2-Cl, 4-CH$_3$ | 2 | 3,5-(CH$_3$)$_2$ | 1 |
| 3.659 | 2-CF$_3$, 4-CH$_3$ | 2 | 3,5-(CH$_3$)$_2$ | 1 |
| 3.660 | 2-CH$_3$, 4-CF$_3$ | 2 | 3,5-(CH$_3$)$_2$ | 1 |
| 3.661 | — | — | 5,6-(CH$_3$)$_2$ | 1 |
| 3.662 | 2-F | 1 | 5,6-(CH$_3$)$_2$ | 1 |
| 3.663 | 3-F | 1 | 5,6-(CH$_3$)$_2$ | 1 |
| 3.664 | 4-F | 1 | 5,6-(CH$_3$)$_2$ | 1 |
| 3.665 | 2-Cl | 1 | 5,6-(CH$_3$)$_2$ | 1 |
| 3.666 | 3-Cl | 1 | 5,6-(CH$_3$)$_2$ | 1 |
| 3.667 | 4-Cl | 1 | 5,6-(CH$_3$)$_2$ | 1 |
| 3.668 | 2-CH$_3$ | 1 | 5,6-(CH$_3$)$_2$ | 1 |
| 3.669 | 3-CH$_3$ | 1 | 5,6-(CH$_3$)$_2$ | 1 |
| 3.670 | 4-CH$_3$ | 1 | 5,6-(CH$_3$)$_2$ | 1 |
| 3.671 | 2-OCH$_3$ | 1 | 5,6-(CH$_3$)$_2$ | 1 |
| 3.672 | 3-OCH$_3$ | 1 | 5,6-(CH$_3$)$_2$ | 1 |
| 3.673 | 4-OCH$_3$ | 1 | 5,6-(CH$_3$)$_2$ | 1 |
| 3.674 | 2-CF$_3$ | 1 | 5,6-(CH$_3$)$_2$ | 1 |
| 3.675 | 3-CF$_3$ | 1 | 5,6-(CH$_3$)$_2$ | 1 |
| 3.676 | 4-CF$_3$ | 1 | 5,6-(CH$_3$)$_2$ | 1 |
| 3.677 | 2,3-Cl$_2$ | 2 | 5,6-(CH$_3$)$_2$ | 1 |

TABLE 3-continued

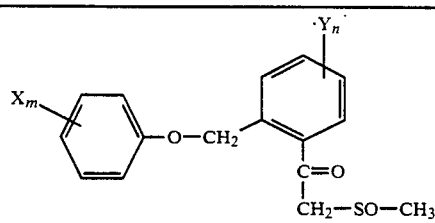

VI

| No. | x | m | Y | n |
|---|---|---|---|---|
| 3.678 | 2,4-Cl$_2$ | 2 | 5,6-(CH$_3$)$_2$ | 1 |
| 3.679 | 2,5-Cl$_2$ | 2 | 5,6-(CH$_3$)$_2$ | 1 |
| 3.680 | 2,6-Cl$_2$ | 2 | 5,6-(CH$_3$)$_2$ | 1 |
| 3.681 | 3,4-Cl$_2$ | 2 | 5,6-(CH$_3$)$_2$ | 1 |
| 3.682 | 3,5-Cl$_2$ | 2 | 5,6-(CH$_3$)$_2$ | 1 |
| 3.683 | 2-CH$_3$, 4-Cl | 2 | 5,6-(CH$_3$)$_2$ | 1 |
| 3.684 | 2-Cl, 4-CH$_3$ | 2 | 5,6-(CH$_3$)$_2$ | 1 |
| 3.685 | 2-CF$_3$, 4-CH$_3$ | 2 | 5,6-(CH$_3$)$_2$ | 1 |
| 3.686 | 2-CH$_3$, 4-CF$_3$ | 2 | 5,6-(CH$_3$)$_2$ | 1 |
| 3.687 | — | — | 3,4-(CH$_3$)$_2$ | 1 |
| 3.688 | 2-F | 1 | 3,4-(CH$_3$)$_2$ | 1 |
| 3.689 | 3-F | 1 | 3,4-(CH$_3$)$_2$ | 1 |
| 3.690 | 4-F | 1 | 3,4-(CH$_3$)$_2$ | 1 |
| 3.691 | 2-Cl | 1 | 3,4-(CH$_3$)$_2$ | 1 |
| 3.692 | 3-Cl | 1 | 3,4-(CH$_3$)$_2$ | 1 |
| 3.693 | 4-Cl | 1 | 3,4-(CH$_3$)$_2$ | 1 |
| 3.694 | 2-CH$_3$ | 1 | 3,4-(CH$_3$)$_2$ | 1 |
| 3.695 | 3-CH$_3$ | 1 | 3,4-(CH$_3$)$_2$ | 1 |
| 3.696 | 4-CH$_3$ | 1 | 3,4-(CH$_3$)$_2$ | 1 |
| 3.697 | 2-OCH$_3$ | 1 | 3,4-(CH$_3$)$_2$ | 1 |
| 3.698 | 3-OCH$_3$ | 1 | 3,4-(CH$_3$)$_2$ | 1 |
| 3.699 | 4-OCH$_3$ | 1 | 3,4-(CH$_3$)$_2$ | 1 |
| 3.700 | 2-CF$_3$ | 1 | 3,4-(CH$_3$)$_2$ | 1 |
| 3.701 | 3-CF$_3$ | 1 | 3,4-(CH$_3$)$_2$ | 1 |
| 3.702 | 4-CF$_3$ | 1 | 3,4-(CH$_3$)$_2$ | 1 |
| 3.703 | 2,3-Cl$_2$ | 2 | 3,4-(CH$_3$)$_2$ | 1 |
| 3.704 | 2,4-Cl$_2$ | 2 | 3,4-(CH$_3$)$_2$ | 1 |
| 3.705 | 2,5-Cl$_2$ | 2 | 3,4-(CH$_3$)$_2$ | 1 |
| 3.706 | 2,6-Cl$_2$ | 2 | 3,4-(CH$_3$)$_2$ | 1 |
| 3.707 | 3,4-Cl$_2$ | 2 | 3,4-(CH$_3$)$_2$ | 1 |
| 3.708 | 3,5-Cl$_2$ | 2 | 3,4-(CH$_3$)$_2$ | 1 |
| 3.709 | 2-CH$_3$, 4-Cl | 2 | 3,4-(CH$_3$)$_2$ | 1 |
| 3.710 | 2-Cl, 4-CH$_3$ | 2 | 3,4-(CH$_3$)$_2$ | 1 |
| 3.711 | 2-CF$_3$, 4-CH$_3$ | 2 | 3,4-(CH$_3$)$_2$ | 1 |
| 3.712 | 2-CH$_3$, 4-CF$_3$ | 2 | 3,4-(CH$_3$)$_2$ | 1 |
| 3.713 | — | — | 4,6-(OCH$_3$)$_2$ | 1 |
| 3.714 | 2-F | 1 | 4,6-(OCH$_3$)$_2$ | 1 |
| 3.715 | 3-F | 1 | 4,6-(OCH$_3$)$_2$ | 1 |
| 3.716 | 4-F | 1 | 4,6-(OCH$_3$)$_2$ | 1 |
| 3.717 | 2-Cl | 1 | 4,6-(OCH$_3$)$_2$ | 1 |
| 3.718 | 3-Cl | 1 | 4,6-(OCH$_3$)$_2$ | 1 |
| 3.719 | 4-Cl | 1 | 4,6-(OCH$_3$)$_2$ | 1 |
| 3.720 | 2-CH$_3$ | 1 | 4,6-(OCH$_3$)$_2$ | 1 |
| 3.721 | 3-CH$_3$ | 1 | 4,6-(OCH$_3$)$_2$ | 1 |
| 3.722 | 4-CH$_3$ | 1 | 4,6-(OCH$_3$)$_2$ | 1 |
| 3.723 | 2-OCH$_3$ | 1 | 4,6-(OCH$_3$)$_2$ | 1 |
| 3.724 | 3-OCH$_3$ | 1 | 4,6-(OCH$_3$)$_2$ | 1 |
| 3.725 | 4-OCH$_3$ | 1 | 4,6-(OCH$_3$)$_2$ | 1 |
| 3.726 | 2-CF$_3$ | 1 | 4,6-(OCH$_3$)$_2$ | 1 |
| 3.727 | 3-CF$_3$ | 1 | 4,6-(OCH$_3$)$_2$ | 1 |
| 3.728 | 4-CF$_3$ | 1 | 4,6-(OCH$_3$)$_2$ | 1 |
| 3.729 | 2,3-Cl$_2$ | 2 | 4,6-(OCH$_3$)$_2$ | 1 |
| 3.730 | 2,4-Cl$_2$ | 2 | 4,6-(OCH$_3$)$_2$ | 1 |
| 3.731 | 2,5-Cl$_2$ | 2 | 4,6-(OCH$_3$)$_2$ | 1 |
| 3.732 | 2,6-Cl$_2$ | 2 | 4,6-(OCH$_3$)$_2$ | 1 |
| 3.733 | 3,4-Cl$_2$ | 2 | 4,6-(OCH$_3$)$_2$ | 1 |
| 3.734 | 3,5-Cl$_2$ | 2 | 4,6-(OCH$_3$)$_2$ | 1 |
| 3.735 | 2-CH$_3$, 4-Cl | 2 | 4,6-(OCH$_3$)$_2$ | 1 |
| 3.736 | 2-Cl, 4-CH$_3$ | 2 | 4,6-(OCH$_3$)$_2$ | 1 |
| 3.737 | 2-CF$_3$, 4-CH$_3$ | 2 | 4,6-(OCH$_3$)$_2$ | 1 |
| 3.738 | 2-CH$_3$, 4-CF$_3$ | 2 | 4,6-(OCH$_3$)$_2$ | 1 |

The α-keto carboxylic esters VII are valuable intermediates, especially for the synthesis of E-oxime ethers of phenylglyoxylic esters I

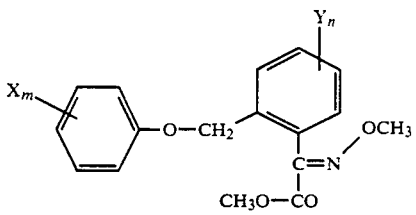

I which are used in crop protection, preferably as fungicides (cf. EP-A 253 213 and EP-A 254 426).

The final products I can be prepared by reacting the α-keto carboxylic esters VII with O-methylhydroxylamine or one of its acid addition salts, and the resulting E/Z isomer mixture is treated, simultaneously or subsequently, with acid to rearrange the Z to the E isomers:

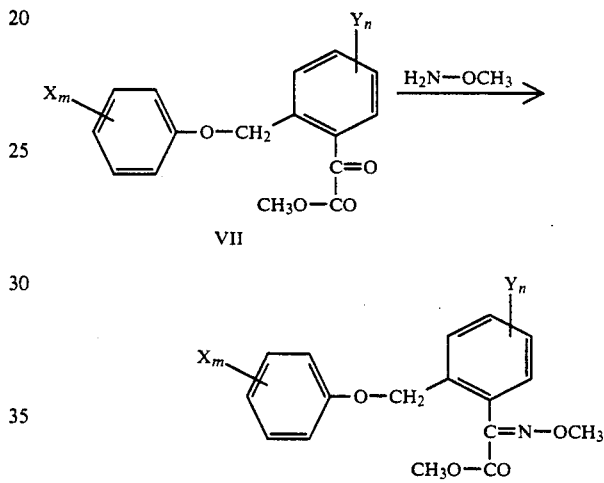

EXAMPLE 10 (precursors)

Precursor α
2-(2-Methylphenoxymethyl)benzoic acid

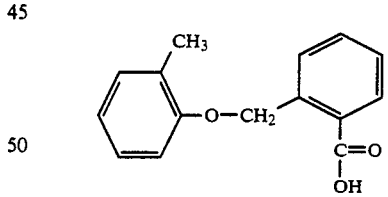

A mixture of 160 g (1.48 mol) of o-cresol, 106 g of 85% by weight aqueous potassium hydroxide solution and 1.5 l of xylene was refluxed while continuously removing the water. The mixture was then cooled to 100° C. and, at this temperature, 195 g (1.45 mol) of phthalide and 57 ml of dimethylformamide were added. The resulting mixture was then heated at 100° C. for 15 hours, subsequently cooled to 20°-25° C. and extracted twice with 2 l of water each time, and then 140 ml of 38% by weight aqueous hydrochloric acid were added. The crystals which formed were separated off, washed with 500 ml of water and dried. The product was purified by dissolving in 550 ml of hot acetone and re-precipitation by adding 3 l of water. Yield: 85%; melting point 154° C.;

¹H NMR (in CDCl₃, TMS as internal standard): 2.39 ppm (s,3H); 5.38 ppm (S,2H); 6.9-8.2 ppm (m,8H).

Precursor β

Methyl 2-(2-methylphenoxymethyl)benzoate

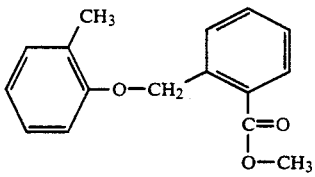

12.5 g (0.1 mol) of thionyl chloride were added dropwise to a solution of 24.3 g (0.1 mol) of 2-(2-methylphenoxymethyl)benzoic acid in 100 ml of methanol. After 4.5 hours at 20°-25° C., the solvent was removed. Yield: 89%; melting point 51° C.

¹H NMR (in CDCl₃, TMS as internal standard): 2.4 ppm (s,3H); 3.98 ppm (s,3H); 5.58 ppm (s,2H); 6.95-8.05 ppm (m,8H).

EXAMPLE 11 (according to the invention)

Methyl 2-(2-methylphenoxymethyl)phenylglyoxylate

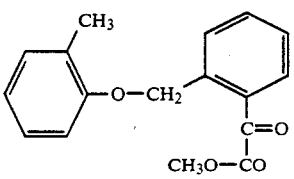

Step (a)

A dry flask was charged with 64 ml (0.9 mol) of dimethyl sulfoxide, and 8.6 g (0.12 mol) of sodium methylate were added. The mixture was heated to 65° C. and, after 2 hours at this temperature, a solution of 20.5 g (0.08 mol) of methyl 2-(2-methylphenoxymethyl)benzoate in 64 ml of dimethyl sulfoxide was added. The mixture was then stirred at 20°-25° C. for about 15 hours, after which the solvent was removed under reduced pressure and the residue was poured into icewater. Acidification of the aqueous phase with glacial acetic acid (pH=2) resulted in the formation of crystals, which were separated off, washed successively with saturated aqueous sodium bicarbonate solution, water and diisopropyl ether and were dried. Yield: 77% of 2-(2-methylphenoxymethyl)-ω-methylsulfinylacetophenone;

¹H NMR (in CDCl₃, TMS as internal standard): 2.3 ppm (s,3H); 2.8 ppm (s,3H); 4.4 ppm (q,2H); 5.4 ppm (s,2H); 6.9-8.0 ppm (m,8H).

Steps (b) and (c)

Variant 11.1

12.6 g (44 mmol) of 3,3-dimethyl-5,5-dibromohydantoin were added to a suspension of 24.1 g (79.8 mmol) of 2-(2-methylphenoxymethyl)-ω-methylsulfinylacetophenone in 400 ml of acetone. After stirring at 20°-25° C. for 30 minutes, the solvent was removed under reduced pressure, and 500 ml of methanol and 40 ml of concentrated aqueous hydrochloric acid were added to the residue. The mixture was then stirred at 20°-25° C. for 20 hours, after which the solvent was removed under reduced pressure and 500 ml of ice-cold water were added to the residue. The aqueous phase was extracted three times with 150 ml of methylene chloride each time, after which the combined extracts were worked up to the product in a conventional manner. The result was a viscous oil which slowly crystallized. Yield: 85%.

Variant 11.2

30.2 g (0.1 mol) of 2-(2-methylphenoxymethyl)-ω-methylsulfinylacetophenone were added at room temperature to a solution of 36 g (0.2 mol) of 30% by weight sodium methanolate solution in 150 ml of methanol. To this was added dropwise at 20° C. a solution of 19.8 g (0.124 mol) of bromine in 50 ml of methanol. After the addition was complete, the mixture was stirred at 20° C. for 30 min and then 20 ml of concentrated aqueous hydrochloric acid were added dropwise. The mixture was then refluxed (about 65° C.) for 30 min. After cooling, 500 ml of ethyl acetate were added to the mixture, which was then washed twice with 100 ml of water each time. The organic phase was dried over Na₂SO₄ and concentrated. The crude product was purified by chromatography on 300 g of silica gel with a hexane/ethyl acetate (20:1) mixture as eluent. Yield: 54% (colorless crystals).

¹H NMR (in CDCl₃, TMS as internal standard): 2.3 ppm (s,3H; CH₃); 3.97 ppm (s,3H; OCH₃); 5.2 ppm (s,2H; CH₂); 6.8-7.9 ppm (m,8H; aromat. protons).

EXAMPLE 12 (Comparative examples from the prior art)

12.1) Grignard reaction of 2-(2-methylphenoxymethyl)-bromobenzene with methoxalylimidazole (cf. EP-A 280 185)

110.8 g (0.4 mol) of 2-(2-methylphenoxymethyl)-bromobenzene in 200 ml of tetrahydrofuran were reacted with 10.4 g (0.4 mol) of magnesium turnings. The resulting Grignard compound was added dropwise at −78° C. to a solution of 61.6 g (0.4 mol) of methoxalylimidazole in 500 ml of tetrahydrofuran. After the mixture had warmed to 20°-25° C. it was stirred for about 15 hours and then poured into 800 ml of icewater. The solution was extracted three times with 200 ml of diethyl ether each time, after which the combined ether phases were washed to neutrality, dried and concentrated. The crude product was purified by chromatography on 190 g of silica gel with cyclohexane/ethyl acetate (9:1) as eluent. Yield: 37.8%.

12.2) Reaction of 2-(2-methylphenoxymethyl)benzoyl cyanide with catalysis by NaBr (cf. US-A 4 234 739).

A solution of 20.5 g (81 mmol) of 2-(2-methylphenoxymethyl)benzoyl cyanide in 80 ml of methylene chloride was added dropwise at 20°-25° C. to a mixture of 19.6 ml of 85% by weight sulfuric acid and 1.09 g (0.01 mol) of sodium bromide. 38.9 ml (0.95 mol) of methanol were then added to the mixture at 40° C., after which it was stirred at this temperature for 3 hours. HPLC analysis of a sample showed that the result was not methyl 2-(2-methylphenoxymethyl)phenylglyoxylate but a quantitative yield of methyl 2-(2-methylphenoxymethyl)-benzoate.

After addition of 180 ml of water, the resulting mixture was extracted three times with 50 ml of methylene chloride each time, after which the combined organic phases were worked up to the product in a conventional manner.

¹H NMR (in CDCl₃, TMS as internal standard): 2.33 ppm (s,3H); 3.87 ppm (s,3H); 5.48 ppm (s,2H); 6.83-6.01 ppm (m,8H).

The present invention furthermore relates to a novel process for preparing arylglyoxylic esters of the formula VIIa Ar-CO-CO-OCH₃　　　　VIIa

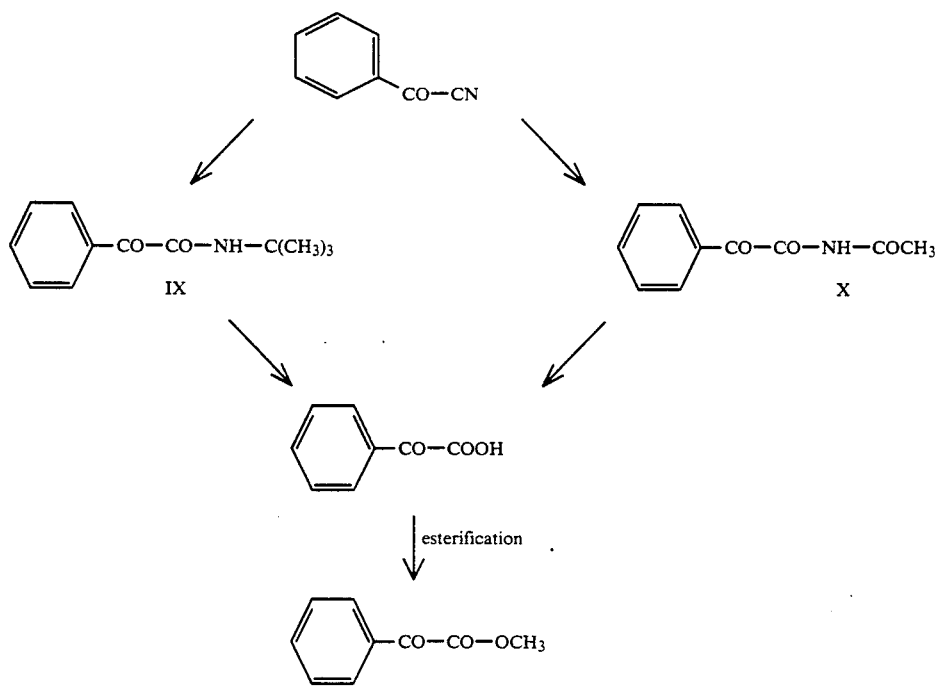

where
Ar is phenyl or naphthyl, each of which can carry from one to four substituents selected from the group comprising halogen, alkyl, haloalkyl, alkoxy, haloalkoxy, alkoxyalkyl, phenyl, phenoxy, benzyloxy, naphthoxy, phenoxyalkyl, benzyloxyalkyl and naphthoxyalkyl, where the last seven substituents can be present only once and can carry from one to three of the following: halogen, alkyl, alkoxy, phenyl, phenoxy, plus as many halogen atoms as there are other carbon atoms which can be substituted Various processes for preparing aromatic α-keto esters are described in the literature.

Angew. Chemie 68 (1956) 430 and idem 94 (1982) 1, Org. Synth. 24 (1944) 16 and J. Org. Chem. 29 (1964) 278 describe methods of hydrolyzing benzoyl cyanides with concentrated mineral acids and converting the resulting keto carboxylic acids into phenylglyoxylic esters, but large amounts of byproducts are formed, especially benzoic esters:

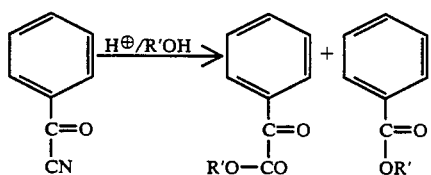

US-A 4,234,739, DE-A 2,708,189 and Tetrah. Lett. (1980) 3539 disclose that the formation of the benzoic esters can be substantially suppressed in several cases by adding halide.

It is also known to convert benzoyl cyanides either into the corresponding keto tert-butylamides IX by the Ritter reaction (cf. EP-A 034,240) or into keto N-acylamides X (cf. EP-A 35,707). Both compounds can then be converted into keto carboxylic acids and keto esters:

However, these processes are unsuitable for preparing the α-keto carboxylic esters VIIa.

It is an object of the present invention to improve access to the compounds VIIa.

We have found that his object is achieved by a novel process for preparing arylglyoxylic esters VIIa, which comprises
a) reacting an acyl cyanide of the formula VI Ar-CO-CN　　　　VI with hydrogen chloride and tert-butyl methyl ether and
b) if required, hydrolyzing the byproduct arylglyoxylamide of the formula VIIb Ar-CO-CO-NHR　　　　VIIb where R is hydrogen or acyl, under acidic conditions in the presence of methanol and
c) if required, hydrolyzing the byproduct dimethyl acetal of the arylglyoxylic ester of the formula VIIc

We have also found novel o-phenoxymethylglyoxylic esters of the formula VIIa'

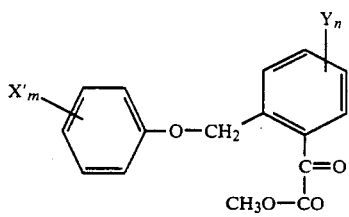

where
X' and Y are each halogen, $C_1$-$C_4$-alkyl, $C_1$-$C_4$-alkoxy or trifluoromethyl;
m is an integer from 0 to 4;
n is an integer from 0 to 3;
with the proviso that n can be 0 only when
X' is 2-chloro, 2-fluoro, 2-methyl, 4-methyl, 4-tertbutyl, 2-methoxy or 2-trifluoromethyl and m is 0 or 1 or X' is 2,4-dichloro or 4-chloro-2-methyl and m is 2, as intermediates.

The acyl cyanides of the formula VI used as starting materials can be obtained, for example, by the following process in which the individual steps have been disclosed:

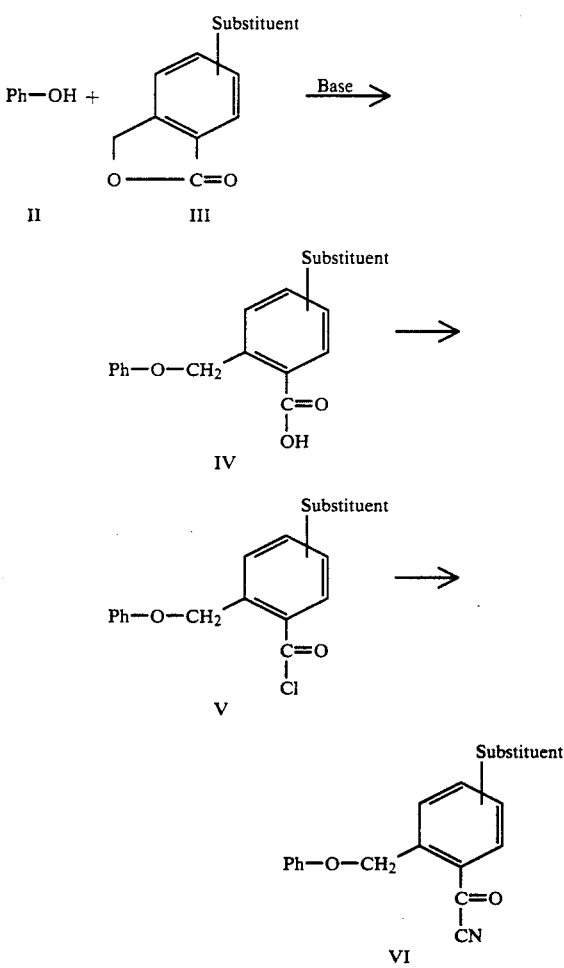

Ph is unsubstituted or substituted phenyl or naphthyl.

In the first stage of this process, phenols, biphenols or naphthols of the formula II are reacted with lactones of the formula III, preferably under basic conditions [cf., for example, Coll. Czech. Chem. Commun. 32 (1967) 3448]. The resulting o-phenoxymethylbenzoic acids IV are expediently converted into their chlorides V (cf. Organikum, VEB Deutscher Verlag der Wissenschaften, 16th edition, Berlin 1986, page 423 et seq.) which are then converted into the corresponding acyl cyanides VI (see also Preparation Example 1, precursors γ, δ and ξ).

Step (a) of the process according to the invention is usually carried out in the absence of water in an excess of tert-butyl methyl ether, if required in the presence of an inert solvent or diluent, for example in a chlorohydrocarbon such as dichloromethane, trichloromethane, tetrachloromethane or 1,2-dichloroethane, or in an aromatic hydrocarbon such as toluene or o-, m- or p-xylene. It is preferable to use tert-butyl methyl ether.

The hydrogen chloride is expediently passed as gas into the solution of the acyl cyanide VI.

All the reactants are normally employed in at least the stoichiometric ratio. The following amounts, based on the amount of VI, are particularly preferred:

from 2 to 20 times, especially 8 to 12 times, the amount of hydrochloric acid;
from 3 to 15 times the amount of inert solvent;
from 4 to 15 times the amount of methyl tertbutyl ether. If tert-butyl methyl ether is used without solvent, it can also be present in a larger excess.

If required, the reaction can also be carried out in the presence of acetic anhydride. The amount of acetic anhydride is not critical and thus amounts up to about a 2-fold molar excess based on the amount of VI are expediently employed.

The reaction is generally carried out under atmospheric pressure, in which case it is advisable to carry it out at from −20° to 60° C., in particular from −5° to 30° C.

The process according to the invention may give arylglyoxylamides VIIb as byproducts. If required, they can be hydrolyzed under acidic conditions in the presence of methanol (step b), suitable acids preferably being strong mineral acids, especially hydrochloric acid and sulfuric acid.

The crude product mixture from step (a) is preferably hydrolyzed, without isolation or after isolation, in an inert organic solvent or diluent as mentioned for stage (a). The following amounts, based on the amount of VI, are particularly preferred in step (b):
from 3 to 10 times the amount of methanol;
from 1 to 15 times the amount, in particular from 3 to 10 times the amount, of hydrochloric acid or sulfuric acid.

This step is also generally carried out under atmospheric pressure, and it is advisable to carry it out at from −20° to 100° C., in particular from 20° to 80° C.

The conditions of step (b) may give small amounts of the corresponding dimethyl acetals of the arylglyoxylic esters- VIIc as byproducts. If required, they can be hydrolyzed to give the arylglyoxylic esters VIIa.

As a rule, the hydrolysis is carried out under acidic conditions, expediently in an inert organic solvent or diluent as mentioned for step (a), preferably in dichloromethane, 1,2-dichloroethane or toluene. The reaction is very particularly preferably carried out in a two-phase system composed of aqueous acid and of an organic solvent.

Suitable acids are organic acids such as acetic acid, trifluoroacetic acid and p-toluenesulfonic acid, and mineral acids such as hydrochloric acid, sulfuric acid and phosphoric acid, with hydrochloric acid and sulfuric acid being preferred. It is normally advisable to use a 2-12 normal aqueous solution of the acid.

The amount of acid is generally from about 10 to 500 mol% based on the amount of VI.

The reaction is normally carried out under atmospheric pressure, and it is advisable to carry it out at from −20° to 80° C., in particular from 0° to 40° C.

The process according to the invention can be carried out either continuously or batchwise. When carried out continuously, the reactants are passed, for example, through a tubular reactor or cascades of stirred vessels.

The process according to the invention gives the arylglyoxylic esters VIIa in high yields and in very high purity.

The described method of preparation can be used successfully to synthesize all arylglyoxylic esters VIIa complying with the definition, especially those in which Ar is phenyl or naphthyl, both of which can carry from one to four substituents selected from the following group:

from one to three halogen atoms such as fluorine, chlorine, bromine and iodine, especially fluorine and chlorine;
from one to three branched or unbranched alkyl substituents, especially $C_1$-$C_4$-alkyl such as methyl, ethyl, n-propyl, isopropyl and n-butyl;
from one to three partially or completely halogenated alkyl substituents, especially $C_1$-$C_4$-alkyl such as fluoromethyl, chloromethyl, trifluoromethyl, trichloromethyl, 1,1,2-trichloroethyl and pentachloroethyl;
from one to three branched or unbranched alkoxy substituents, especially $C_1$-$C_4$-alkoxy such as methoxy, ethoxy, n-propoxy, isopropoxy and n-butoxy;
from one to three partially or completely halogenated alkoxy substituents, especially $C_1$-$C_4$-alkoxy such as trifluoromethoxy and trichloromethoxy;
from one to three branched or unbranched alkoxyalkyl substituents, especially $C_1$-$C_4$-alkoxy-$C_1$-$C_4$-alkyl such as methoxymethyl, ethoxymethyl, n-propoxymethyl, n-butoxymethyl, methoxyethyl, ethoxyethyl, n-propoxyethyl and n-butoxyethyl;
and
one phenyl, phenoxy, benzyloxy, naphthoxy or phenoxyalkyl, especially phenoxy-$C_1$-$C_4$-alkyl such as phenoxymethyl and phenoxyethyl, benzyloxyalkyl, especially benzyloxy-$C_1$-$C_4$-alkyl such as benzyloxymethyl and benzyloxyethyl, or naphthoxyalkyl, especially naphthoxy-$C_1$-$C_4$-alkyl such as naphthoxymethyl and naphthoxyethyl,
where the last seven substituents can carry from one to three of the following: three halogens as mentioned above, especially fluorine and chlorine, three alkyl radicals, especially $C_1$-$C_4$-alkyl as mentioned above, three alkoxy radicals, especially $C_1$-$C_4$-alkoxy as mentioned above, one phenyl and one phenoxy, plus as many halogen atoms as mentioned above, especially fluorine and chlorine, as there are other carbon atoms which can be substituted.

Particularly suitable compounds VIIa are those where Ar is phenyl which can be substituted by alkyl, alkoxy, phenoxy, benzyloxy and phenoxymethyl, and where the aromatic substituents can carry further radicals X and Y selected from the following:
halogen such as fluorine, chlorine, bromine and iodine, especially fluorine and chlorine;
branched or unbranched $C_1$-$C_4$-alkyl such as methyl, ethyl, isopropyl and n-butyl, especially methyl and ethyl;
branched or unbranched $C_1$-$C_4$-alkoxy such as methoxy, ethoxy, 1-methylethoxy, n-propoxy and n-butoxy;
trifluoromethyl.

Particularly preferred arylglyoxylic esters VIIa are to be found in Table 1. o-Phenoxymethylglyoxylic esters of the formula VIIa'

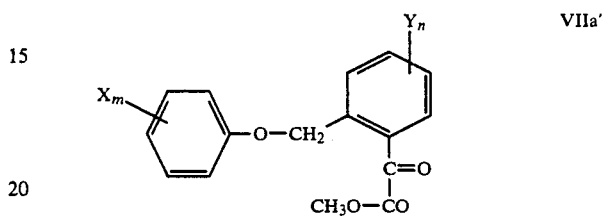

where
X' and Y are each halogen, $C_1$-$C_4$-alkyl, $C_1$-$C_4$-alkoxy or trifluoromethyl;
m is an integer from 0 to 4;
n is an integer from 0 to 3,
with the proviso that n can be 0 only when
X' is 2-chloro, 2-fluoro, 2-methyl, 4-methyl, 4-tertbutyl, 2-methoxy or 2-trifluoromethyl and m is 0 or 1 or X' is 2,4-dichloro or 4-chloro-2-methyl and m is 2,
are novel.

The arylglyoxylic esters VIIa and VIIa, are valuable intermediate products, in particular for synthesizing E-oxime ethers of phenylglyoxylic esters I

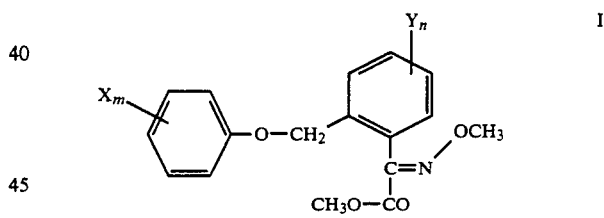

which are used in crop protection, preferably as fungicides (cf. EP-A 253,213 and EP-A 254,426).

The final products I can be prepared by reacting the arylglyoxylic esters VIIa, where appropriate as mixture of crude products together with the dimethyl acetals VIIb, with O-methylhydroxylamine or one of its acid addition salts, and the resulting E/Z isomer mixture is treated, simultaneously or subsequently, with an acid for substantial rearrangement of the z to the E isomer:

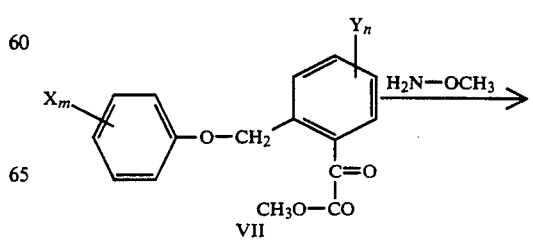

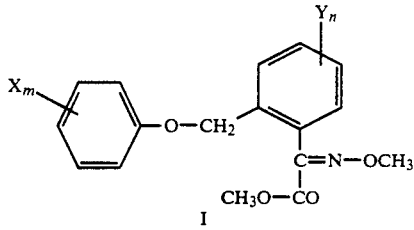

Precursor 1
1-Naphthoyl cyanide

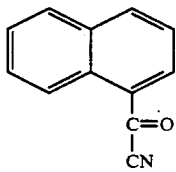

A mixture of 127 g (0.66 mol) of 1-naphthoyl chloride, 36 g (0.73 mol) of sodium cyanide, 0.2 g (0.6 mmol) of tetrabutylammonium bromide, 200 ml of water and 300 ml of 1,2-dichloroethane was stirred at high speed for 2 hours, maintaining at below 40° C. by cooling with ice-water. Working up was similar to Precursor γ. Yield: 55%; melting point: 90°-91° C.

Precursor 2
2-Phenylbenzoyl chloride

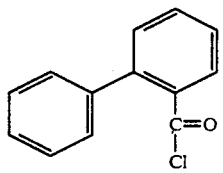

15.5 g (0.13 mol) of thionyl chloride were added dropwise to a mixture of 19.8 g (0.1 mol) of 2-phenylbenzoic acid, 10.3 g (0.13 mol) of pyridine and 100 ml of ether at 0° to 5° C. The reaction mixture was stirred at 20-25° C. for about 15 hours and then worked up as usual. Yield: 23.4 g of crude product.

Precursor 3
2-Phenylbenzoyl cyanide

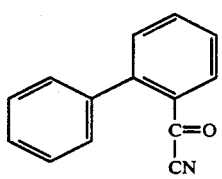

A mixture of 23.4 g (0.108 mol) of 2-phenylbenzoyl chloride, 190 ml of methylene chloride, 5.8 g (0.119 mol) of sodium cyanide, 0.1 g (0.3 mmol) of tetrabutylammonium bromide and 75 ml of water was stirred at 20° C. (ice-bath) for 3hours, then washed with water and worked up as usual.
Yield: 89%.

EXAMPLE 13 (according to the invention)

Methyl 2-(2-methylphenoxymethyl)phenylglyoxylate

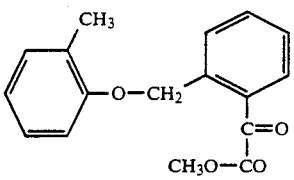

60 g (0.2 mol) of 2-(2-methylphenoxymethyl)-benzoyl cyanide were suspended in a mixture of 150 ml of methyl tert-butyl ether and 20 g (0.2 mol) of acetic anhydride. The mixture was cooled to −5° C. and then, at from −5° to 5° C., gaseous hydrogen chloride was passed in to saturation, and then the cooling was removed. The mixture was subsequently stirred at 20°-25° C. for about 20 hours and then 50 ml of methanol were added. The mixture was refluxed for 10 hours and then the solvent was removed under reduced pressure. The residue was dissolved in 200 ml of water and the aqueous phase was extracted with 300 ml of methyl tert-butyl ether. The ether phase was then washed three times with 50 ml of water each time and subsequently concentrated. 120 ml of methylene chloride and 40 ml of concentrated hydrochloric acid were added to the residue, after which the mixture was stirred at high speed at 20°-25° C. for about 15 hours. The phases were separated and then the organic phase was washed successively with concentrated aqueous sodium carbonate solution and water, then dried and concentrated. Yield: 59 g of a crude product which (according to gas chromatography) comprised 84 mol% of the required product.

$^1$H-NMR of the methyl 2-(2-methylphenoxymethyl)-phenylglyoxylate (in CDCl$_3$; TMS as internal standard): 2.3 ppm (s,3H); 3.80 ppm (s,3H); 5.40 ppm (s,2H); 6.90 ppm (t,2H); 7.15 ppm (t,2H); 7.45 ppm (t,1H); 7.65 ppm (t,1H); 7.80 ppm (d,2H).

EXAMPLE 14 (according to the invention)

Methyl 1-naphthoylglyoxylate

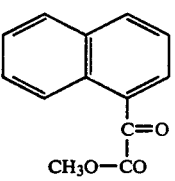

Dry hydrogen chloride was passed to saturation into a mixture of 30 g of 1-naphthoyl cyanide (precursor δ), 17 g of acetic anhydride and 80 ml of methyl tertbutyl ether while stirring at 0°-5° C. The mixture was then stirred at 20°-25° C. for 10 hours, during which a homogeneous solution formed. 200 ml of methanol were added and then the mixture was refluxed for 10 hours and subsequently concentrated under reduced pressure. The residue was dissolved in 300 ml of methyl tert-butyl ether, after which the solution was washed twice with 200 ml of water each time and finally dried and concentrated. Yield: 34 g of an oily mixture which (according to gas chromatography) comprised 58 mol% of the required product and 32 mol% of the dimethyl acetal of methyl 1-naphthylglyoxylate.

EXAMPLE 15

Methyl 1-biphenylylglyoxylate

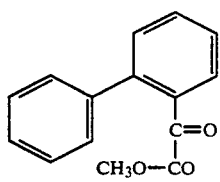

Dry hydrogen chloride was passed to saturation into a mixture of 20 g (97 mmol) of 2-phenylbenzoyl cyanide, 9.9 g (97 mmol) of acetic anhydride and 180 ml of methyl tert-butyl ether while stirring at −5° C. After the mixture had warmed to 20° C., 55 ml of methanol were added. The mixture was then stirred at 20°-25° C. for 72 hours, after which the solvent was removed. The residue was dissolved in methylene chloride, after which the organic phase was washed with water and worked up as usual.
Yield: 17.4 g.

We claim:

1. A process for preparing E-oxime ethers of phenylglyoxylic esters of the formula I

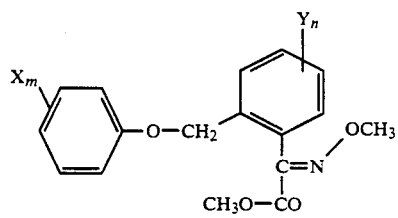

where
X and Y are each halogen, $C_1$-$C_4$-alkyl, $C_1$-$C_4$-alkoxy or trifluoromethyl;
m is an integer from 0 to 4;
n is an integer from 0 to 3;
which comprises the following steps
a) converting a phenol of the formula II

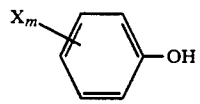

into the phenolate using a base in the presence of a diluent,
b) mixing this phenolate with a lactone of the formula III

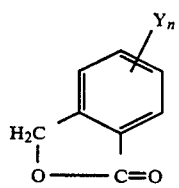

c) removing the diluent by distillation and reacting the mixture in the melt at from 50° and 250° C., and d) dissolving the still liquid melt in water and acidifying, and converting the resulting 2-phenoxymethylbenzoic acid of the formula IV

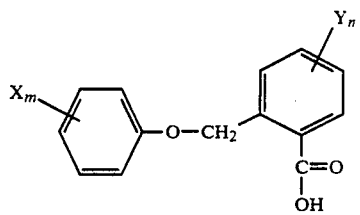

e) in a conventional manner with phosgene or thionyl chloride into the corresponding 2-phenoxymethylbenzoyl chloride of the formula V

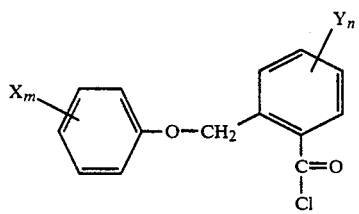

and
f) reacting the 2-phenoxymethylbenzoyl chloride V with an alkali metal or alkaline earth metal cyanide, in the presence or absence of hydrocyanic acid, and
g) reacting the resulting 2-phenoxymethylbenzoyl cyanide of the formula VI

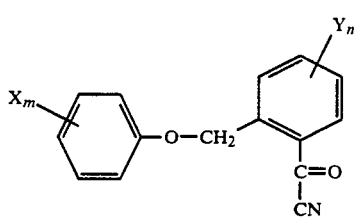

with methanol in the presence of an acid
h) and reacting the resulting methyl 2-phenoxymethylglyoxylate of the formula VIIa

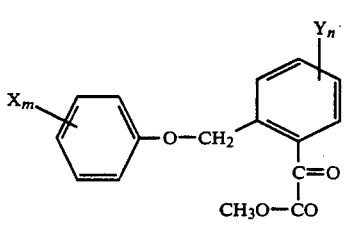

or an acetal of the formula VIIb

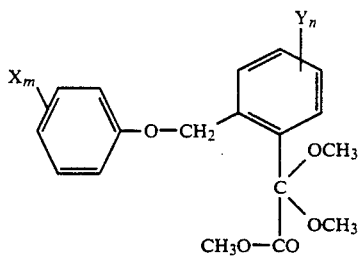

or a mixture of compounds VIIa and VIIb with O-methylhydroxylamine or one of its acid addition salts, and treating simultaneously or subsequently with an acid.

2. A process for preparing 2-phenoxymethylbenzoic acids of the formula IV as claimed in claim 1

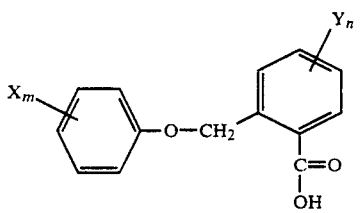

where
X and Y are each halogen, $C_1$–$C_4$-alkyl, $C_1$–$C_4$-alkoxy or trifluoromethyl;
m is an integer from 0 to 4;
n is an integer from 0 to 3,
which comprises
a) converting a phenol of the formula II

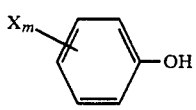

with a base into the phenolate in the presence of a diluent,
b) mixing this phenolate with a lactone of the formula III

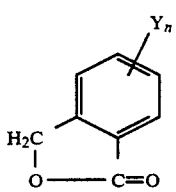

c) removing the diluent by distillation and reacting the molten mixture at from 50° to 250° C., and
d) dissolving the melt while still liquid in water and acidifying.

3. A process for preparing E-oxime ethers of phenylglyoxylic esters as claimed in claim 1, wherein, in step f) which comprises reacting a benzoyl chloride of the formula V

where X, Y, m and n have the meanings specified in claim 1, with an alkali metal or alkaline earth metal cyanide in either the presence or absence of hydrocyanic acid, said alkali metal and alkaline earth metal cyanides are selected from the group consisting of lithium, sodium, potassium, magnesium, calcium and barium cyanides.

4. A process for preparing E-oxime ethers of phenylglyoxylic esters as claimed in claim 1, wherein, in step e) which comprises reacting carboxylic acids of the formula IV

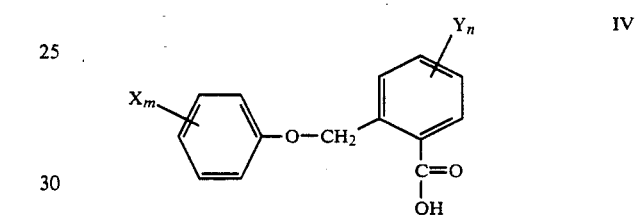

with phosgene or thionyl chloride, said reaction is carried out in the presence of a catalyst selected from the group consisting of amides, tertiary amines and phosphine oxides.

5. A process for preparing α-keto carboxylic esters of the formula VIIa as claimed in claim 1

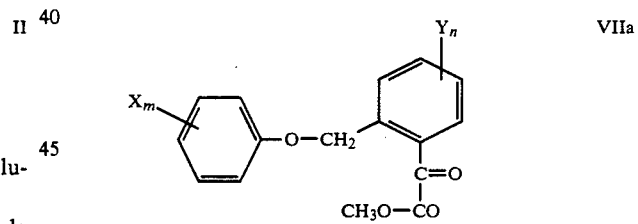

where X and Y are each halogen, $C_1$–$C_4$-alkyl, $C_1$–$C_4$-alkoxy or trifluoromethyl;
m is an integer from 0 to 4;
n is an integer from 0 to 3,
which comprises
a) reacting an o-phenoxymethylbenzoic ester of the formula Va

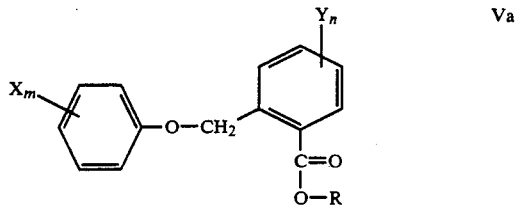

where R is $C_1$–$C_4$-alkyl, with dimethyl sulfoxide in the presence of a base, b) adding a halogenating agent to the β-keto sulfoxide product of the formula VIa

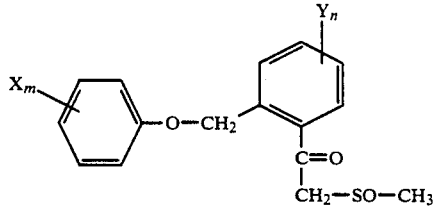 VIa and c) reacting this mixture with methanol in the presence of an acid.

6. A process for preparing E-oxime ethers of phenylglyoxylic esters according to claim 1 wherein step g) further comprises one or both of steps $g_1$) and $g_2$):

$g_1$) cleaving, under acidic conditions, any ketocarboxylic ester dimethyl acetal byproduct of the formula VIIb

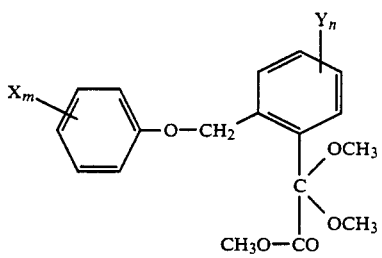 VIIb produced in step g), $g_2$) subjecting to reaction with methanol in the presence of an acid any alpha-keto carboxamide byproduct of the formula VIIc

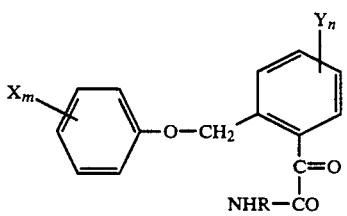 VIIc produced in step g) where R is hydrogen or acyl.

7. A process for preparing E-oxime ethers of phenylglyoxylic esters according to claim 1, wherein step g) further comprises step $g_3$):

$g_3$) reacting an o-phenoxymethyl benzoic ester of the formula Va

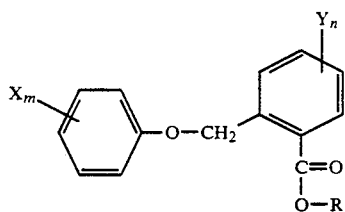 Va where R is $C_1$–$C_4$-alkyl, with dimethyl sulfoxide in the presence of a base,
mixing the resulting β-keto sulfoxide of the formula VIa

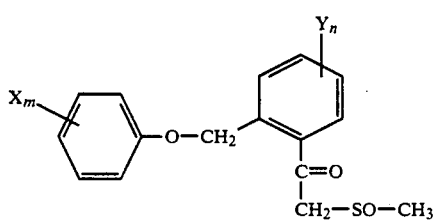 VIa with a halogenating agent and
reacting this mixture with methanol in the presence of an acid.

8. A process for preparing arylglyoxylic esters of the formula VIId

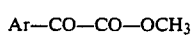 VIId where
Ar is phenyl or naphthyl, each of which can carry from one to four sustituents selected from the group consisting of halogen, alkyl, haloalkyl, alkoxy, haloalkoxy, alkoxyalkyl, phenyl, phenoxy, benzyloxy, naphthoxy, phenoxyalkyl, benzyloxyalkyl and naphthoxyalkyl, where the last seven substituents can be present only once and can carry from one to three of the following: halogen, alkyl, alkoxy, phenyl, phenoxy, plus as many halogen atoms as there are other carbon atoms which can be substituted,
which comprises
a) reacting an acyl cyanide of the formula VIb

 VIb with hydrogen chloride and tert-butyl methyl ester,
b) optionally, hydrolyzing any byproduct arylglyoxylamide of the formula VIIe from step a)

 VIIe where R is hydrogen or acyl, under acidic conditions in the presence of methanol,
c) optionally, hydrolyzing any byproduct dimethyl acetal of the arylglyoxylic esters of the formula VIIf

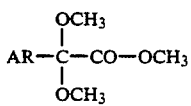 VIIf from step a).

* * * * *